United States Patent [19]

Luly et al.

[11] Patent Number: 5,190,922
[45] Date of Patent: Mar. 2, 1993

[54] TERMINALLY MODIFIED TRI-, TETRA- AND PENTAPEPTIDE ANAPHYLATOXIN RECEPTOR LIGANDS

[75] Inventors: Jay R. Luly; Megumi Kawai; Paul E. Wiedeman, all of Libertyville, Ill.

[73] Assignee: Abbott Laboratories, Abbott Park, Ill.

[21] Appl. No.: 710,209

[22] Filed: Jun. 4, 1991

[51] Int. Cl.$^5$ ......................... A61K 37/00; C07K 5/00
[52] U.S. Cl. ........................................ 514/18; 514/17; 514/19; 530/328; 530/329; 530/330; 530/331; 930/20; 930/21
[58] Field of Search ............................. 514/18, 17, 19; 530/330, 331, 328, 329; 930/20, 21

[56] References Cited

FOREIGN PATENT DOCUMENTS 9009162 8/1990 World Int. Prop. O. .

OTHER PUBLICATIONS

Eur. J. Immun. (1990) Kohl et al. vol. 20 1463–1468.

*Primary Examiner*—Merrell C. Cashion, Jr.
*Assistant Examiner*—B. Celsa
*Attorney, Agent, or Firm*—Jerry F. Janssen

[57] ABSTRACT

Oligopeptide compounds or oligopeptide analogue compounds of the formula A-B-D-E-G-J-L are ligands for the anaphylatoxin receptor and are useful in the treatment of inflammatory disease states. Also disclosed are anaphylatoxin receptor ligand compositions and a method for modulating anaphylatoxin activity.

13 Claims, No Drawings

TERMINALLY MODIFIED TRI-, TETRA- AND PENTAPEPTIDE ANAPHYLATOXIN RECEPTOR LIGANDS

TECHNICAL FIELD

This invention relates to organic compounds that modulate anaphylatoxin activity. It also relates to methods and compositions for modulating anaphylatoxin activity in human and animal hosts in need of such treatment.

BACKGROUND OF THE INVENTION

A wide variety of conditions including infection by bacteria, viruses or fungi, infiltration by cancer cells, allergic or autoimmune disorders and physically- or chemically-induced trauma causes an inflammatory response in humans. In all of these diseases and conditions in man and in most mammals, activation of the complement system (a set of proteins, regulatory factors and proteolytic enzymes) via either the classical or the alternative pathway, results in the generation of biologically active peptides which serve to amplify and exacerbate the resulting inflammation. The most active peptide, anaphylatoxin C5a, a 74-amino acid polypeptide, is generated by cleavage of the alpha-chain of native C5 at a specific site by convertases (proteolytic enzymes) of the blood complement system as well as by enzymes of the coagulation system. C5a exists in vivo in two biologically active forms. Once it is liberated from C5, the carboxyl terminal arginine of C5a is rapidly removed by carboxypeptidase-N, leaving the des-Arg derivative. Although C5a des-Arg is less active than C5a, both are potent inflammatory mediators at concentrations likely to be generated in vivo (Fernandez, H. N.; Henson, P. M.; Otani, A.; Hugli, T. E. J. Immunol. 1978, 120, 109.). Together, these peptides along with C3a, C4a, and their des-Arg degradation products, collectively described herein as anaphylatoxin, are capable of triggering diverse inflammatory reactions.

Among the various cell types, the neutrophil response to C5a is the best defined. Cell surface receptors specific for C5a have been demonstrated on the neutrophil (Chenoweth, D. E.; Hugli, T. E. Proc. Natl. Acad. Sci. U.S.A . 1978, 75, 3943–3947, Huey, R.; Hugli, T. E. J. Immunol. 1985, 135, 2063–2068, Rollins, T. E.; Springer, M. S. J. Biol. Chem. 1985, 260, 7157–7160.), and the ligand-receptor interaction promotes human polymorpho-nuclear leukocyte (PMN) migration in a directed fashion (chemotaxis), adherence, oxidative burst, and granular enzyme release from these cells (Hugli, T. E. Springer Semin. Immunopathol. 1984, 7, 193–219.). The interaction of C5a with PMN and other target cells and tissues results in increased histamine release, vascular permeability, smooth muscle contraction, and an influx into tissues of inflammatory cells, including neutrophils, eosinophils, and basophils (Hugli, T. E. Springer Semln. Immunopathol. 1984, 7, 193–219.). C5a may also be important in mediating inflammatory effects of phagocytic mononuclear cells that accumulate at sites of chronic inflammation (Allison, A. C.; Ferluga, J.; Prydz, H.; Scherlemmer, H. U. Agents and Actions 1978, 8, 27.). C5a and C5a des-Arg can induce chemotaxis in monocytes (Ward, P. A. J. Exp. Med. 1968, 128, 1201, Snyderman, R.; Shin, H. S.; Dannenberg, A. C. J. Immunol. 1972, 109, 896.) and cause them to release lysosomal enzymes (McCarthy, K.; Henson, P. S. J. Immunol. 1979, 123, 2511.) in a manner analogous to the neutrophil responses elicited by these agents. Recent studies suggest that C5a may have an immunoregulatory role by enhancing antibody particularly at sites of inflammation (Morgan, E. L.; Weigle, W. O.; Hugli, T. E. J. Exp. Med. 1982, 155, 1412, Weigle, W. O.; Morgan, E. L.; Goodman, M. G.; Chenoweth, D. E.; Hugli, T. E. Federation Proc. 1982, 41, 3099, Morgan, E. L.; Weigle, W. 0.; Hugli, T. E. Federation Proc. 1984, 43, 2543.).

C5a and C5a des-Arg play important roles in host defenses against bacterial infections and possibly in the mediation of some pathologic lesions such as the leukocyte infiltration seen in the lungs during acute respiratory distress syndrome. This mechanism seems to play a role in different pathological situations like pulmonary distress during hemodialysis, leukophoresis, cardiopulmonary bypass, and in acute myocardial infarction. Complement activation has been postulated to play an important pathological role in rheumatoid arthritis, serum sickness, systemic lupus erythematosus, ulcerative colitis, and forms of hepatic cirrhosis, chronic hepatitis, and glomerulonephritis, in certain shock states, during hemodialysis, and cardiopulmonary bypass, acute pancreatitis, myocardial infarction (which may be worsened by C5a-induced leukoembolization following the interaction of complement with atheromatous plaques), asthma, bronchoconstriction, some auto-allergic diseases, transplant rejection, and post-viral encephalopathies.

By serving as antagonists by binding to and blocking the anaphylatoxin receptor, certain compounds of the present invention can reduce or prevent anaphylatoxin-mediated inflammation. Other compounds of the present invention are agonists that mimic anaphylatoxin activity, and assist the body in building its defense mechanism against invasion by infectious agents and malignancy. Additionally, these compounds may influence the immunoregulatory effects of anaphylatoxin. The possible involvement of anaphylatoxin in a wide range of diseases, as indicated by these examples, suggests that anaphylatoxin receptor ligands could have clinical applications for the treatment and prevention of the above-mentioned pathological conditions.

SUMMARY OF THE INVENTION

In accordance with the principal embodiment of the present invention, there are provided anaphylatoxin activity modifying compounds of the formula A-B-D-E-G-J-L and the pharmaceutically acceptable salts, esters, or amides thereof.

In the generic formula given above, the groups A through have the following values:

A is $R_1$-$R_2$-$R_3$;

B iS $R_4$-$R_5$-$R_6$;

D is selected from $R_7$-$R_8$-$R_9$, $R_{35}$ and $R_{37}$;

E is selected from $R_{13}$-$R_{14}$-$R_{15}$, $R_{35}$ and $R_{37}$;

G, if present, is selected from a $R_{13}$-$R_{14}$-$R_{15}$, $R_{35}$ and $R_{37}$;

J is $R_{16}$-$R_{17}$-$R_{18}$;

L is $R_{19}$;

$R_1$ is selected from lower alkyl, alkoxy, aryl, aryloxy, arylalkoxy, carboxyalkyl, cyano, cyanoalkyl, amino, aminoalkyl, alkylamino, arylalkyl, aroyl, haloalkyl, hydroxyalkyl and hydrogen.

$R_2$ is selected from the group consisting of >$CR_{99}R_{100}$ and oxygen, with the proviso that when $R_2$ is oxygen, $R_1$ is aryl, lower alkyl or arylalkyl.

$R_3$ is selected from $>C=O$, $>CH_2$, and $-CH_2-C(O)-$, with the proviso that when $R_3$ is $>CH_2$, then $R_2$ cannot be oxygen.

$R_4$, $R_7$, $R_{10}$ and $R_{13}$ are independently selected from $>CH_2$ and $>NR_{50}$ where $R_{50}$ is hydrogen, lower alkyl or arylalkyl.

$R_5$ is $>CR_{201}R_{202}$.

$R_6$, $R_9$, $R_{12}$, $R_{15}$ and $R_{18}$ are independently selected from the group consisting of $>C=O$, $>CH_2$, and $-CH_2C(O)-$.

$R_8$ is $>CR_{210}R_{211}$.

$R_{11}$ is $>CR_{220}R_{221}$.

$R_{14}$ is $>CR_{230}R_{231}$.

$R_{16}$ is selected from the group consisting of oxygen, $NR_{50}$, and $CH_2$, with the proviso that when $R_{15}$ is $>C=O$ and $R_{16}$ is oxygen, then $R_{17}$, $R_{18}$ and $R_{19}$ taken together, represent hydrogen, lower alkyl, aryl or arylalkyl.

$R_{17}$ is $>CR_{301}R_{302}$.

$R_{19}$ is selected from the group Consisting of $-OH$ and $-CN$ groups, with the provisos that (i) when $R_{18}$ is $>C=O$, then $R_{19}$ is $-OH$; (ii) when $R_{18}$ is $>CH_2$, then $R_{19}$ is $-OH$ or $-CN$.

$R_{35}$ is a group having the structure

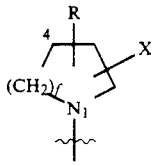

where f is and integer of 0 to 2, X is selected from $>C=O$ and $-CH_2-$. R is selected from hydrogen and lower alkyl, with the provisos that (i) when f is 0, X is at C-2 and R is at C-3 or C-4; (ii) when f is 1, X is at C-2 and R is at C-3, C-4 or C-5 and C-3,4 are saturated or unsaturated; and (iii) when f is 2, X is at C-2, C-3 or C-4 and R is at C-2, C-3, C-4, C-5 or C-6 when the position is unoccupied by X and C-3,4 or C-4,5 are saturated or unsaturated.

$R_{37}$ is a group having the structure

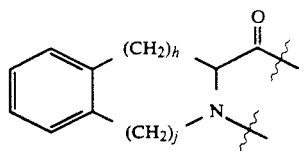

where h is 1 and j is 0 or 1.

$R_1$ $R_2$, taken together, optionally represent a group selected from aryl, arylalkyl or arylalkenyl.

$R_1$, $R_2$ and $R_3$, taken together, optionally represent a N-terminus protecting group.

$R_{17}$, $R_{18}$ and $R_{19}$, taken together, optionally represent a group selected from hydrogen, hydroxyalkyl, aryl, arylalkyl, amidinoalkyl, aminoalkyl, cyanoalkyl, cycloalkyl, (cycloalkyl)alkyl, (heterocyclic)alkyl, and guanadinoalkyl, wherein cycloalkyl may be substituted with aryl, amino, amidino and guanidino.

$R_{16}$, $R_{17}$, $R_{18}$ and $R_{19}$, taken together, optionally represent a group selected from the following (i) when R16 is $NR_{50}$, then $R_{17}$-$R_{18}$-$R_{19}$, taken together, is aminoalkyl, guanidinoalkyl, arylalkyl or (cycloalkyl)alkyl and (ii) when $R_{16}$ is $NR_{50}$ and $R_{17}$ is arylalkyl or (cycloalkyl)alkyl, then $R_{18}$-$R_{19}$ is arylalkyl, guanidinoalkyl or hydroxyalkyl.

$R_{16}$, $R_{17}$, $R_{18}$ and $R_{19}$, taken together, optionally represent a group of the following structures $R_{20}$, $R_{21}$, $R_{22}$, $R_{24}$ or $R_{25}$:

$R_{20}$ is

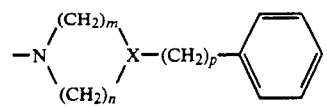

wherein m is integer of 1 to 3 and n is integer of 1 to 3 with proviso that either m or n must be 2; p is integer of 0–3; X is either carbon or nitrogen, $R_{21}$ is

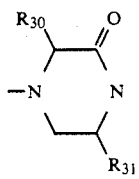

$R_{30}$ and $R_{31}$ are independently selected from arylalkyl, aminoalkyl, lower alkyl, guanidinoalkyl or (cycloalkyl)alkyl, $R_{22}$ is

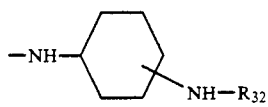

$R_{32}$ is selected from hydrogen or amidine, and the substituents on the cyclohexyl ring may be either cis or trans, $R_{24}$ is

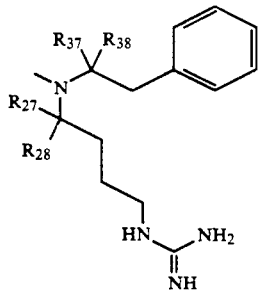

wherein $R_{27}$, $R_{28}$, $R_{37}$ and $R_{38}$ are independently selected from hydrogen or oxygen, with the provisos that (i) when $R_{27}$ and $R_{28}$ taken together are oxygen, then $R_{37}$ and $R_{38}$ are hydrogen and (ii) when $R_{37}$ and $R_{38}$ taken together are oxygen, then $R_{27}$ and $R_{28}$ are hydrogen, $R_{25}$ is

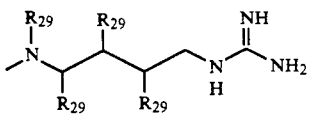

wherein R$_{29}$ is hydrogen, aryl or arylalkyl, with the proviso that when one of R$_{29}$ is aryl or arylalkyl, the remaining R$_{29}$ must be hydrogen.

R$_{18}$ and R$_{19}$, taken together, optionally represent hydrogen or R$_{23}$ R$_{23}$ is

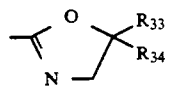

wherein, R$_{33}$ and R$_{34}$ are independently selected from lower alkyl, arylalkyl, (cycloalkyl)alkyl and cycloalkyl.

R$_{99}$ is independently selected from the group consisting of hydrogen, arylalkyl, aryl and lower alkyl.

R$_{100}$ is selected from the group consisting of hydrogen, lower alkyl and arylalkyl.

R$_{201}$ is selected from the group consisting of hydrogen, lower alkyl, arylalkyl, alkenyl, aryl, (cycloalkyl)alkyl, aminoalkyl, amidoalkyl, hydroxyalkyl, carboxyalkyl, (carboxamido)alkyl, (carboxyhydrazino)alkyl, ureidoalkyl, (heterocyclic)alkyl and guanidinoalkyl.

R$_{202}$, R$_{211}$, R$_{221}$, R$_{231}$, and R$_{302}$ are independently selected from hydrogen; arylalkyl, wherein arylalkyl at R$_{231}$ is benzyl, when J-L represents an L-Arginyl residue; and lower alkyl.

R$_{210}$ is selected from hydrogen, lower alkyl, aminoalkyl, amidoalkyl, aryl, arylalkyl, (cycloalkyl)alkyl, hydroxyalkyl, carboxyalkyl, (carboxamido)alkyl, ureidoalkyl, (carboxyhydrazino)alkyl, (heterocyclic)alkyl and guanidinoalkyl.

R$_{220}$, R$_{230}$, and R$_{301}$ are independently selected from the group consisting of hydrogen; lower alkyl; alkenyl; aryl; arylalkyl, wherein arylalkyl at R$_{230}$ is benzyl, when J-L represents an L-Arginyl residue; (cycloalkyl)alkyl; aminoalkyl, wherein aryl and arylalkyl amines are excluded from R$_{230}$ when J-L represents an L-Arginyl residue; amidoalkyl, wherein benzoyl amides and their heterocyclic variants are excluded from R$_{230}$ when J-L represents an L-Arginyl residue; hydroxyalkyl; guanidinoalkyl; carboxyalkyl; (carboxyamido)alkyl, wherein aniline amides and their heterocyclic variants are excluded from R$_{230}$ when J-L represents an L-Arginyl residue; (carboxyhydrazino)alkyl; ureidoalkyl and (heterocyclic)alkyl, wherein when J-L represents an L-Arginyl residue, then the heterocycle at R$_{230}$ can only be separated by one methylene unit from the alpha-carbon.

All of the foregoing definitions are with the provisos that, in the compounds of the present invention, (i) when A is an α-amino acid, then R$_{18}$-R$_{19}$ cannot be —CO$_2$H, and (ii) when R$_{18}$-R$_{19}$ is —CO$_2$H, then A cannot be an α-amino acid.

The present invention also relates to a method for modulating anaphylatoxin activity in a mammal in need of such treatment, comprising administering to the mammal a therapeutically effective amount of a compound of claim 1.

The invention further relates to anaphylatoxin modulating compositions comprising a pharmaceutical carrier and a therapeutically effective amount of a compound of claim 1.

DETAILED DESCRIPTION

As discussed above, C5a is the most active of a class of biologically active peptides which serves to amplify and exacerbate inflammation. While C5a contains 74 amino acid residues, it has been found in accordance with the present invention that oligopeptides containing as few as four amino acid residues are also actively bound by C5a receptors. Moreover, it has been found that peptidomimetic compounds (i.e. compounds which mimic the activity of peptides) in which certain groups replace the α-carbon, carbonyl group, and amide-nitrogen group of the individual amino acids in oligopeptides are also actively bound by C5a receptors.

The chemical structures of the compounds of the present invention are best understood by reference to the following structural formula in which it is understood that the segments are joined serially at the free valence bonds to form the compound A-B-D-E-G-J-L

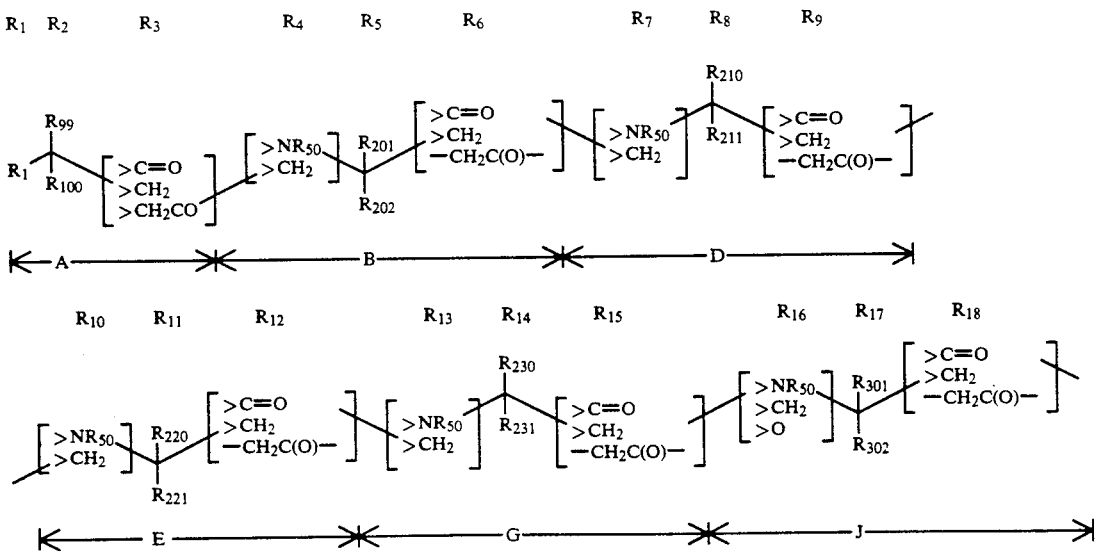

-continued

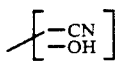

L

As used throughout this specification and the appended claims, the following terms have the meanings specified.

The term "alkyl" as used herein refers to monovalent straight chain or branched chain groups of 1 to 12 carbon atoms, including, but not limited to methyl, ethyl, n-propyl, isopropyl, n-butyl, sec-butyl, isobutyl, tert-butyl and the like.

The term "lower alkyl" as used herein refers to straight or branched chain alkyl groups containing from 1 to 8 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "alkylene" as used herein refers to divalent groups of from one to twelve carbon atoms derived by the removal of two hydrogen atoms from straight or branched saturated hydrocarbons. Examples include —$CH_2$—, —$CH(CH_3)$—, —$C(CH_3)_2$—, —$CH(C_2H_5)$—, —$CH_2CH_2$—, —$CH_2CH(CH_3)$—, —$C(CH_3)_2C(CH_3)_2$—, —$CH_2CH_2CH_2$— and the like.

The term "alkenyl" as used herein refers to straight or branched chain groups of 2 to 12 carbon atoms containing a carbon-carbon double bond, including, but not limited to ethenyl, 1-propenyl, 2-propenyl, 2-methyl-1-propenyl, 1butenyl, 2-butenyl and the like, wherein the alkenyl group may be substituted with cyano, carboxy, hydroxyalkyl and the like.

The term "amidinoalkyl" as used herein refers to a group having the structure -alkyl—$C(=NH)NH_2$ where the alkyl is as defined above.

The term "cycloalkyl" as used herein refers to cyclic groups, of 3 to 8 carbons, including, but not limited to cyclopropyl, cyclobutyl, cyclopentyl, cyclohexyl and the like, wherein the cycloalkyl group may be substituted with 1, 2 or 3 substituents independently selected from amino, aryl, halo, nitro, carboxy, cyano, $C_1$ to $C_{12}$ alkyl, alkoxy, aroyl, guanidino, sulfonamido and halosubstituted alkyl.

The term "(cycloalkyl)alkyl" as used herein refers to a cycloalkyl group appended to a lower alkyl group, including, but not limited to cyclohexylmethyl and cyclohexylethyl.

The term "alkoxy" as used herein refers to an alkyl group as defined above, attached to the remainder of the molecule through an oxygen atom. Alkoxy groups include, for example, methoxy, ethoxy, isopropoxy, n-butoxy, sec-butoxy, isobutoxy, tert-butoxy and the like.

The term "aryl" as used herein refers to substituted and unsubstituted carbocyclic aromatic groups including, but not limited to phenyl, 1- or 2-naphthyl, fluorenyl, (1,2)-dihydronaphthyl, (1,2,3,4)-tetrahydronaphthyl, indenyl, indanyl and the like, wherein the aryl group may be substituted with 1, 2, or 3 substituents independently selected from amino, halo, nitro, carboxy, cyano, $C_1$ to $C_{12}$ alkyl, alkoxy, aroyl, hydroxy, sulfonamido and halosubstituted alkyl.

The term "arylalkenyl" as used herein refers to an aryl group, as previously defined, appended to an alkenyl group, as previously defined, including, but not limited to 2-phenyl-ethen-1-yl, 2-phenyl-1-cyano-ethen-1-yl and the like.

The term "arylalkyl" as used herein refers to an aryl group, as previously defined, appended to an alkyl group, including, but not limited to benzyl, 1- and 2-naphthylmethyl, halobenzyl, alkoxybenzyl, hydroxybenzyl, aminobenzyl, nitrobenzyl, guanidinobenzyl, phenylmethyl(benzyl), 1-phenylethyl, 2-phenylethyl, 1-naphthylethyl and the like.

The term "benzyl" as used herein refers specifically to to phenyl substituted methyl in which the phenyl group may be substituted with 1, 2 or 3 substituents independently selected from halo, nitro, cyano, alkyl of from one to twelve carbon atoms, alkoxy, aroyl and halosubstituted alkyl and the like.

The term "aryloxy" as used herein refers to an aryl group as previously defined, attached to the parent molecular moiety through an oxygen atom. Aryloxy includes, but is not limited to phenoxy, 1-naphthoxy, 2-naphthoxy and the like.

The term "arylalkoxy" as used herein refers to an arylalkyl group as previously defined, attached to the parent molecular moiety through an oxygen atom. Arylalkoxy includes, but is not limited to benzyloxy, 2-phenethyloxy, 1-naphthylmethyloxy and the like.

The term "aroyl" as used herein refers to an aryl group as defined above, attached to the parent molecule through a carbonyl group. Examples include benzoyl and substituted benzoyl.

The term "alkylamino" as used herein refers to a group having the structure —NH(alkyl) where the alkyl portion is as defined above. Alkylamino groups include, for example, methylamino, ethylamino, isopropylamino and the like.

The term "dialkylamino" as used herein refers to a group having the structure —N(alkyl)(alkyl) where the two alkyl groups may be the same or different and are as previously defined.

The term "aminoalkyl" as used herein refers to a group having the structure —$NR_{342}R_{343}$ appended to a lower alkyl group, as previously defined. The groups $R_{342}$ and $R_{343}$ are independently selected from hydrogen, lower alkyl, aryl and arylalkyl. Additionally, $R_{342}$ and $R_{343}$ taken together, may optionally be —$(CH_2)_{mm}$— where mm is an integer of from 2 to 6.

The term "amidoalkyl" as used herein refers to a group having the structure —$NR_{344}C(O)R_{345}$ appended to a lower alkyl group, as previously defined. The groups $R_{344}$ and $R_{345}$ are independently selected from hydrogen, lower alkyl, aryl, arylalkyl and halosubstituted alkyl. Additionally, $R_{344}$ and $R_{345}$ taken together may optionally be —$(CH_2)_{kk}$— where kk is an integer of from 2 to 6.

The term "carboxyalkyl" as used herein refers to a carboxyl group, —$CO_2H$, appended to a lower alkyl group, as previously defined.

The term "(carboxyamido)alkyl" as used herein refers to a group of the formula —$C(O)NR_{340}R_{341}$, appended to a lower alkyl group, as previously defined.

The groups $R_{340}$ and $R_{341}$ are independently selected from hydrogen, lower alkyl, aryl and arylalkyl. Alternatively, $R_{340}$ and $R_{341}$ taken together may optionally be —$(CH_2)_{pp}$— wherein pp is an integer of from 2 to 6.

The term "cyanoalkyl" as used herein refers to a cyano group, —C≡N, appended to a lower alkyl group, as previously defined.

The term "guanidinoalkyl" as used herein refers to a group of the structure —$NR_{346}C(=NR_{347})NHR_{348}$ appended to a lower alkyl group, as previously defined. $R_{346}$, $R_{347}$ and $R_{348}$ are independently selected from hydrogen, lower alkyl and aryl.

The term "hydroxyalkyl" as used herein refers to a hydroxy group, —OH, appended to a lower alkyl group, as previously defined.

The term "ureidoalkyl" as used herein refers to a group having the structure —$NHC(O)NH_2$ appended to a lower alkyl group, as previously defined.

The term "heterocyclic" as used herein refers to any 50- or 6-membered ring containing from one to three heteroatoms independently selected from the group consisting of one nitrogen, oxygen, or sulfur, one oxygen and one nitrogen, one sulfur and one nitrogen, and one, two or three nitrogen; wherein the 5-membered ring has 0 to 2 double bonds and the 6-membered ring has 0 to 3 double bonds, wherein the nitrogen and sulfur heteroatoms may optionally be oxidized, wherein the nitrogen heteroatom may optionally be quaternized, and including any bicyclic group in which any of the above heterocyclic rings is fused to a benzene ring. Representative heterocycles include, but are not limited to pyrrolyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazoyl, oxazolidinyl, isoxazolyl, isoxazolidinyl, morpholinyl, indolyl, quinolinyl, thiazolyl, thiazolidinyl, isothiazolyl, isothiazolidinyl, isoquinolinyl, benzimidazolyl, benzothiazolyl, benzoxazolyl, furyl, thienyl and benzothienyl, wherein the heterocyclic group may be substituted with 1, 2, or 3 substituents independently selected from amino, halo, nitro, carboxy, Cyano, $C_1$ to $C12$ alkyl, alkoxy, aroyl, sulfonamido and halosubstituted alkyl.

The term "(heterocyclic)alkyl" as used herein refers to a heterocyclic group, as previously defined, appended to an alkyl group as previously defined.

The term "hydroxyalkyl" as used herein refers to -OH appended to a lower alkyl group.

The term "naturally occuring amino acid" refers to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The term "N-terminal protecting group" refers to those groups intended to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), benzoyl groups or an L- or D-aminoacyl residue, which may itself be N-protected similarly. Other groups may be found in Volume 3 of The Peptides, E. Gross and J. Meienhofer, Academic Press, 1981.

The term "anaphylatoxin" is used herein to mean C5a, C4a, C3a or the corresponding des-Arg degradation products.

The term "pharmaceutically acceptable salt" refers to non-toxic acid addition salts such as salts formed with inorganic acids such as hydrochloric acid, hydrobromic acid, phosphoric acid, sulfuric acid and perchloric acid or with organic acids such as acetic acid, oxalic acid, maleic acid, malic acid, tartaric acid, citric acid, succinic acid or malonic acid. Other pharmaceutically acceptable salts include inorganic nitrate, sulfate, acetate, malate, formate, lactate, tartrate, succinate, citrate, p-toluenesulfonate, and the like, including, but not limited to cations based on the alkali and alkaline earth metals, such as sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Examples of pharmaceutically acceptable, non-toxic esters of the compounds of this invention include $C_1$ to $C_6$ alkyl esters wherein the alkyl group is straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compound of formula I may be prepared according to conventional methods.

Examples of pharmaceutically acceptable, non-toxic amides of the compounds of this inveniton includes amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 to 6 membered heterocycle containing one nitrogen atom. Amides derived from ammonia, $C_1$ to $C_3$ alkyl primary amides and $C_1$ to $C_2$ dialkyl secondary amides are preferred. Amides of the compound of formula I may be prepared according to conventional methods.

Numerous asymmetric centers may exist in the compounds of the present inveniton. The present invention contemplates the various stereoisomers and mixtures thereof. In particular, chiral centers can exist at $R_2$, $R_5$, $R_8$, $R_{11}$, $R_{14}$ and $R_{17}$. Compounds of the present invention containing up to three α-amino acid residues of non-natural configuration have also been found to be effective as modulators of anaphylotoxin activity.

Particular stereoisomers are prepared by selecting the starting amino acids or amino analogs having the desired stereochemistry and reacting these starting materials by the methods detailed below. Starting compounds of particular stereochemistry are either commerically available or are made by the methods detailed below and resolved by techniques well known in the organic chemical arts.

One class of preferred compounds of the present invention are those in which the groups $R_4$, $R_7$, $R_{10}$, $R_{13}$ and $R_{16}$ are independently selected from >NH, >N— (lower alkyl), and >N(arylalkyl).

In another class of preferred compounds of the present invention, the groups $R_6$, $R_9$, $R_{12}$, $R_{15}$ and $R_{18}$ are independently selected from >C=O and >$CH_2$.

The group $R_5$ is preferably $CR_{201}R_{202}$; where $R_{201}$ is selected from the group consisting of aminoalkyl, lower alkyl, (cycloalkyl)alkyl, arylalkyl and quanidinoalkyl.

One class of preferred compounds of the present invention are those in which $R_{99}$ is selected from arylalkyl or arylalkenyl.

Another class of preferred compounds of the present invention are those in which D or E, but not both, are L-Proline, N-alkylamino acid or {(3R/S)-1,2,3,4-Tetrahydroisoquinolin-3-carbonyl}.

Another class of preferred compounds of the present invention are those in which $R_{230}$ is quanidinoalkyl; arylalkyl, wherein arylalkyl at $R_{230}$ is benzyl, when J-L represents an L-Arginyl residue; or (cycloalkyl)alkyl.

Another class of preferred compounds of the present invention are those in which $R_{301}$ is (cycloalkyl)alkyl, guanidinoalkyl or arylalkyl.

Another class of preferred compounds of the present inveniton are those in which the preferred chirality, if present, of $R_{11}$ and $R_{17}$ is of D- or unnatural configuration at the alpha position of amino acid residues E and J.

In one embodiment of the present inveniton A-B-D-E taken together is (N-Methyl)Phenylalanyl-Lysyl-Prolyl-{(2R)-2-Amino-3-cyclohexylpropanoyl}. Specific examples of compounds falling within this class include, but are not necessarily limited to, the following:

(N-Methyl)Phenylalanyl-Lysyl-Prolyl-{(2R)-2-Amino-3-cyclohexylpropanoyl}-N-{(1RS)-1-(Cyclohexylmethyl)-3-(guanidino)propyl}amide;

(N-Methyl)Phenylalanyl-Lysyl-Prolyl-{(2R)-2-Amino-3cyclohexylpropanoyl}-{(2S)-2-Amino-3-cyclohexylpropanoyl}-N-(3-Phenylpropyl)amide;

(N-Methyl)Phenylalanyl-Lysyl-Prolyl-{(2R)-2-Amino-3-cyclohexylpropanoyl}-Phenylalanyl-N-(3-Nitrobenzyl)amide;

(N-Methyl)Phenylalanyl-Lysyl-Prolyl-{(2R)-2-Amino-3-cyclohexylpropanoyl}-N-{(1S)-1-Cyclohexylmethyl-2-[N-(4-Guanidinobutyryl)amido]ethyl}amide;

(N-Methyl)Phenylalanyl-Lysyl-Prolyl-{(2R)-2-Amino-3cyclohexylpropanoyl}-{(2S)-2-Amino-3-cyclohexylpropanoyl}-N-(1-Naphthyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(5-Guanidinopentyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Naphthyl)methylamide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Guanidinopropyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1RS)-(1-Benzyl)-4-phenylbutylamide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1-Phenyl)cyclopropylmethyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1R/S)-1-Benzyl-4-guanidinobutyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(4-N,N-Dimethylamino)benzyl}amide;

(N-Methyl)Phenylalanyl-Lysyl-Prolyl-{(2R)-2-Amino-3-cyclohexylpropanoyl}-{(2S)-2-Amino-3cyclohexylpropanoyl}-N-(4-Guanidinobutyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-Benzylamide;

(N-Methyl)Phenylalanyl-Lysyl-Prolyl-{(2R)-2-Amino-3-cyclohexylpropanoyl}-N-}(1S)-1-Cyclohexylmethyl2-guanidinoethyl}amide;

(N-Methyl)Phenylalanyl-Lysyl-Prolyl-{(2R)-2-Amino-3-cyclohexylpropanoyl}-Phenylalanyl-N-}(1-Phenyl)cyclopropylmethyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-Diphenylmethylamide;

(N-Methyl)Phenylalanyl-Lysyl-Prolyl-{(2R)-2-Amino-3-cyclohexylpropanoyl}-Phenylalanyl-N-(2-Amidinoethyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Phenethyl)amide;

(N-Methyl)Phenylalanyl-Lysyl-Prolyl-{(2R)-2-Amino-3-cyclohexylpropanoyl}-{(2S)-2-Amino-3cyclohexylpropanoyl}-N-(2,2-Dimethyl-2-Phenethyl)amide;

(N-Methyl)Phenylalanyl-Lysyl-Prolyl-{(2R)-2-Amino-3-cyclohexylpropanoyl}-{(2S)-2-Amino-3cyclohexylpropanoyl}-N-}(1RS)-1-Benzyl-3phenylpropyl}amide;

(N-Methyl)Phenylalanyl-Lysyl-Prolyl-{(2R)-2-Amino-3-cyclohexylpropanoyl}-N-(3-Nitrobenzyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Picolyl)amide;

(N-Methyl)Phenylalanyl-Lysyl-Prolyl-{(2R)-2-Amino-3-cyclohexylpropanoyl}-{(2S)-2-Amino-3cyclohexylpropanoyl}-N-(2-(4-Hydroxyphenyl)ethyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Picolyl)amide;

(N-Methyl)Phenylalanyl-Lysyl-Prolyl-{(2R)-2-Amino-3-cyclohexylpropanoyl}-Phenylalanyl-N-Benzylamide;

(N-Methyl)Phenylalanyl-Lysyl-Prolyl-{(2R)-2-Amino-3-cyclohexylpropanoyl}-[(2S)-2-Amino-3cyclohexylpropanoyl]-N-(2-(Indol-3-yl)ethyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(Benzyloxy)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Picolyl)amide;

(N-Methyl)Phenylalanyl-Lysyl-Prolyl-{(2R)-2-Amino-3-cyclohexylpropanoyl}-N-}(1RS)-1-Benzyl-4-guanidinobutyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Fluorene)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(N'-Phenyl)hydrazide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-}(S)-1-Phenethyl)amide;

(N-Methyl)Phenylalanyl-Lysyl-Prolyl-{(2R)-2-Amino-3-cyclohexylpropanoyl}-{(2S)-2-Amino-3cyclohexylpropanoyl]-N-(2-Guanidinoethyl)amide;

(N-Methyl)Phenylalanyl-Lysyl-Prolyl-{(2R)-2-Amino-3-cyclohexylpropanoyl}-{(2S)-2-Amino-3- cyclohexylpropanoyl}-N-(1-Cyclohexyl-1-cyclopropylmethyl)amide;

(N-Methyl)Phenylalanyl-Lysyl-Prolyl-{(2R)-2-Amino-3-cyclohexylpropanoyl}-Phenylalanyl-N-(2-(4-Aminophenyl)ethyl)amide;

1-Benzyl-4-[(N-Methyl)Phenylalanyl-Lysyl-Prolyl-{(2R)-2-Amino-3-cyclohexylpropanoyl}-{(2S)-2-Amino-3-cyclohexylpropanoyl}]piperazine;

(N-Methyl)Phenylalanyl-Lysyl-Prolyl-{(2R)-2-Amino-3-cyclohexylpropanoyl}-Phenylalanyl-N-}(1S)-1-Phenethyl}amide;

(N-Methyl)Phenylalanyl-Lysyl-Prolyl-{(2R)-2-Amino-3-cyclohexylpropanoyl}-N-{(2-Cyclohexyl-2-methyl)propyl)amide;

and (N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Amidinoethyl)amide.

In another embodiment of the present invention B-D-E taken as a group is Lysyl-Prolyl-{(2R)-2-Amino-3-cyclohexylpropanoyl} and J is D-Arginyl-OH. Specific examples of compounds falling within this class include, but are not necessarily limited to, the following:

(S)-(+)-2-Phenylbutyryl-Lysyl-Prolyl-{(2R)-2-Amino-3cyclohexylpropanoyl}-{(2S)-2-Amino-3-cyclohexylpropanoyl}-DArginyl-OH;

}(R)-(−)-2-Ph-enylbutyryl}-Lysyl-Prolyl-{(2R)-2-Amino-3-cyclohexylpropanoyl}-{(2S)-2-Amino-3-cyclohexylpropanoyl}-DArginyl-OH;

Hydrocinnamoul-Lysyl-Prolyl-{(2R)-2-Amino-3-cyclohexylpropanoyl}-Phenylalanyl-DArginyl-OH;

{R(−)-3-Phenylbutyryl}-Lysyl-Prolyl-{(2R)-2-Amino-3-cyclohexylpropanoyl}-{(2S)-2-Amino-3-cyclohexylpropanoyl}-DArginyl-OH;

{(2-Benzyl-2-cyano-3-phenyl)propionyl)-Lysyl-Prolyl-{(2R)-2-Amino-3-cyclohexylpropanoyl}-{(2S)-2-Amino-3-cyclohexylpropanoyl}-DArginyl-OH;

}(R/S)-3-Amino-3-phenylpropionyl)-Lysyl-Prolyl-{(2R)-2-Amino-3-cyclohexylpropanoyl}-Phenylalanyl-DArginyl-OH;

{S(+)-3-Phenylbutyryl)-Lysyl-Prolyl-{(2R)-2-Amino-3-cyclohexylpropanoyl}-{(2S)-2-Amino-3-cyclohexylpropanoyl}-DArginyl-OH;

[2-{(S)-(+)-Methoxy)-2-phenylacetyl]-Lysyl-Prolyl{(2R)-2-Amino-3-cyclohexylpropanoyl}-Phenylalanyl-DArginyl-OH;

N-Phenylacetyl-Lysyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-{(2S)-2-Amino-3-cyclohexylpropanoyl}-DArginyl-OH;

{(3S)-Phenyllactyl)-Lysyl-Prolyl-{(2R)-2-Amino-3-cyclohexylpropanoyl}-Phenylalanyl-DArginyl-OH;

Phenoxyacetyl-Lysyl-Prolyl-{(2R)-2-Amino-3cyclohexylpropanoyl}-Phenylalanyl-DArginyl-OH;

(1-Phenyl-1-cyclopentane)carbonyl)-Lysyl-Prolyl}(2R)-2-Amino-3-cyclohexylpropanoyl}-Phenylalanyl-DArginyl-OH;

(2RS)-2-Cyano-3-phenylpropionyl)-Lysyl-Prolyl-{(2R)-2-Amino-3-cyclohexylpropanoyl}-Phenylalanyl-DArginyl-OH;

{(R/S)-(2-Carboxyl)-3-phenylpropionyl}-Lysyl-Prolyl{(2R)-2-Amino-3-cyclohexylpropanoyl}-{(2S)-2-Amino-3-cyclohexylpropanoyl}-DArginyl-OH;

{(R/S)-2-Cyano-3-phenylpropionyl)-Lysyl-Prolyl{(2R)2-Amino-3-cyclohexylpropanoyl}-{(2S)-2-Amino-3-cyclohexylpropanoyl}-DArginyl-OH;

and {(R/S)-2-Cyano-3-phenylpropionyl}-Lysyl-Prolyl{(2R)-2-Amino-3-cyclohexylpropanoyl}-{(2S)-2-Amino-3-cyclohexylpropanoyl}-DArginyl-OH In another embodiment of the present invention A is Hydrocinnamoyl and E is {(2R)-2-Amino-3-cyclohexylpropanoyl}. Specific examples of compounds falling within this class include, but are not necessarily limited to, the following:

Hydrocinnamoyl-Lysyl-}(3R/S)-1,2,3,4-Tetrahydroisoquinolin-3-carbonyl)-{(2R)-2-Amino-3-cyclohexylpropanoyl}-{(2S)-2-Amino-3-cyclohexylpropanoyl}-DArginyl-OH;

Hydrocinnamoyl-Norleucyl-Prolyl-{(2R)-2-Amino-3cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-{(2S)-2-Amino-3-cyclohexylpropanoyl}-DPhenylalanyl-OH;

Hydrocinnamoyl-Phenylalanyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3cyclohexylpropanoyl}-N-}(1S)-1-Cyclohexylmethyl-2-guanidino)ethyl)amide;

Hydrocinnamoyl-Arginyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-(N-Methyl)Alanyl-{(2R)-2-Amino-3-cyclohexylpropanoyl}-{(2S)-2-Amino-3-cyclohexylpropanoyl}-DArginyl-OH;

and Hydrocinnamoyl-Lysyl-Prolyl-{(2R)-2-Amino-3-cyclohexylpropanoyl}-(2S)-2-Amino-3-cyclohexylpropanoyl}-(N-Phenethyl)DArginyl-OH.

Method of Treatment

The compounds of the present invention serve to modulate the activity of anaphylatoxin. Certain compounds of the present invention function as anaphylatoxin antagonists, while others function as agonists. The antagonist compounds of the present invention block the anaphylatoxin receptor and prevent anaphylatoxin activity, which makes those compounds useful in the treatment and prevention of injurious conditions or diseases in which anaphylatoxin may be involved. Disease states in which anaphylatoxin is involved include asthma, bronchial allergy, chronic inflammation, systemic lupus erythematosus, vasculitis, serum sickness, angioedema, rheumatoid arthritis, osteoarthritis, gout, bullous skin diseases, hypersensitivity pneumonitis, idiopathic pulmonary fibrosis, immune complex-mediated glomerulonephritis, psoriasis, allergic rhinitis, adult respiratory distress syndrome, acute pulmonary disorders, endotoxin shock, hepatic cirrhosis, pancreatitis, inflammatory bowel diseases (including Crohn's disease and ulcerative colitis), thermal injury, Gram-negative sepsis, necrosis in myocardial infarction, leukophoresis, exposure to medical devices (including but not limited to hemodialyzer membranes and extracorpeal blood circulation equipment), chronic hepatitis, transplant rejection, post-viral encephalopathies, and/or ischemia induced myocardial or brain injury. These compounds may also be used as prophylactics for such conditions as shock accompanying Dengue fever. In addition, a combination of antibiotic and anti-inflammatory agent such as corticosteroids (e.g., methylprednisolone) and one or more of the above mentioned compounds may be employed.

Certain compounds of the invention are useful therapeutic agents because of their ability to mimic or promote anaphylatoxin activity and are therefore useful in stimulating the inflammatory response and immune response in mammals who are deficient in this regard. These agonist compounds may be used to assist the body in building its defense mechanism against invasion by infectious microorganisms or other stress. Interaction by these agonists at the anaphylatoxin receptor makes them useful in treating conditions or diseases including, but not limited to cancers (such as lung carcinoma), immunodeficiency diseases, and severe infections.

In some cases this will involve preventing the underlying cause of the disease state and in other cases, while the underlying disease will not be affected, the compounds of this invention will have the benefit of ameliorating the symptoms or preventing the manifestations of the disease.

The compounds of the present invention may be administered orally, parenterally, by inhalation spray, rectally, or topically in dosage unit formulations containing conventional nontoxic pharmaceutically acceptable carriers, adjuvants and vehicles as desired.

The term "parenteral" as used herein includes subcutaneous, intravenous, intramuscular, intrasternal, intraarterial injection or infusion techniques, without limitation. The term "topically" encompasses administration rectally and by inhalation spray, as well as by the more common routes of the skin and the mucous membranes of the mouth and nose.

Actual dosage levels of active ingredients in the pharmaceutical compositions of this invention may be varied so as to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 mg to about 100 mg, more typically from about 0.1 mg to about 20 mg, of active compound per kilogram of body weight per day are administered daily to a mammalian host. If desired, the effective daily dose may be divided into multiple doses for purposes of administration, e.g. two to four separate doses per day.

FORMULATION OF PHARMACEUTICAL COMPOSITION

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous cariers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

ANAPHYLATOXIN RECEPTOR BINDING KI DETERMINATION

Specific inhibition of $C_{5a}$ binding activity of representative compounds of the present invention was measured using 0.03-1 nM $^{125}I$-$C_{5a}$ with 2.5-25 μg/mL of purified PMNL membrane fragments (Borregaard, N.; Heiple, J. M.; Simons, E. R.; and Clark, R. A. J. Cell. Biol. 1983, 97, 52-61.). Free and membrane-bound ligand were separated by filtration. Binding potencies for representative examples of compounds of this invention are listed in Table 1.

TABLE 1

| In vitro C5a Receptor Binding Potency of Compounds of this Invention. | | | |
|---|---|---|---|
| Example | $K_i$ μM | Example | $K_i$ μM |
| 2 | 0.014 | 8 | 6.2 |
| 28 | 0.10 | 30 | 2.2 |
| 55 | 0.007 | 57 | 0.027 |
| 78 | 0.68 | 82 | 24.0 |
| 84 | 0.062 | 88 | 0.67 |
| 96 | 0.090 | 99 | 0.12 |
| 100 | 0.091 | 104 | 17.0 |
| 114 | 0.13 | 117 | 110.0 |
| 119 | 0.78 | 149 | 0.022 |
| 159 | 0.98 | 163 | 0.14 |
| 177 | 38.7 | 199 | 8.4 |
| 201 | 0.69 | 202 | 52.0 |
| 223 | 1.2 | 225 | 46.0 |

SYNTHESIS OF THE COMPOUNDS

The novel compounds and salts thereof of the inveniton can be utilized effectively as therapeutic agents. Accordingly, the present invention further relates to therapeutic compositions comprising a novel compound having the general formula I or salts thereof as an active component.

The compounds of the invention may be prepared by a synthetic method of elongation of a peptide chain through condensation of one amino acid by one, or by a method of coupling fragments consisting of two or several amino acids, or by a combination of these methods in accordance with conventional peptide synthesis methods.

The condensation of two amino acids, the condensation of an amino acid with a peptide or the condensation of one peptide with another peptide may be effected in accordance with conventional condensation methods such as azide method, mixed acid anhydride method, symmetrical anhydride method, DCC (dicyclohexylcarbodiimide) method, active ester method (p-nitrophenyl ester method, N-hydroxysuccinimide ester method, cyanomethyl ester method and the like), Woodward reagent K method, DCC-HOBT(1-hydroxy-benzotriazole) method and the like. These condensation reactions may be done by either solution methods or solid phase synthetic methods. When the peptide chain is elongated by the solid phase method, the C-terminal amino acid is linked to an insoluble carrier. As the insoluble carrier, any that can produce a detachable bond by reacting with a carboxyl group in a C-terminal amino acid may be used, and the examples thereof involve, for example, halomethyl resins such as chloromethyl resin, bromomethyl resin and the like, hydroxy-methyl resin, benzhydrylamine resin, and t-alkyloxycarbonyl hydrazide resin.

As conventional polypeptide synthesis, branched chain amino and carboxyl groups at alpha and omega positions in amino acids may be protected/deprotected if necessary. The protecting groups for amino groups which can be used involve, for example, benzyloxycarbonyl (Z), o-chlorobenzyloxycarbonyl ((2-Cl)Z), p-nitrobenzyloxycarbonyl (Z($NO_2$)), p-methoxy benzyloxycarbonyl (Z(OMe)), t-butoxycarbonyl (Boc), t-amyloxycarbonyl (Aoc), isobornyloxycarbonyl, admantyloxycarbonyl, 2-(4-biphenyl)-2-propyloxycarbonyl (Bpoc), 9-fluorenyl-methoxycarbonyl (Fmoc), methylsulfonylethoxycarbonyl (Msc), trifluoroacetyl, phthalyl, formyl, 2-nitrophenylsulfenyl (Nps), diphenylphosphinothioyl (Ppt), and dimethylphosphinothioyl (Mpt).

The examples of protecting groups for carboxyl groups involve, for example, benzyl ester (OBn), cyclohexyl ester, 4-nitrobenzyl ester (OBn$NO_2$), t-butyl ester (OtBu), 4-picolyl ester (OPic) and the like.

In the course of the synthesis of the present novel compounds, specific amino acids having functional groups other than amino and carboxyl groups in the branched chain such as arginine, cysteine, serine, and the like may be protected, if necessary, with suitable protecting group. It is preferable that for example, the guanidino group ($N_G$) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mds), 1,3,5-trimethylphenylsulfonyl (Mts) and the like, and the thiol group in cysteine may be protected with benzyl, p-methoxybenzyl, triphenylmethyl, acetamidomethyl, ethylcarbamyl, 4-methylbenzyl (4-MeBn), 2,4,6-trimethylbenzyl (Tmb) and the like, and the hydroxyl group in serine may be protected with benzyl (Bn), t-butyl, acetyl, tetrahydropyranyl and the like.

The compounds of the invention were prepared by standard solid phase peptide synthesis conditions as described in "Solid Phase Peptide Synthesis" by J. M. Stewart and J. D. Young, Second Edition (1984) and illustrated in Examples 1 and 2 in the experimental section.

The compounds of the invention may also be prepared by partial solid phase synthesis, fragment condensation methods and classical solution methods as exemplified by the methods described in "Peptide Synthesis", Second Edition, M. Bodanszky, Y. S. Klausner, and M. A. Ondetti (1976).

The standard chirality descriptors "R" and "S" are used to indicate an isomerically pure center, "RS" to indicate a mixture, and "R/S" to indicate a single pure isomer of undetermined configuration. The descriptor $\Psi\{X\}$ indicates the group, X, that is a replacement for the standard peptide bond, —C(O)NH—.

The foregoing may be better understood by reference to the following examples which are provided for illustration and not limitation of the practice of the invention. Unless otherwise indicated, the standard peptide methods described above and in examples 1 and 2 are used to assemble the different products, using the precursors indicated by the specific peptide sequence. The synthetic products were at least 95% pure, and gave NMR and mass spectra consistent with the proposed structure.

EXAMPLE 1

(S)-(+)-2-Phenylbutyryl-Lysyl(N-epsilon-Cbz)-Prolyl-{(2R)-2-Amino-3-cyclohexylpropanoyl}-{(2S)-2-Amino-3-cyclohexylpropanoyl}-DArginyl(N-guanidino-Tos)-Merrifield Resin Boc-DArg(N-guanidino-Tos)-Merrifield resin (0.4–1.0 g) was placed in a solid phase peptide synthesis vessel and amino acids were attached to the resin sequentially in the following order: Boc-(2S)-2-Amino-3-cyclohexylpropanoic acid Boc-(2R)-2-Amino-3-cyclohexylpropanoic acid, Boc-Proline, N-alpha-Boc-Lysine(N-epsilon-Cbz) and commercially available S(+)-2-Phenylbutyric acid. After the last coupling was carried out, the sequence was stopped at Agenda A-3 to yield (S)-(+)-2-Phenylbutyryl-Lysyl(N-epsilon-Cbz)-Prolyl-{(2R)-2-Amino-3-cyclohexylpropanoyl}-{(2S)-2-Amino-3-cyclohexylpropanoyl}-DArginyl(N-guanidino-Tos)-Merrifield Resin.

Following the synthesis, the protected peptide resin was removed from the reaction vessel by washing the resin three times with 20 mL DMF into a 30–60 mL sintered glass funnel, followed by washing the resin three times with 20 mL methylene chloride. The resin was dried at least five hours, then weighed.

Agenda A

1. Deblock: 45% trifluoroacetic acid (TFA) in methylene chloride containing 2.5% anisole (v/v/v).
2. Neutralization: 10% diisopropylethylamine (DIEA) in methylene chloride (v/v).
3. Single Coupling: 0.2–0.4M Boc-amino acid derivative in N,N-dimethylformamide (DMF), 0.2–0.4M diisopropylcarbodiimide (DIC) in methylene chloride, reaction time, 60 minutes.
4. Resin base washing: 10% DIEA in methylene chloride (v/v).
5. Single Coupling repeated: same as Step 3.
6. Go to next amino acid residue (go back to Step 1).
7. Upon attachment of the final amino acid to the growing peptide chain, the protecting group (t-Boc) is removed as in Step 1.

EXAMPLE 2

(S)-(+)-2-phenylbutyryl-Lysyl-Prolyl-{(2R)-2-Amino-3-cyclohexylpropanoyl}-{(2S)-2-Amino-3-cyclohexylpropanoyl}-DArginyl-OH The protected peptide resin of Example 1 (0.5 g) was treated with 1.0 mL anisole and 10 mL hydrogen fluoride (HF) for 60 minutes at 0° C. The HF and anisole were removed in vacuo at 0° C., and the mixture of the peptide and resin was washed with diethyl ether (2×25 mL). The crude peptide was extracted from the mixture by treatment with portions of 20% aqueous acetic acid (4×25 mL), lyophilized to a dry amorphous powder (148.3 mg), and purified by high performance liquid chromatography (HPLC) {column: 21.4 mm ID×25 cm or 41 4 mm ID×25 cm, Dynamax (Rainin), 8 μ silica, $C_{18}$ reverse-phase column}. The sample (70 mg) was purified by gradient elution{from 20 to 60% (80% acetonitrile in water with 0.1% trifluoroacetic acid)} at a flow rate of 15–45 mL/min. yield: 27.7 mg FAB+ MS: $(M+H)^+ = 852$ Amino Acid Anal.: Lys (0.97), Pro (1.08), Cha (1.94), Arg (1.03).

EXAMPLE 3

N-Boc-(N-Methyl)Phenylalanyl-Lysyl(N-epsilon-Boc)-Prolyl{(2R)-2-Amino-3-cyclohexylpropanoyl}-OH:

(2R)-2-Amino-3-cyclohexylpropanoic acid methyl ester hydrochloride was prepared from Boc-(2R)-2-Amino-3-cyclohexylpropanoic acid (30 g, 0.11 mole) in 500 mL of methanol and 250 mL of 4N hydrochloric acid in dioxane for overnight at room temperature in 93% yield. This (22.58 g, 0.101 mole) was coupled with Boc-Proline (25.89 g, 0.11 mole) in the presence of 1-(3-dimethylaminopropyl)-3-ethylcarbodiimide hydrochloride (EDC) (21.31 g, 0.11 mole), 1-hydroxybenzotriazole monohydride (HOBT) (15.0 g, 0.11 mole) and N-methylmorpholine (NMM) (12.2 mL, 0.11 mole) (EDC and HOBT method) in methylene chloride. The reaction was carried out at room temperature for overnight. Ethyl acetate was added and the organic layer was washed with saturated sodium bicarbonate, brine, 0.2M phosphoric acid, brine and dried over sodium sulfate. Evaporation of the solvent gave 35.03 g of dipeptide in 91% yield (MS: $(M+H)^+ = 383$). This was followed by deprotection of Boc-group, then coupling with N-alpha-Cbz-N-epsilon-Boc-Lysine to yield N-alpha-Cbz-Lysyl(N-epsilon-Boc)-Prolyl-{(2R)-2-Amino-3-cyclohexylpropanoyl}-OMe (MS: $(M+H)^+ = 645$) in 89% yield using the conditions mentioned above (EDC and HOBT method).

The Cbz-group was cleaved by hydrogenolysis to obtain H-Lysyl(N-epsilon-Boc)-Prolyl-{(2R)-2-Amino-3-cyclohexylpropanoyl}-OMe (MS: $(M+H)^+ = 511$), and then coupled with N-Boc-(N-Methyl)Phenylalanine by the method above (EDC and HOBT method) in quantitative yield to obtain N-Boc-(N-Methyl)Phenylalanyl-Lysyl(N-epsilon-Boc)-Prolyl-{(2R)-2-Amino-3-cyclohexylpropanoyl}-OMe (MS: $(M+H)^+ = 772$).

The obtained methyl ester (7.33 g, 9.5 mmole) was dissolved in 90 mL of methanol and 25 mL of water in an ice bath. Lithium hydroxide (0.6 g, 14.3 mmole) in 25 mL of water was slowly added and the reaction mixture was stirred at room temperature for 5 hours. The methanol was removed and 50 mL of water was added. The aqueous layer was washed with ether (2×) and acidified using 1M phosphoric acid. The compound was extracted with ethyl acetate, and the ethyl acetate layer was washed with brine and dried over sodium sulfate. Evaporation of the solvent gave 5.94 g (83%) of the title compound.

(MS: $(M+H)^+ = 758$).

This compound was used to prepare the following examples 10, 16, 18, 22, 35, 46, 59, 66, 73, 74, 78, 79, 85, 95, 98, 107, 110, 115, 117, 118, 119, 121, 122, 130, 134, 135, 136, 137, 143, 144, 145, 155, 156, 157, 167, 180, 179, 190, 196, 200, 212, 220, and 221.

EXAMPLE 4

N-Boc-(N-Methyl)Phenylalanyl-Lysyl(N-epsilon-Boc)-Prolyl{(2R)-2-Amino-3-cyclohexylpropanoyl}-Phenylalanyl-OH The coupling of Example 3 [N-Boc-(N-Methyl)-PhenylalanylLysyl(N-epsilon-Boc)-prolyl-{(2R)-2-Amino-3-cyclohexylpropanoyl}-OH](5.0 g, 6.6 mmole) and H-Phenylalanine methyl ester hydrochloride (1.57 g, 7.3 mmole) was carried out using EDC (1.52 g, 7.9 mmole), HOBT (1.1 g, 7.9 mmole) and NMM (0.78 mL, 7.9 mmole) in 60 mL of methylene chloride. N-Boc-(N-Methyl)Phenylalanyl-Lysyl(N-epsilon-Boc)-Prolyl-{(2R)-2-Amino-3-cyclohexylpropanoyl}-Phenylalanine methyl ester was obtained in quantitative yield. The product obtained was dissolved in 50 mL of methanol and 10 mL of water. Lithium hydroxide (0.42 g, 9.9 mmole) in 10 mL of water was added to hydrolyze the ester. After treatment by the procedure described in Example 3, the title compound (5.9 g) was obtained in 99% yield.(MS: $(M+H)^+ = 905$). The compound was used to prepare the following examples: 13, 14, 21, 24, 25, 38, 50, 58, 72, 97, 100, 125, 129, 130, 131, 140, 142, 151, 152, 154, 164, 165, 166, 170, 177, 178, 184, 185, 187, 189, 194, 197, 198, 201, 203, 204, 205, 208, 210, 211, and 219.

EXAMPLE 5

N-Boc-(N-Methyl)Phenylalanyl-Lysyl(N-epsilon-Boc)-Prolyl{(2R)-2-Amino-3-cyclohexylpropanoyl}-{(2S)-2-Amino-3-cyclohexylpropanoyl}-OH N-Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropanoyl}-OEt was prepared starting from (2S)-2-Amino-3-cyclohexylpropanoic acid ethyl ester hydrochloride. The coupling methods, reaction conditions, and worked-ups were analogous to the procedures described in Example 3 to give the following intermediates:

Boc-{(2R)-2-Amino-3-cyclohexylpropanoyl}-{(2S)-2-Amino-3-cyclohexylpropanoyl}-OEt (MS: $(M+H)^+ = 453$) in 72% yield; Boc-Prolyl-{(2R)-2-Amino-3-cyclohexylpropanoyl}-{(2S)-2-Amino-3-cyclohexylpropanoyl}-OEt (MS: $(M+H)^+ = 550$) in quantitative yield;

Cbz-Lysyl(N-epsilon-Boc)-Prolyl-{(2R)-2-Amino-3-cyclohexylpropanoyl}-{(2S)-2-Amino-3-cyclohexylpropanoyl}-OEt (MS: $(M+H)^+ = 812$) in 97% yield;

and N-Boc-(N-Methyl)Phenylalanyl-Lysyl(N-epsilon-Boc)-Prolyl{(2R)-2-Amino-3-cyclohexylpropanoyl}-{(2S)-2-Amino-3-cyclohexylpropanoyl}-OEt (MS: $(M+H)^+ = 939$) in 96% yield.

To the above ethyl ester (7.08 g, 7.54 mmole) was dissolved in 70 mL of methanol and 19 mL of water and was added 1.7 equivalents of lithium hydroxide (0.54 g, 12.8 mmole) in 29 mL of water. Work-up was as described in Example 3 to afford the title compound (6.5 g, 95%). (MS: $(M+H)^+ = 911$).

The title compound was used to prepare the following examples 11, 12, 19, 20, 23, 29, 30, 34, 36, 37, 40, 42, 43, 48, 49, 53, 55, 56, 60, 61, 62, 63, 75, 76, 77, 83, 87, 89, 90, 96, 101, 102, 103, 108, 109, 112, 113, 114, 116, 120, 126, 127, 128, 132, 138, 139, 141, 145, 146, 150, 158, 162, 163, 169, 175, 176, 182, 183, 186, 188, 191, 193, 195, 206, 207, 214, 215, 216, 217, 218, 223, 222, and 224.

EXAMPLE 6

Hydrocinnamoyl-Lysyl-{(3R/S)-1,2,3,4-Tetrahydroisoquinolin-3-carbonyl)-}(2R)-2-Amino-3-cyclohexylpropanoyl}-{(2S)-2-Amino-3-cyclohexylpropanoyl}- · DArginyl-OH This compound is prepared using the techniques described in Examples 1 and 2.

EXAMPLE 7

{(R)-(−)-2-Phenylbutyryl)-Lysyl-Prolyl-}(2R)-2-Amino-3-cyclohexylpropanoyl}-{(2S)-2-Amino-3-cyclohexylpropanoyl}-DArginyl-OH FAB+ MS: $(M+H)^+ = 852$. Amino Acid Anal: Lys (0.95), Pro (1.18), Cha (2.03), Arg (1.05).

EXAMPLE 8

{(2R/S)-2-Hydroxymethyl-2-phenylacetyl}-Lysyl-Prolyl-{(2R)-2-Amino-3-cyclohexylpropanoyl}-Phenylalanyl-DArginyl-OH The title compound was prepared from commercially available (2R/S)-2-hydroxymethyl-2-phenylacetyl chloride and the diastereomers were separated by RP-HPLC.

FAB+ MS: $(M+H)^+ = 848$. Amino Acid Anal: Arg (1.06), Lys (0.96), Pro (0.96), Cha (1.03), Phe (1.02).

EXAMPLE 9

{(2R/S)-2-Hydroxymethyl-2-phenylacetyl}-Lysyl-Prolyl-{(2R)-2-Amino-3-cyclohexylpropanoyl}-Phenylalanyl-DArginyl-OH This compound was one of the isomers described in Examples 8 and was isolated by RP-HPLC.

FAB+ MS: $(M+H)^+ = 848$ Amino Acid Anal: Arg (1.02), Lys (0.98), Pro (0.98), Cha (0.99), Phe (1.02).

EXAMPLE 10

3-{(3R)-Benzyl}-6-55 (6R)-(3-Guanidino)propyl}-4-[(N-Methyl)Phenylalanyl-Lysyl-Prolyl-{(2R)-2-Amino-3cyclohexylpropanoyl}]-Piperazine-2-one N-alpha-Boc-DArginine(guanidino-Tos)-N,Odimethylhydroxamate was prepared from N-alpha-Boc-DArginine(guanidino-Tos) (2.14 g, 5 mmole) and N,O-dimethylhydroxylamine hydrochloride (0.536 g, 5.5 mmole) in 25 mL of methylene chloride in the presence of N-methylmorpholine (NMM) (0.605 g, 5.5 mmole) and 1-(3-dimethylaminopropyl)-3-ethylcarbodiimide hydrochloride (EDC) (1.05 g, 5.5 mmole) in quantitative yield, according to the literature: Nahms, S.; Weinreb, S. M. Tetrahedron Lett., 1981, 22, 3815, The hydroxamate obtained (2.358 g, 5 mmole) was treated with lithium alminium hydride (LAH) (15 mL, 15 mmole) in 70 mL of tetrahydrofuran (THF) according to the cited reference to obtain the cyclic aminal form of N-alpha-Boc-Arginal(guanidino-Tos) in quantitative yield.

To commercially available D-Phenylalanine methyl ester hydrochloride (1.078 g, 5 mmole) dissolved in 10 mL of methyl alcohol and cooled in an ice bath was added triethylamine (TEA) (0.697 mL, 5 mmole). Then the above Arginal derivative (5 mmole) in 20 mL of 1%-acetic acid in methanol followed by 100 μL of acetic acid were added, the ice bath was removed, and the reaction mixture was stirred for 30 minutes. Sodium cyanoborohydride (NaCNBH$_3$) (943 mg, 15 mmole) in 20 mL of methanol was added dropwise over a period of 40 minutes, and the reaction mixture was allowed to stir at room temperature for one overnight. The reaction mixture was poured into cold 10% sodium bicarbonate solution and the compound was extracted with ethyl acetate. The ethyl acetate layer was washed with 10% sodium bicarbonate, brine, and dried over anhydrous magnesium sulfate. Evaporation of the solvent gave 2.508 g of crude product, which was then purified on silica gel column chromatography, eluting with 1.5% methanol in chloroform to yield 1.854 g (64.4%) of N-alpha-Boc-DArginyl(guanidino-Tos)-Ψ(CH$_2$NH)-DPhenylalanyl-OMe. The peptide obtained (575.6 mg, 1 mmole) was treated with 10 mL of 4N hydrochloric acid in dioxane for 1 hour at room temperature and evaporated to dryness. The material obtained was dissolved in 30 mL of dry methanol and diisopropylethylamine (0.348 mL, 2 mmole) was added. The reaction mixture was gently refluxed for 4 days. Methanol was removed and methylene chloride was added. The organic phase was washed with water (4×), dried over sodium sulfate and the solvent was removed to yield 220 mg of {3-[(3R)-Benzyl]-6-[(6R)-(3'-guanidino-Tos)-propyl]-piperazine-2-one}.

This piperazine-2-one analogue( 66.5 mg, 0.15 mmole) was reacted with the Example 3, N-Boc-(N-Methyl)PhenylalanylLysyl(N-epsilon-Boc)-Prolyl-{(2R)-2-Amino-3-cyclohexylpropanoyl}-OH, (113.7 mg, 0.15 mmole) using 1-(3-dimethylaminopropyl)-3-ethylcarbodiimide hydrochloride (EDC) (31.7 mg, 0.165 mmole) in 2.5 mL of methylene chloride. The crude product (152 mg) was treated with HF-anisole as exemplified in Example 2. 2/3 of crude peptide was purified to yield 30.5 mg of title compound.

FAB+ MS: (M+H)+ =829. Amino Acid Anal: MePhe (1.08), Lys (0.96), Pro (1.04), Cha (1.00).

EXAMPLE 11

(N-Methyl)Phenylalanyl-Lysyl-Prolyl-{(2R)-2-Amino-3-cyclohexylpropanoyl}-{(2S)-2-Amino-3-cyclohexylpropanoyl}-N-{4-(Amidino)butyl}amide The compound was prepared in analogy to Example 105.

FAB+ MS: (M+H)+ =808. Amino Acid Anal: MePhe (0.98), Lys (0.98), Pro (1.02), Cha (1.88).

EXAMPLE 12

(N-Methyl)Phenylalanyl-Lysyl-Prolyl-{(2R)-2-Amino-3-cyclohexylpropanoyl}-{(2S)-2-Amino-3-cyclohexylpropanoyl}-N(2-trans-dl-Phenylcyclopropyl)amide FAB+ MS: (M+H)+ =826 , Amino Acid Anal: MePhe (0.94), Lys (0.96), Pro (1.04), Cha (1.81).

EXAMPLE 13

4-Benzyl-1-[(N-Methyl)Phenylalanyl-Lysyl-Prolyl-{(2R)-2-Amino-3-cyclohexylpropanoyl}-Phenylalanyl]-piperazine FAB+ MS (M+H)+ =863 . Amino Acid Anal: Lys (0.96), Pro (0.99). Cha (0.97). Phe (1.04), MePhe (098).

EXAMPLE 14

(N-Methyl)Phenylalanyl-Lysyl-Prolyl-{(2R)-2-Amino-3-cyclohexylpropanoyl)-Phenylalanyl-N-(4-Nitrobenzyl)amide FAB+ MS: (M+H)+ =839. Amino Acid Anal: Lys (0.95), Pro (1.00), Cha (0.99), Phe (1.04), MePhe (0.71).

EXAMPLE 15

(N-Methyl)Phenylalanyl-Lysyl-Prolyl-DArginyl-Phenylalanyl-N-(4-Picolyl)amide

FAB+ MS: (M+H)+ =798. Amino Acid Anal: Lys (Present), Pro (1.02), Phe (0.99), MePhe (0.99), Arg (1.01).

EXAMPLE 16

(N-Methyl)Phenylalanyl-Lysyl-Prolyl-{(2R)-2-Amino-3-cyclohexylpropanoyl}-{(2S)-2-Amino-3-cyclohexylpropanoyl}-NH$_2$ The compound was prepared in analogy to Example 107, FAB+ MS: (M+H)+ =710 Amino Acid Anal: MePhe (0.83), Lys (0.96), Pro (1.03), Cha (1.99).

EXAMPLE 17

Cinnamoyl-Lysyl-Prolyl-{(2R)-2-Amino-3-cyclohexylpropanoyl}-Phenylalanyl-DArginyl-OH FAB+ MS: (M+H)+ =830. Amino Acid Anal: Lys (0.99), Pro (0.97), Cha (0.90), Phe (0.98), Arg (1.03).

EXAMPLE 18

(N-Methyl)Phenylalanyl-Lysyl-Prolyl-{(2R)-2-Amino-3-cyclohexylpropanoyl}-N-(6-Guanidinohexyl)-N-(2Phenethyl)amide The compound was prepared in analogy to Example 42, FAB+ MS: (M+H)+ =802. Amino Acid Anal: MePhe (0.82), Lys (0.97), Pro (1.03), Cha (0.87).

EXAMPLE 19

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Aminobutyl)amide Boc-1,4-diaminobutane was prepared in analogy to literature methods: Itoh, M.; Hagiwara, D.; Kamiya, T.; Tetrahedron Lett., 1975, 4393, Itoh, M.; Hagiwara, D.; Kamiya, T.; Bull Chem. Soc. Jpn., 1977, 50, 718, Boc-(N-Methyl)Phenylalanyl-Lysyl(N-epsilon-Boc)-Prolyl{(2R)-2-Amino-3-cyclohexylpropanoyl}-{(2S)-2-Amino-3-cyclohexylpropanoyl}-OH (Example 5) (100 mg, 0.11 mmole) was coupled with Boc-1,4-diaminobutane (24 mg, 0.11 mmole) via the mixed anhydride method as exemplified in Example 116. Cleavage of the protecting groups using trifluoroacetic acid in methylene chloride and purification gave the title compound (78 mg) in 63.5% yield FAB+ MS: (M+H)+ =781. Amino Acid Anal: MePhe (0.89), Cha (1.86), Lys (0.98), Pro (1.02).

EXAMPLE 20

Hydrocinnamoyl-Norleucyl-Prolyl-{(2R)-2-Amino-3-cyclohexylpropanoyl}-{(2S)-2-Amino-3-cyclohexylpropanoyl}-DArginyl-OH This compound is prepared using the techniques described in Examples 1 and 2.

EXAMPLE 2

(N-Methyl)Phenylalanyl-Lysyl-Prolyl-{(2R)-2-Amino-3-cyclohexylpropanoyl}-Phenylalanyl-N-{(2R/S)-2Phenylbutyl}amide (1-(1-Phenyl)cyclopropyl)methylamine (125 mg, 0.7 mmole) was hydrogenated in the presence of palladium-black (200 mg) in 20 mL of acetic acid under 4 atmospheres of hydrogen at room temperature to yield (2R/S)-2-Ethyl-2-phenethylamine as an acetate salt in quantitative yield. This (27.7 mg, 0.12 mmole) was coupled with the compound (Example 4) (100 mg, 0.1 mmole) via the EDC and HOBT method. 81.4 mg (70%) of the title compound was isolated.

FAB+ MS: (M+H)+=836. Amino Acid Anal: MePhe (105), Lys (1.00), Pro (1.04), Cha (0.97), Phe (0.99).

EXAMPLE 22

(N-Methyl)Phenylalanyl-Lysyl-Prolyl-{(2R)-2-Amino-3cyclohexylpropanoyl}-N-{(1RS)-1-(Cyclohexylmethyl)-3(guanidino)propyl}amide Boc-(2S)-2-Amino-3-cyclohexylpropanol (1.1 g, 4.3 mmole) was reacted with methanesulfonyl chloride (mesyl chloride) (0.4 mL, 5.2 mmole) and TEA (0.71 mL, 5.2 mmole) in 10 mL of methylene chloride. Half of the obtained O-mesylated product was treated with potassium cyanide (1.36 g, 21 mmole) in 5 mL of dimethylsulfoxide (DMSO) at 40° C. for one overnight to afford 3-Boc-amino-{(2S)-2-cyclohexylmethyl}propionitrile (470 mg, 85%). This material (440 mg, 1.7 mmole) was hydrogenated (1.7 g of Raney nickel in 80 mL of methanol and 20 mL of ammonia) and the amine obtained (0.9 mmole) was guanidinated, deprotected of its Boc group, and was then coupled with the compound of Example 3 to afford the title compound.

FAB+ MS: (M+H)+=752. Amino Acid Anal: MePhe (0.96), Lys (1.00), Pro (1.00), Cha (0.86).

EXAMPLE 23

(N-Methyl)Phenylalanyl-Lysyl-Prolyl-{(2R)-2-Amino-3-cyclohexylpropanoyl}-{(2S)-2-Amino-3-cyclohexylpropanoyl}-N(3-Phenylpropyl)amide FAB+ MS: (M+H)+=828. Amino Acid Anal: MePhe (0.95), Lys (1.02), Pro (0.98), Cha (1.88).

EXAMPLE 24

4-Benzyl-1-[(N-Methyl)Phenylalanyl-Lysyl-Prolyl-{(2R)-2-Amino-3-cyclohexylpropanoyl}-Phenylalanyl]piperidine FAB+ MS: (M+H)+=862. Amino Acid Anal: Lys (0.91), Pro (0.96), Cha (0.91), Phe (1.13) MePhe (1.11).

EXAMPLE 25

(N-Methyl)Phenylalanyl-Lysyl-Prolyl-{(2R)-2-Amino-3-cyclohexylpropanoyl}-Phenylalanyl-N-(3-Nitrobenzyl)amide FAB+ MS: (M+H)+=839. Amino Acid Anal: Lys (0.95), Pro (1.01), Cha (0.97), Phe (1.05), MePhe (0.69).

EXAMPLE 26

(N-Methyl)Phenylalanyl-Lysyl-Prolyl-DArginyl-Phenylalanyl-N-Benzylamide

FAB+ MS: (M+H)+=797. Amino Acid Anal: Lys (Present), Pro (1.05), Phe (0.99), MePhe (0.98), Arg (1.01).

EXAMPLE 27

3-Aminopropionyl-Phenylalanyl-Lysyl-Prolyl-{(2R)-2-Amino-3-cyclohexylpropanoyl}-{(2S)-2-Amino-3-cyclohexylpropanoyl}-N-Benzylamide FAB+ MS: (M+H)+=857. Amino Acid Anal: Lys (0.95), Pro (1.04), Cha (1.93), Phe (1.01).

EXAMPLE 28

Hydrocinnamoyl-Lysyl-Prolyl-{(2R)-2-Amino-3-cyclohexylpropanoyl}-Phenylalanyl-DArginyl-OH

FAB+ MS: (M+H)+=832.

EXAMPLE 29

(N-Methyl)Phenylalanyl-Lysyl-Prolyl-{(2R)-2-Amino-3-cyclohexylpropanoyl}-{(2S)-2-Amino-3-cyclohexylpropanoyl}-N-Methyl-N-benzylamide FAB+ MS: (M+H)+=814 Amino Acid Anal: MePhe (0.78), Lys (0.96), Pro (1.04), Cha (1.88).

EXAMPLE 30

(N-Methyl)Phenylalanyl-Lysyl-Prolyl-{(2R)-2-Amino-3-cyclohexylpropanoyl}-{(2S)-2-Amino-3-cyclohexylpropanoyl}-N-(5-Aminopentyl)amide The compound was prepared in analogy to Example 19.

FAB+ MS: (M+H)+=795 Amino Acid Anal: MePhe (0.90), Cha (1.86), Lys (0.99), Pro (1.01).

EXAMPLE 31

(4-Phenylbutyryl)-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+=852 Amino Acid Anal: Lys (0.96), Pro (0.92), Cha (1.91), Arg (1.04).

EXAMPLE 32

Hydrocinnamoyl-Lysyl-Prolyl-{(2R)-2-Amino-3-cyclohexylpropanoyl}-{(2S)-2-Amino-3-cyclohexylpropanoyl}-DPhenylalanyl-OH This compound is prepared using the techniques described in Examples 1 and 2. Boc-DPhenylalanyl-OResin is used instead of Boc-DArginyl(N-guanidino-Tos)-OResin.

EXAMPLE 33

3-(4-Hydroxyphenyl)propionyl-Lysyl-Prolyl-{(2R)-2-Amino-3-cyclohexylpropanoyl}-Phenylalanyl-DArginyl-OH FAB+ MS: (M+H)+ =848 Amino Acid Anal: Arg (0.99), Lys (0.99), Pro (1.01), Cha (0.96), Phe (1.02).

EXAMPLE 34

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(2R/S)-2-(Phenyl)butyl}amide The compound was prepared in analogy to Example 21.

FAB+ MS: (M+H)+ =842 Amino Acid Anal: MePhe (1.02), Lys (0.99), Pro (1.07), Cha (1.92).

EXAMPLE 35

(N-Methyl)Phenylalanyl-Lysyl-Prolyl-{(2R)-2-Amino-3-cyclohexylpropanoyl}-N-{(1S)-1-Cyclohexylmethyl-2-[N-(4-Guanidinobutyryl)amido]ethyl}amide N-Boc-(1S)-cyclohexylmethyl ethylenediamine (100 mg, 0.4 mmole) prepared in Example 98, was reacted with N-Cbz-4-aminobutyric acid (92 mg, 0.4 mmole) via the EDC and HOBT method as exemplified in Example 3 to obtain (1-N-Boc-amino)-N′-Cbz-aminobutyryl-3-cyclohexylpropylamide (MS: (M+H)+ =823) in quantitative yield. The Boc group was removed, followed by coupling with Example 3 (295 mg, 0.4 mmole) using the EDC and HOBT method and was then hydrogenated to yield the corresponding amine in 91% yield. It was then guanidinated and treated in the same manner as described in Example 42 to afford the title compound (145 mg, 32%).

FAB+ MS: (M+H)+ =823. Amino Acid Anal: MePhe (1.06), Lys (1.00), Pro (1.00), Cha (0.96).

EXAMPLE 36

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Naphthyl)amide FAB+ MS: (M+H)+ =836. Amino Acid Anal: MePhe (0.91), Lys (0.96), Pro (1.04), Cha (1.82).

EXAMPLE 37

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Naphthylmethyl)amide FAB+ MS: (M+H)+ =850. Amino Acid Anal: MePhe (0.89), Lys (0.92), Pro (1.08), Cha (1.80).

EXAMPLE 38

(N-Methyl)Phenylalanyl-Lysyl-Prolyl-{(2R)-2-Amino-3-cyclohexylpropanoyl}-Phenylalanyl-N-{(3-Carboxy)benzyl}amide FAB+ MS: (M+H)+ =838. Amino Acid Anal: Lys (0.95), Pro (1 01), Cha (0.90), Phe (1.05), MePhe (0.73).

EXAMPLE 39

[N-{3-Phenylpropyl}]Lysyl-Prolyl-{(2R)-2-Amino-3-cyclohexylpropanoyl}-Phenylalanyl-DArginyl-OH H-Lysyl(N-epsilon-Cbz)-Prolyl-{(2R)-2-Amino-3-cyclohexylpropanoyl}-{(2S)-2-Amino-3-cyclohexylpropanoyl}-DArginyl(guanidino-Tos)-OResin, prepared in Example 70 (0.5 g, 0.52 meq./g, 0.26 mmole) was treated with hydrocinnamaldehyde (34.2 μL, 0.26 mmole) and NaCNBH3 (49 mg, 0.78 mmole) in 10 mL of 1% acetic acid in DMF. The reaction was carried out for 3 hours and the peptide resin obtained was treated by the procedures described in Example 70 to afford the title compound (27.8 mg).

FAB+ MS: (M+H)+ =818. Amino Acid Anal: Pro (0.99), Cha (0.97), Phe (0.99), Arg (1.03).

EXAMPLE 40

(N-Methyl)Phenylalanyl-Lysyl-Prolyl-{(2R)-2-Amino-3-cyclohexylpropanoyl}-{(2R)-2-Amino-3-cyclohexylpropanoyl}-N-(3-Guanidinopropyl)-N-(2-Phenethyl)amide The compound was prepared in analogy to Example 42.

FAB+ MS: (M+H)+ =913 Amino Acid Anal: MePhe (0.74), Lys (0.97), Pro (1.03), Cha (1.84).

EXAMPLE 41

(1-Naphthyl)acetyl-Lysyl-Prolyl-{(2R)-2-Amino-3-cyclohexylpropanoyl-}-Phenylalanyl-DArginyl-OH FAB+ MS: (M+H)+ =868. Amino Acid Anal: Lys (0.98), Pro (1.02), Cha (0.94), Phe (0.98), Arg (1.04).

EXAMPLE 42

(N-Methyl)Phenylalanyl-Lysyl-Prolyl-{(2R)-2-Amino-3-cyclohexylpropanoyl}-{(2S)-2-Amino-3-cyclohexylpropanoyl}-N-(5-Guanidinopentyl)amide Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropanoyl}-1,5-Diaminopentane monoamide was prepared in analogy to Example 19. The guanidination of the above compound (220 mg, 0.22 mmole) was carried out according to the literature method: Salvadori, S.; Sarto, G. P.; Tomatis, R.; Eur. J. Med. Chem. Chim. Ther., 1983, 18, 489. The fully protected peptide was treated with 50% trifluoroacetic acid in methylene chloride, and then purified by RP-HPLC to afford the title compound (39 mg) in 21% overall yield.

FAB+ MS: (M+H)+ =837. Amino Acid Anal: MePhe (0.82), Lys (1.00), Pro (1.00), Cha (1.80).

EXAMPLE 43

(N-Methyl)Phenylalanyl-Lysyl-Prolyl-{(2R)-2-Amino-3-cyclohexylpropanoyl}-{(2S)-2-Amino-3-cyclohexylpropanoyl}-N-(6-Aminohexyl)amide The compound was prepared in analogy to Example 19.

FAB+ MS: (M+H)+ =809. Amino Acid Anal: MePhe (0.78), Cha (1.84), Lys (0.98), Pro (1.02).

EXAMPLE 44

{R(−)-3-Phenylbutyryl}-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =852. Amino Acid Anal: Lys (0.98), Pro (1 15), Cha (1.90), Arg (1.02).

EXAMPLE 45

4-Hydroxyphenylacetyl-Lysyl-Prolyl-{(2R)-2-Amino-3-cyclohexylpropanoyl}-Phenylalanyl-DArginyl-OH FAB+ MS: (M+H)+ =834. Amino Acid Anal: Arg (0.99), Lys (0.98), Pro (1.00), Cha (0.95), Phe (1.02).

EXAMPLE 46

(N-Methyl)Phenylalanyl-Lysyl-Prolyl-{(2R)-2-Amino-3-cyclohexylpropanoyl}-N-[(1'S)-1-{(5RS)-5-ethyl-5-cyclohexyloxazolin-2-yl}-2-phenethyl]amide The compound (18 mg) was isolated as a side product of Example 184.

FAB+ MS: (M+H)+ =840. Amino Acid Anal.: MePhe (1.00), Lys (0.99), Pro (0.99), Cha (0.98), Phe (1.02).

EXAMPLE 47

{(2-Benzyl-2-cyano-3-phenyl)propionyl}-Lysyl-Prolyl-{(2R)-2-Amino-3-cyclohexylpropanoyl}-{(2S)-2-Amino-3-cyclohexylpropanoyl}-DArginyl-OH Ethyl cyanoacetate (15.0 g, 0.133 mol) was dialkylated with benzyl bromide employing 1,8-diazabicyclo[5.4.0]undecene-7 as described by: Ono, N.; Yoshimura, T.; Tanikaga, R.; Kaji, A. Chem. Lett. 1977, 871–872. The obtained ethyl 2-benzyl-2-cyano-3-phenylpropionate (80% yield) was identical with the material described in Example 88. The ester was saponified to the corresponding carboxylic acid as previously described in Example 88. The title peptide was prepared under standard solid phase peptide conditions as exemplified in Examples 1 and 2.

FAB+ MS: (M+H)+ =953.

EXAMPLE 48

(N-Methyl)Phenylalanyl-Lysyl-Prolyl-{(2R)-2-Amino-3-cyclohexylpropanoyl}-{(2S)-2-Amino-3-cyclohexylpropanoyl}-{(R)-(−)-2-Amino-3-phenyl-1-propanol)}

The compound was prepared in analogy to Example 119.

FAB+ MS: (M+H)+ =844. Amino Acid Anal: MePhe (0.92), Lys (0.95), Pro (1.05), Cha (1.80).

EXAMPLE 49

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Naphthyl)methylamide FAB+ MS: (M+H)+ =850. Amino Acid Anal: MePhe (0.92), Lys (0.91), Pro (1.09), Cha (1.80).

EXAMPLE 50

(N-Methyl)Phenylalanyl-Lysyl-Prolyl-{(2R)-2-Amino-3-cyclohexylpropanoyl}-Phenylalanyl-N-(4-Benzenesulfonamide)methylamide FAB+ MS: (M+H)+ =873. Amino Acid Anal: Lys (0.96), Pro (1.00), Cha (0.99), Phe (1.04), MePhe (0.74).

EXAMPLE 51

{(R/S)-3-Amino-3-phenylpropionyl}-Lysyl-Prolyl-{(2R)-2-Amino-3-cyclohexylpropanoyl)-Phenylalanyl-DArginyl-OH Commercially available DL-3-amino-3-phenylpropionic acid (5.0 g, 30.3 mmole) was reacted with Boc-ON [2-(tertbutoxycarbonyloxyimino)-2-phenylacetonitrile](8.94 g, 36.36 mmole) in 50 mL of dioxane/water (1:1) and triethylamine (6.33 mL, 45.45 mmole) to obtain N-Boc-DL-3-amino-3-phenylpropionic acid (5.61 g) in 69.9% yield. This was used to construct the peptide using the Merrified resin described in Example 1 to obtain the title compound. The isomers were separated by RP-HPLC.

FAB+ MS: (M+H)+ =847. Amino Acid Anal: Lys (0.94), Pro (1.02), Cha (1.00), Phe (1.00), Arg (1.04).

EXAMPLE 52

{(R/S)-3-Amino-3-phenylpropionyl}-Lysyl-Prolyl-{(2R)-2-Amino-3-cyclohexylpropanoyl}-Phenylalanyl-DArginyl-OH This compound was one of the isomers of Example 51.

FAB+ MS: (M+H)+ =847. Amino Acid Anal: Lys (0.97), Pro (1.01), Cha (0.99), Phe (1.00), Arg (1.02).

EXAMPLE 53

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Guanidinopropyl)-N-(2-Phenethyl)amide The compound was prepared in analogy to Example 42.

FAB+ MS: (M+H)+ =913. Amino Acid Anal: MePhe (0.82), Lys (0.95), Pro (1.05), Cha (1.92).

EXAMPLE 54

2-Naphthylacetyl-Lysyl-Prolyl-{(2R)-2-Amino-3-cyclohexylpropanoyl}-Phenylalanyl-DArginyl-OH FAB+ MS: (M+H)+ =868. Amino Acid Anal: Lys (0.96), Pro (0.98), Cha (0.97), Phe (1.05), Arg (1.01).

EXAMPLE 55

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Guanidinopropyl)amide The compound was prepared in analogy to Example 42.

FAB+ MS: (M+H)+ =809. Amino Acid Anal: MePhe (0.82), Lys (0.99), Pro (1.01), Cha (1.73).

EXAMPLE 56

(N-Methyl)Phenylalanyl-Lysyl-Prolyl-{(2R)-2-Amino-3-cyclohexylpropanoyl}-{(2S)-2-Amino-3-cyclohexylpropanoyl}-N-(7-Aminoheptyl)amide The compound was prepared in analogy to Example 19.

FAB+ MS: (M+H)+ =823. Amino Acid Anal: MePhe (0.80), Cha (1.84), Lys (0.99), Pro (1.01).

EXAMPLE 57

{S(+)-3-Phenylbutyryl}-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =852. Amino Acid Anal: Lys (0.93), Pro (1.14), Cha (1.99), Arg (1.07).

EXAMPLE 58

(N-Methyl)Phenylalanyl-Lysyl-Prolyl-{(2R)-2-Amino-3-cyclohexylpropanoyl}-Phenylalanyl-(2-Methyl)benzyl ester FAB+ MS: (M+H)+ =809. Amino Acid Anal: MePhe (1.01), Lys (0.92), Pro (1.06), Cha (0.93), Phe (1.02).

EXAMPLE 59

(N-Methyl)Phenylalanyl-Lysyl-Prolyl-{(2R)-2-Amino-3-cyclohexylpropanoyl}-N-[(1′S)-1-{(5RS)-5-ethyl-5-cyclohexyloxazolin-2-yl}-2-cyclohexylethyl]amide The compound (32 mg) was isolated as a side product of Example 184.

FAB+ MS: (M+H)+ =846. Amino Acid Anal: MePhe (1.00), Lys (0.99), Pro (1.01), Cha (1.91).

EXAMPLE 60

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1RS)-(1-Benzyl)-4-phenylbutyl}amide 4-Phenylbutylalcohol (5.0 g, 33.3 mmole) was oxidized by the literature method; Parikh, J. R.; Doering, W. E.; J. Am. Chem. Soc., 1967, 89, 5505. The aldehyde obtained was reacted with benzylmagnesium chloride (35 mL of 1M ether solution, 35 mmole) at −12° C. for 20 minutes with stirring. The reaction was quenched by 1M phosphoric acid solution and ether was added. The ethereal solution was washed with saturated sodium bicarbonate solution, brine, dried over sodium sulfate and concentrated at reduced pressure to afford (dl)-2-hydroxy-1,5-diphenylpentane (600 mg, 8%). (MS: (M+NH4)+ =258). This material (588 mg, 2.4 mmole) was mesylated, treated with sodium azide (636 mg, 9.6 mmole) and then reduced to obtain the corresponding amine (500 mg) in 94% yield, according to the method described in Example 98 (MS: (M+H)+ =240). Example 5 (63 mg, 0.1 mmole) was used to react with the above amine (20 mg, 0.1 mmole) using the EDC and HOBT coupling method. After deprotection and purification, the title compound (37 mg) was obtained in 38% yield.

FAB+ MS: (M+H)+ =932. Amino Acid Anal: MePhe (0.96), Lys (1.01), Pro (0.99), Cha (1.86).

EXAMPLE 61

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Hydroxybutyl)amide FAB+ MS: (M+H)+ =782. Amino Acid Anal: MePhe (0.94), Lys (0.98), Pro (1.02), Cha (1.83).

EXAMPLE 62

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1R/S)-1-Benzyl-4-guanidinobutyl}amide N-Cbz-n-Aminovaleric acid (8.0 g, 31.8 mmole) was dissolved in 120 mL of dioxane and 125 mL of isobutylene, and 5 mL of concentrated sulfuric acid was added as a catalyst to yield N-Cbz-n-aminovaleric acid t-butyl ester (8.5 g, 87%). The t-butyl ester (2.0 g, 6.5 mmole) was treated with lithium bis(trimethylsily)amide (16.3 mL, 16.3 mmole, 1M THF solution) in 40 mL of THF at −78° C. After allowing the reaction mixture to warm to 0° C., the reaction mixture was stirred for 40 minutes, and then benzyl bromide (0.77 mL, 6.5 mmole) in 2 mL of THF was added. After stirring at 0° C. for 1 hour, the mixture was quenched by the addition of 1M phosphoric acid and ethyl acetate was added. After the usual work up, evaporation of the solvent gave 832 mg (32%) of butyl 2-benzyl-5-Cbz-aminovalerate (MS: (M+H)+ =398).

The t-butyl ester of the compound (1.0 g, 2.5 mmole) was cleaved and converted to the amine by the literature method: Plattner, J. J. et. al., J. Med. Chem., 1988, 31, 2277. The corresponding amine was isolated as a trimethylsilylethylcarbamate (350 mg) (MS: (M+H)+ =457) in 35% yield. The trimethylsilyl group was cleaved by tetra-n-butylammonium fluoride in quantitative yield. 1-Benzyl-4-Cbz-diaminobutane (MS: (M+H)+ =313) was isolated as a dl mixture.

This was coupled with Example 5, followed by the deprotection of the Cbz group and guanidination as has been previously described in Example 42. The isomers were separated by RP-HPLC.

FAB+ MS: (M+H)+ =913. Amino Acid Anal: MePhe (0.75), Lys (1.01), Pro (0.99), Cha (1.84).

EXAMPLE 63

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(4-Benzenesulfonamide)methyl}amide FAB+ MS: (M+H)+ =879. Amino Acid Anal: Lys (0.99), Pro (1.01), Cha (1.96), MePhe (0.73).

EXAMPLE 64

{(R/S)-3-N-Methylamino-3-phenylpropionyl}-Lysyl-Prolyl-{(2R)-2-Amino-3-cyclohexylpropanoyl}-Phenylalanyl-DArginyl-OH Example 51 (N-Boc-DL-3-amino-3-phenylpropionic acid (1.325 g, 5 mmole) was N-methylated by methyl iodide and sodium hydride as described in the literatures; Lovett, J. A.; Portoghese, P. J. Med. Chem. 1987, 30, 1144; Cheung, S. T. Benoiton, N. L. Can. J. Chem., 1977, 55, 906. Proton NMR (CDCL3) δ=1.48 (s, 9H), 2.65(br.s. 3H), 2.88–3.04(m, 2H), 5.73(br. 1H), 7.26–7.37(m, 5H). This was used to prepare the title compound according to the methods described in Examples 1 and 2. The isomers were separated by RP-HPLC.

FAB+ MS: (M+H)+ =861. Amino Acid Anal: Lys (0.96), Pro (0.91), Cha (1.03), Phe (0.98), Arg (1.06).

EXAMPLE 65

{(R/S)-3-N-Methylamino-3-phenylpropionyl}-Lysyl-Prolyl-{(2R)-2-Amino-3-cyclohexylpropanoyl}-Phenylalanyl-DArginyl-OH The compound was one of the isomers of Example 64.

FAB+ MS: (M+H)+ =861. Amino Acid Anal.: Lys (0.97), Pro (1.10), Cha (0.99), Phe (1.00), Arg (1.03).

EXAMPLE 66

N-(4-Guanidinobutyryl)-N-[(N-Methyl)Phenylalanyl-Lysyl-Prolyl-{(2R)-2-Amino-3-cyclohexylpropanoyl}-{(2S)-2-Amino-3-cyclohexylpropyl}]-N-(2-Phenethyl)amine Boc-(2S)-2-Amino-3-cyclohexylpropanoic acid (1.0 g, 3.7 mmole) was coupled with 2-phenethylamine (0.51 g, 4.1 mmole) using EDC (1.06 g, 5.6 mmole) and HOBT (0.55 g, 4.1 mmole) in methylene chloride to yield Boc-(2S)-2-Amino-3-cyclohexylpropanoyl-2-phenethylamide (MS: (M+H)+ =375) in quantitative yield. All of the material obtained was dissolved in 20 mL of THF and cooled in an ice bath. Borane-THF (11.1 mL of 1M solution, 11.1 mmole) was then carefully added to the reaction mixture. After the addition was over, the cooling bath was removed and the reaction was maintained at room temperature for one overnight with stirring. Methanol was added to the reaction mixture and the solvent was removed. The residue was dissolved in diethylether and the pH was adjusted to 6.0 using 1M hydrochloric acid. The etheral solution was washed with brine, dried over sodium sulfate, and concentrated in vacuo. The solid obtained (1.5 g) was recrystallized from ether/n-hexane to yield 240 mg (18%) of N-[Boc-(2S)-2-Amino-3-cyclohexylpropyl]-N-(2-phenethyl)amine hydrochloride salt (HCl). (MS: $(M+H)^+ = 361$).

The product obtained (228 mg, 0.6 mmole) was reacted with N-Cbz-4-aminobutyric acid (158 mg, 0.6 mmole) in the presence of EDC (182 mg, 0.9 mmole), HOBT (94 mg, 0.7 mmole) and NMM (80 µL, 0.7 mmole) in methylene chloride to obtain N-[Boc-(2S)-2-Amino-3-cyclohexylpropyl]-N-(N-Cbz-4-aminobutyryl)}-N-(2-phenethyl)amine in quantitative yield. Half of the above compound (0.3 mmole) was treated with 4N hydrochloric acid in dioxane, followed by coupling with Boc-(N-Methyl)Phenylalanyl-Lysyl(N-epsilon-Boc)-Prolyl-{(2R)-2-Amino-3-cyclohexylpropanoyl}-OH (Example 3) via the EDC and HOBT coupling method as described (Example 3) in 75% yield (270 mg) (MS: $(M+H)^+ = 1219$). The Cbz-group of the compound (250 mg) was cleaved by catalytic hydrogenolysis by the literature method; Ram, S.; Ehrenkaufer, R. E.; Synthesis, 1988, 2, 91, and then guanidination was carried out. The title compound (54.5 mg, 21%) was obtained after deprotection and purification.

FAB+ MS: $(M+H)^+ = 927$. Amino Acid Anal: MePhe (0.87), Lys (0.96), Pro (1.04), Cha (0.85).

EXAMPLE 67

1-Naphthoxyacetyl-Lysyl-Prolyl-{(2R) 2-Amino-3-cyclohexylpropanoyl}-Phenylalanyl-DArginyl-OH FAB+ MS: $(M+H)^+ = 884$. Amino Acid Anal: Lys (0.98), Pro (0.95), Cha (0.96), Phe (0.99), Arg (1.03).

EXAMPLE 68

[2-{(R)-(−)-Methoxy}-2-phenylacetyl]-Lysyl-Prolyl-{(2R)-2-Amino-3-cyclohexylpropanoyl}-Phenylalanyl-DArginyl-OH FAB+ MS: $(M+H)^+ = 848$. Amino Acid Anal: Lys (0.99), Pro (0.85), Cha (0.92), Phe (1.00), Arg (1.02).

EXAMPLE 69

[2-{(S)-(+)-Methoxy}-2-phenylacetyl]-Lysyl-Prolyl-{(2R)-2-Amino-3-cyclohexylpropanoyl}-Phenylalanyl-DArginyl-OH FAB+ MS: $(M+H)^+ = 848$. Amino Acid Anal: Lys (0.96), Pro (1.07), Cha (0.89), Phe (1.03), Arg (1.01).

EXAMPLE 70

N-Phenylacetyl-Lysyl-Prolyl-{(2R)-2-Amino-3-cyclohexylpropanoyl}-{(2S)-2-Amino-3-cyclohexylpropanoyl}-DArginyl-OH The trifluoroacetic acid salt of Lysyl(N-epsilon-Cbz)Prolyl-{(2R)-2-Amino-3-cyclohexylpropanoyl}-{(2S)-2-Amino-3-cyclohexylpropanoyl}-DArginyl(-guanidino-Tos)-OResin (0.60 g) was prepared in accordance with the procedure described in Example 1. After the sequence was stopped at Agenda A-step 2, 10% DIPEA in methylene chloride (15 mL) was introduced into the reaction vessel, followed by phenylacetyl chloride (0.5 mL, 3.8 mmole). The reaction was allowed to proceed at room temperature for 30 min. After the resin obtained was washed with methylene chloride (5×10 mL), the protected peptide resin was treated with HF, lyophilized (83.9 mg) and purified (60.0 mg) in accordance with the procedure described in Example 2 to afford 16.8 mg of the title compound.

FAB+ MS: $(M+H)^+ = 824$. Amino Acid Anal: Lys (1.02), Pro (0.82), Cha (1.99), Arg (1.03).

EXAMPLE 71

Hydrocinnamoyl-Lysyl-Prolyl-{(2R)-2-Amino-3-cyclohexylpropanoyl}-{(2S)-2-Amino-3-cyclohexylpropanoyl}-DArginyl-OH FAB+ MS: $(M+H)^+ = 838$. Amino Acid Anal: Lys (0.96), Pro (1.12), Cha (1.89), Arg (1.04).

EXAMPLE 72

(N-Methyl)Phenylalanyl-Lysyl-Prolyl-{(2R)-2-Amino-3-cyclohexylpropanoyl}-Phenylalanyl-Benzyl ester FAB+ MS: $(M+H)^+ = 795$. Amino Acid Anal: MePhe (1.05), Lys (0.95), Pro (1.00), Cha (0.96), Phe (1.04).

EXAMPLE 73

3-{(3S)-Benzyl}-6-{(6R)-(3′-Guanidino)propyl}-4-[(N-Methyl)Phenylalanyl-Lysyl-Prolyl-{(2S)-2-Amino-3-cyclohexylpropanoyl}]-Piperazine-2-one The compound was prepared in analogy to Example 10.

FAB+ MS: $(M+H)^+ = 829$. Amino Acid Anal: MePhe (1.03), Lys (0.99), Pro (1.01), Cha (0.94).

EXAMPLE 74

(N-Methyl)Phenylalanyl-Lysyl-Prolyl-{(2R)-2-Amino-3-cyclohexylpropanoyl}-N-{(1RS)-(1-Benzyl)-4-phenylbutyl}amide The compound was prepared in analogy to Example 60.

FAB+ MS: $(M+H)^+ = 779$. Amino Acid Anal: MePhe (1.01), Lys (0.98), Pro (1.02), Cha (0.88).

EXAMPLE 75

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1-Phenyl)cyclopropylmethyl}amide FAB+ MS: $(M+H)^+ = 836$. Amino Acid Anal: MePhe (0.96), Lys (0.97), Pro (1.03), Cha (1.83).

EXAMPLE 76

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1R/S)-1-Benzyl-4-guanidinobutyl}amide The compound was one of the isomer of Example 62.

FAB+ MS: $(M+H)^+ = 913$. Amino Acid Anal: MePhe (0.75), Lys (0.98), Pro (1.02), Cha (1.68).

EXAMPLE 77

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(4-N,N-Dimethylamino)benzyl}amide FAB+ MS: $(M+H)^+ = 843$. Amino Acid Anal: Lys (0.96), Pro (1.04), Cha (1.90), MePhe (0.85).

EXAMPLE 78

N-(4-Guanidinobutyl)-N-[(N-Methyl)Phenylalanyl-Lysyl-Prolyl-{(2R)-2-Amino-3-cyclohexylpropanoyl}-{(2S)-2-Amino-3-cyclohexylpropyl}]-N-Phenylacetamide Boc-(2S)-2-Amino-3-cyclohexylpropanol (1.16 g, 4.4 mmole) was converted to its aldehyde by the literature method: (Mancuso, A. J.; Huang, S-L.; Swern, D.; J. Org. Chem. 1978, 43, 2480) in 97% yield. The aldehyde (1.11 g, 4.4 mmole) was subjected to reductive amination with mono-Cbz-1,4-diaminobutane (1.0 g, 4.4 mmole) using sodium cyanoborohydride (NaCNBH$_3$, 350 mg, 5.5 mmole) in acetic acid (0.54 mL, 9.2 mmole), methanol (20 mL) and isopropanol.

N-{Boc-(2S)-2-Amino-3-cyclohexylpropyl}-N-{4-(Cbz-amino)butyl}amine (700 mg) was obtained in 35% yield.(MS: (M+H)+ =462). This material (400 mg, 0.9 mmole) was reacted with phenylacetyl chloride (0.14 mL, 1.1 mmole) in the presence of N,N-dimethylaminopyridine (DMAP, 11 mg, 0.09 mmole) and triethylamine (TEA) (0.15 mL, 1.1 mmole) in methylene chloride to obtain N-{Boc-(2S)-2-Amino-3-cyclohexylpropyl}-N-Phenylacetyl-N-{(N-4-Cbz-Amino)butyl}amine in quantitative yield. The following procedures: deprotection of Boc-group; coupling with tetrapeptide (Example 3); deprotection of Cbz-group; and guanidination; were carried out by the methods described in Example 66.

FAB+ MS: (M+H)+ =927. Amino Acid Anal: MePhe (0.78), Lys (1.00), Pro (1.00), Cha (0.85).

EXAMPLE 79

N-(4-Guanidinobutyl)-N-[(N-Methyl)Phenylalanyl-Lysyl-Prolyl-{(2R)-2-Amino-3-cyclohexylpropanoyl}-{(2S)-2-Amino-3-cyclohexylpropyl}]-N-2-Phenethylamine N-(N-Cbz-4-Aminobutyl)-2-phenethylamide was prepared in analogy to Example 66 (i.e. EDC and HOBT coupling and borane reduction). N-(N-Cbz-4-Aminobutyl)-2-phenethylamide hydrochloride salt (800 mg, 2.2 mmole) was reacted with Boc-{(2S)-2-Amino-3-cyclohexylpropanoyl}-OH (600 mg, 2.2 mmole), followed by reduction with borane-THF as described in Example 66 to yield N-[Boc-{(2S)-2-Amino-3-cyclohexylpropyl}]-N-{(N-Cbz-4-Amino)butyl}-N-2-Phenethylamine (320 mg, 26%) (MS: (M+H)+ =566). The title compound was obtained by the method described in Example 66.

FAB+ MS: (M+H)+ =913. Amino Acid Anal: MePhe (0.75), Lys (0.96), Pro (1.04), Cha (0.77).

EXAMPLE 80

2-Naphthoxyacetyl-Lysyl-Prolyl-{(2R)-2-Amino-3-cyclohexylpropanoyl}-Phenylalanyl-DArginyl-OH FAB+ MS: (M+H)+ =884. Amino Acid Anal: Lys (0.97), Pro (1 01), Cha (0.97), Phe (0.99), Arg (1.04).

EXAMPLE 81

{(1-Phenylcyclopropyl)carbonyl}-Lysyl-Prolyl-{(2R)-2-Amino-3-cyclohexylpropanoyl}-Phenylalanyl-DArginyl-OH FAB+ MS: (M+H)+ =844. Amino Acid Anal: Lys (0.94), Pro (1.09), Cha (0.90), Phe (1.03), Arg (1.03).

EXAMPLE 82

N-Benzoyl-Lysyl-Prolyl-{(2R)-2-Amino-3-cyclohexylpropanoyl}-{(2S)-2-Amino-3-cyclohexylpropanoyl}-DArginyl-OH FAB+ MS: (M+H)+ =810. Amino Acid Anal: Lys (1.01), Pro (0.97), Cha (1.99), Arg (1.03).

EXAMPLE 83

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Guanidinobutyl)amide Boc-Agmatine(guanidino-Tos) (187.8 mg, 0.49 mmole) was treated with 2.5 mL of 4N hydrochloric acid in dioxane for 1 hour at room temperature. The hydrochloride salt obtained was reacted with Boc-(N-Methyl)Phenylalanyl-Lysyl (N-epsilon-Boc)-Prolyl-{(2R)-2-Amino-3-cyclohexylpropanoyl}-{(2S)-2-Amino-3-cyclohexylpropanoyl}-OH (Example 5) (446 mg, 0.49 mmole) in the presence of 1-(3-dimethylaminopropyl)-3-ethylcarbodiimide hydrochloride (EDC) (100 mg, 0.5 mmole), 1-hydroxybenzotriazole monohydrate (HOBT) (70 mg, 0.5 mmole) and N-methylmorpholine (NMM) (60 μL, 0.5 mmole) in methylene chloride. After treatment as described in Example 116, the fully protected peptide (in quantitative yield) was treated with trifluoromethanesulfonic acid (triflic acid) (3 mL) and anisole (0.15 mL). The triflate salt was displaced by an acetate salt using an ionic exchange resin (Amberlite IRA-410) and was then purified by RP-HPLC. The title compound was obtained in 38% yield.

FAB+ MS: (M+H)+ =823. Amino Acid Anal: MePhe (0.78), Cha (1.80), Lys (0.97), Pro (1.03).

EXAMPLE 84

{(3S)-Phenyllactyl)-Lysyl-Prolyl-{(2R)-2-Amino-3-cyclohexylpropanoyl}-Phenylalanyl-DArginyl-OH Commercially available L-3-phenyllactic acid (24.9 mg, 0.15 mmole) was suspended in 5 mL of methylene chloride in an ice bath. N-hydroxysuccinimide (17.3 mg, 0.15 mmole), followed by N,N'-dicyclohexylcarbodiimide (DCC) (30.9 mg, 0.15 mmole) were added. After stirring at 0° C. for 1 hour, the insoluble material was removed by filtration. The filtrate was added to 2 mL of methylene chloride containing Lysyl(N-epsilon-Cbz)-Prolyl-{(2R)-2-Amino-3-cyclohexylpropanoyl}-Phenylalanyl-DArginyl(guanidino-Tos)-OBenzyl (121 mg, 0.1 mmole) and NMM (11 μL, 0.1 mmole). The reaction was stirred at 0° C. for 1 hour and at room temperature for 2 days. Ethyl acetate (30 mL) was added and the solution was washed with brine, 10% potassium hydrogen sulfate, brine, and dried over magnesium sulfate. The solvent was removed under reduced pressure to afford the crude peptide which was treated in the same method described in Example 116. From half of the crude peptide, 22.5 mg of pure title compound was obtained.

FAB+ MS: (M+H)+ =848. Amino Acid Anal: Arg (1.00), Lys (0.97), Pro (1.01), Cha (0.96), Phe (0.99).

EXAMPLE 85

3-{(3R)-Benzyl}-6-{(6R)-(3-Guanidino)propyl}-4-[(N-Methyl)Phenylalanyl-Lysyl-Prolyl-{(2S)-2-Amino-3-cyclohexylpropanoyl}]-Piperazine-2-one The compound was prepared in analogy to Example 10.

FAB+ MS: (M+H)+ =829. Amino Acid Anal: MePhe (1.06), Lys (0.98), Pro (1.02), Cha (0.96).

EXAMPLE 86

2-Cyanocinnamoyl-Lysyl-Prolyl-{(2R)-2-Amino-3-cyclohexylpropanoyl}-Phenylalanyl-DArginyl-OH The title compound was prepared under standard solid phase conditions described in Examples 1 and 2 using commercially available alpha-cyanocinnamic acid.

FAB+ MS: (M+H)+ =861.

EXAMPLE 87

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Indan)amide FAB+ MS: (M+H)+ =826. Amino Acid Anal.: MePhe (0.86), Lys (0.96), Pro (1.03), Cha (1.93).

EXAMPLE 88

{2-Benzyl-2-cyano-3-phenylpropionyl}-Lysyl-Prolyl-{(2R)-2-Amino-3-cyclohexylpropanoyl}-Phenylalanyl-DArginyl-OH Sodium ethoxide was prepared by the slow addition of sodium (1.17 g, 50.8 mmol) to ethanol (200 mL). Upon cooling to ambient temperature, ethyl cyanoacetate (5.00 g, 44.2 mmol) was added, and the mixture was stirred for 1 h. Subsequently, benzyl bromide (6.30 mL, 53.0 mmol) was introduced and stirring of the reaction mixture was continued overnight. The mixture was quenched with saturated aqueous ammonium chloride solution, and the volatiles were removed under reduced pressure. The residue was partitioned between water (500 mL) and ethyl acetate (250 mL). The aqueous layer was further extracted with ethyl acetate (2×250 mL), and the combined organic layers were dried over sodium sulfate and freed of solvent. Ethyl 2-benzyl-2-cyano-3-phenylpropionate was separated from recovered starting material and monoalkylated material with a Waters Prep 500A HPLC employing 2 silica gel cartridges and 10% ethyl acetate/hexane as the eluent. Yield: 5.80 g (19.8 mmol, 45%). $^1$H NMR (CDCl$_3$, 300 MHz) δ 7.32 (br s, 10 H), 4.00 (qd, J=1, 7.5 Hz, 2 H), 3.22 (dd, J=13.5, 64.5 Hz, 4 H), 0.98 (td, J=1, 7.5 Hz, 3 H).

Ethyl 2-benzyl-2-cyano-3-phenylpropionate (3.20 g, 11 mmol) was saponified at room temperature overnight with potassium hydroxide (6.17 g, 0.11 mol) in 10% water/ethanol. The mixture was diluted with water (200 mL) and extracted with hexane (2×50 mL). The aqueous layer was acidified with 1M phosphoric acid and extracted with methylene chloride (4×100 mL). The combined organic extracts were dried over magnesium sulfate and freed of solvent to afford 2-benzyl-2-cyano-3-phenylpropionic acid (2.94 g, 11 mmol) as a colorless solid: $^1$H NMR (CDCl$_3$, 300 MHz) δ 7.34 (br s, 10 H), 3.24 (dd, J=13.5, 57 Hz); mass spectrum m/e 283 (M+NH$_4$+).

The title peptide was prepared under the standard protocol described in Examples 1 and 2, except 2-benzyl-2-cyano-3-phenylpropionic acid was incorporated with the assistance of an equivalent weight of 1-hydroxybenzotriazole. FAB+ MS: (M+H)+ =947 Amino Acid Anal: Phe (0.94), Cha (0.95), Lys (1.04), Arg (1.01), Pro (1.00).

EXAMPLE 89

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(Benzimidazol-2-yl)methyl}amide FAB+ MS: (M+H)+ =840. Amino Acid Anal: Lys (0.96), Pro (1.04), Cha (1.87), MePhe (0.85).

EXAMPLE 90

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Guanidinobutyl)-N-(2-Phenethyl)amide The compound was prepared in analogy to Example 212.

FAB+ MS: (M+H)+ =927. Amino Acid Anal: MePhe (0.76), Lys (0.99), Pro (1.01), Cha (1.79).

EXAMPLE 91

Hydrocinnamoyl-Lysyl-Prolyl-{(2R)-2-Amino-3-cyclohexylpropanoyl}-Phenylalanyl-Ψ(CH$_2$NH)-DArginyl-OH The compound was prepared in analogy to Example 192.

FAB+ MS: (M+H)+ =818.

EXAMPLE 92

Hydrocinnamoyl-Lysyl-Prolyl-{(2R)-2-Amino-3-cyclohexylpropanoyl}-DPhenylalanyl-Ψ(CH$_2$NH)-DArginyl-OH The compound was prepared in analogy to Example 192.

FAB+ MS: (M+H)+ =818. Amino Acid Anal: Lys (1.02), Pro (0.98), Cha (0.98).

EXAMPLE 93

Phenoxyacetyl-Lysyl-Prolyl-{(2R)-2-Amino-3-cyclohexylpropanoyl}-Phenylalanyl-DArginyl-OH FAB+ MS: (M+H)+ =834. Amino Acid Anal: Lys (1.00), Pro (0.91), Cha (0.94), Phe (0.99), Arg (1.02).

EXAMPLE 94

{(1-Phenyl-1-cyclopentane)carbonyl}-Lysyl-Prolyl-{(2R)-2-Amino-3-cyclohexylpropanoyl}-Phenylalanyl-DArginyl-OH FAB+ MS: (M+H)+ =872. Amino Acid Anal: Lys (0.93), Pro (1.14), Cha (0.96), Phe (1.06), Arg (1.01).

EXAMPLE 95

(N-Methyl)Phenylalanyl-Lysyl-Prolyl-{(2R)-2-Amino-3-cyclohexylpropanoyl}-N-(2-Phenethyl)amide FAB+ MS: (M+H)+ =661. Amino Acid Anal: MePhe (0.82), Cha (0.96), Lys (0.99), Pro (1.01).

EXAMPLE 96

(N-Methyl)Phenylalanyl-Lysyl-Prolyl-{(2R)-2-Amino-3-cyclohexylpropanoyl}-{(2S)-2-Amino-3-cyclohexylpropanoyl}-N-Benzylamide FAB+ MS: (M+H)+ =800. Amino Acid Anal: MePhe (0.82), Cha (1.84), Lys (0.97), Pro (1.03).

EXAMPLE 97

(N-Methyl)Phenylalanyl-Lysyl-Prolyl-{(2R)-2-Amino-3-cyclohexylpropanoyl}-Phenylalanyl-{2,2-Dimethyl-2-Phenethyl}amide The compound was prepared in analogy to Example 109.

FAB+ MS: (M+H)+ =836. Amino Acid Anal: MePhe (0.94), Lys (0.96), Pro (0.98), Cha (1.00), Phe (1.07).

EXAMPLE 98

(N-Methyl)Phenylalanyl-Lysyl-Prolyl-{(2R)-2-Amino-3-cyclohexylpropanoyl}-N-{(1S)-1-Cyclohexylmethyl-2-guanidinoethyl}amide The O-Mesyl product of Example 22 was treated with sodium azide (542 mg, 8.4 mmole) in 5 mL of DMF. The azide (550 mg, 2 mmole) was reduced to the amine (MS: (M+H)+ =257) in quantitative yield. The amine (160 mg, 0.6 mmole) was guanidinated, the Boc group was removed, and then the final coupling and deprotection were carried out.

FAB+ MS: (M+H)+ =738. Amino Acid Anal: MePhe (1.41), Lys (0.98), Pro (1 02), Cha (1.22).

EXAMPLE 99

{(2RS)-2-Cyano-3-phenylpropionyl}-Lysyl-Prolyl-{(2R)-2-Amino-3-cyclohexylpropanoyl}-Phenylalanyl-DArginyl-OH (2RS)-Cyano-3-phenylpropionic acid was prepared as described in Example 173. The title peptide was prepared utilizing standard solid phase peptide synthesis techniques described in Example 1. The diastereomeric pair could not be separated by HPLC.

FAB+ MS: (M+H)+ =857.

EXAMPLE 100

(N-Methyl)Phenylalanyl-Lysyl-Prolyl-{(2R)-2-Amino-3-cyclohexylpropanoyl}-Phenylalanyl-N-{(1-Phenyl)-cyclopropylmethyl}amide FAB+ MS: (M+H)+ =834. Amino Acid Anal: MePhe (0.83), Lys (1.00), Pro (0.96), Cha (0.98), Phe (1.05).

The amine (MS: (M+H)+ =257).

EXAMPLE 101

(N-Methyl)Phenylalanyl-Lysyl-Prolyl-{(2R)-2-Amino-3-cyclohexylpropanoyl}-{(2S)-2-Amino-3-cyclohexylpropanoyl}-N-Diphenylmethylamide FAB+ MS: (M+H)+ =876. Amino Acid Anal: MePhe (0.89), Lys (0.92), Pro (1.08), Cha (1.78).

EXAMPLE 102

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Nitrobenzyl)amide FAB+ MS: (M+H)+ =845. Amino Acid Anal: Lys (0.97), Pro (1.03), Cha (1.89), MePhe (0.87).

EXAMPLE 103

(N-Methyl)Phenylalanyl-Lysyl-Prolyl-{(2R)-2-Amino-3-cyclohexylpropanoyl}-{(2R)-2-Amino-3-cyclohexylpropanoyl}-N-(4-Guanidinobutyl)-N-(2-Phenethyl)amide The compound was prepared in analogy to Example 212, except Boc-(2R)-2-Amino-3-cyclohexylpropanoic acid was used instead of Boc-(2S)-2-Amino-3-cyclohexylpropanoic acid.

FAB+ MS: (M+H)+ =927. Amino Acid Anal: MePhe (0.72), Lys (1.03), Pro (0.97), Cha (1.70).

EXAMPLE 104

Hydrocinnamoyl-Lysyl(N-epsilon-nicotyl)-Prolyl-{(2R)-2-Amino-3-cyclohexylpropanoyl}-Phenylalanyl-DArginyl-OH After Hydrocinnamoyl-Lysyl(N-epsilon-Fmoc)-Prolyl-{(2R)-2-Amino-3-cyclohexylpropanoyl}-Phenylalanyl-DArginyl(guanidino-Tos)-OResin was synthesized according to the method described in Example 1, the peptide-resin (0.6 g) was treated with 15 mL of 20% piperidine in DMF for 8 hours. After the resin was washed with DMF (4×15 mL), it was then reacted with nicotinic acid (10 equivalents) in the presence of N,N'-diisopropylcarbodiimide (DIC) (10 equivalents) in 15 mL of DMF for 1 hour. The crude peptide (99.4 mg) was isolated and purified according to the procedure described in Example 2 to yield 31.7 mg of title compound.

FAB+ MS: (M+H)+ =937. Amino Acid Anal: Lys (0.99), Pro (0.95), Cha (0.98), Phe (0.96), Arg (1.04).

EXAMPLE 105

(N-Methyl)Phenylalanyl-Lysyl-Prolyl-{(2R)-2-Amino-3-cyclohexylpropanoyl}-Phenylalanyl-N-(2-Amidinoethyl)amide The compound (130 mg, 0.14 mmole) synthesized as a precursor for Example 154, was converted to its amidine analogue by the literature method: Lee, M.; Coulter, D. M.; Lown, J. W.; J. Org. Chem. 1988, 53, 1858. The obtained compound was deprotected and purified to obtain the title compound (27 mg) in 18% yield.

FAB+ MS: (M+H)+ =774. Animo Acid Anal: MePhe (0.86), Lys (0.91), Pro (1.02), Cha (0.95), Phe (1.12).

EXAMPLE 106

Hydrocinnamoyl-Lysyl-Prolyl-{(2R)-2-Amino-3-cyclohexylpropanoyl}-DArginyl-OH

FAB+ MS: (M+H)+ =684.

EXAMPLE 107

(N-Methyl)Phenylalanyl-Lysyl-Prolyl-{(2R)-2-Amino-3-cyclohexylpropanoyl}-Phenylalanyl-NH$_2$ Boc-(N-Methyl)Phenylalanyl-Lysyl(N-epsilon-Boc)-Prolyl-{(2R)-2-Amino-3-cyclohexylpropanoyl}-OH (Example 3) (100 mg, 0.13 mmole) was reacted with commercially available H-Phenylalanylamide hydrochloride (30 mg, 0.15 mmole) via the mixed anhydride method as exemplified in Example 116. Deprotection and purification gave 91 mg of the title compound in 74% yield.

FAB+ MS: (M+H)+ =704. Amino Acid Anal: MePhe (0.81), Cha (0.98), Lys (1.02), Pro (1.04), Phe (0.95).

EXAMPLE 108

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Phenethyl)amide FAB+ MS: (M+H)+ =814. Amino Acid Anal: MePhe (0.90), Cha (1.88), Lys (0.98), Pro (1.02).

EXAMPLE 109

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2,2-Dimethyl-2-Phenethyl)amide Diethyl(alpha,alpha-dimethylbenzyl)malonate was prepared according to the literature: Holmberg, C.; Liebigs Ann. Chem., 1981, 748. This (4.0 g, 14.4 mmole) was refluxed in 30 mL of 1:1 propionic acid/12 N hydrochloric acid for 2 days to yield 1.84 g (72%) of 3-phenyl-3,3-dimethylpropionic acid. This acid (1.0 g, 5.6 mmole) was converted to N-Boc-2-phenyl-2,2-dimethylethylamine (MS: (M+H)+ =250) (250 mg, 18%) by the method described in the literature: Plattner, J. J. et. al., J. Med. Chem., 1988, 31, 2277. The title compound was prepared from the deprotected amine and compound of Example 5 via the EDC and HOBT method followed by deprotection and purification.

FAB+ MS: (M+H)+ =842. Amino Acid Anal: MePhe (0.86), Lys (0.97), Pro (1.03), Cha (1.92).

EXAMPLE 110

(N-Methyl)Phenylalanyl-Lysyl-Prolyl-{(2R)-2-Amino-3-cyclohexylpropanoyl}-N-{(1S)-1-phenyl-2-guanidino)ethyl}amide FAB+ MS: (M+H)+ =732. Amino Acid Anal: MePhe (1.23), Lys (1.00), Pro (1.00), Cha (1.15).

EXAMPLE 111

Cis-1-[(N-Methyl)Phenylalanyl-Lysyl-Prolyl-{(2R)-2-Amino-3-cyclohexylpropanoyl}-{(2S)-2-Amino-3-cyclohexylpropanoyl}]amido-4-Aminocyclohexane This compound in a bis-Boc protected form was prepared as an intermediate in the synthesis of Example 123. Deprotection afforded the title compound.

FAB+ MS: (M+H)+ =807. Amino Acid Anal: MePhe (0.97), Lys (1.00), Pro (1.07), Cha (1.94).

EXAMPLE 112

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1RS)-1-Benzyl-3-phenylpropyl}amide FAB+ MS: (M+H)+ =918. Amino Acid Anal: MePhe (0.83), Lys (0.97), Pro (1.03), Cha (1.80).

EXAMPLE 113

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(dl)-1-Phenyl-3-phenylpropyl}amide The compound was prepared in analogy to Example 60.

FAB+ MS: (M+H)+ =904. Amino Acid Anal: MePhe (0.92), Lys (0.91), Pro (1.09), Cha (1.80).

EXAMPLE 114

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Nitrobenzyl)amide FAB+ MS: (M+H)+ =845. Amino Acid Anal: Lys (0.97), Pro (1 03), Cha (1.89), MePhe (0.87).

EXAMPLE 115

N-(4-Guanidinobutyl)-N-[(N-Methyl)Phenylalanyl-Lysyl-Prolyl-{(2R)-2-Amino-3-cyclohexylpropanoyl}-{(2S)-2-Amino-3-cyclohexylpropyl}]amine N-[Boc-(2S)-2-Amino-3-cyclohexylpropyl]-N-[(4-Cbz-amino)butyl]amine (231 mg, 0.5 mmole), prepared in Example 78, was treated with 4N hydrochloric acid in dioxane to remove the Boc group, followed by coupling to the compound of (381 mg, 0.5 mmole) of Example 3 to obtain N-[Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropyl]-N-[4-(N-Cbz-amino)butyl]amine (350 mg, MS: (M+H)+ =1101) in 64% yield. This product was hydrogenated, guanidinated, and then treated as described in Example 42.

FAB+ MS: (M+H)+ =809. Amino Acid Anal: MePhe (0.81), Lys (0.98), Pro (1.02), Cha (0.89).

EXAMPLE 116

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Picolyl)amide N-Boc-Phenylalanyl-Lysyl(N-epsilon-Boc)-prolyl-{(2R)-2-Amino-3-cyclohexylpropanoyl}-{(2S)-2-Amino-3-cyclohexylpropanoyl}-OH (Example 5) (230 mg, 0.3 mmole) was dissolved in 10 mL of methylene chloride and cooled to −20° C. (dry ice/carbon tetrachloride bath), isobutylchloroformate (IBCF) (49 μL, 0.36 mmole), followed by N-methylmorpholine (NMM) (40 μL, 0.36 mmole) were added. After 5 minutes at −20° C., 2-(aminomethyl)pyridine (62 μL, 0.6 mmole) was added; the reaction mixture was stirred at −20° C. for 1 hour and at room temperature for 3 hours. The solvent was removed under reduced pressure and ethyl acetate (30 mL) was added to the residue. The ethyl acetate layer was washed with 10% sodium bicarbonate solution, brine, 10% potassium hydrogen sulfate solution, and brine, and then dried over anhydrous magnesium sulfate. The solvent was removed under reduced pressure and the residue was treated with 4N hydrochloric acid in dioxane (10 mL) for 45 minutes. After the solvent was evaporated, the peptide obtained (185 mg) was purified as described in Example 2. From the crude product (95 mg), 60.0 mg of pure title compound was obtained.

FAB+ MS: (M+H)+ =801. Amino Acid Anal: Lys (0.96), Pro (1.04), Cha (1.84), MePhe (1.14).

EXAMPLE 117

1-Benzyl-4-[(N-Methyl)Phenylalanyl-Lysyl-Prolyl-{(2R)-2-Amino-3-cyclohexylpropanoyl}]piperazine FAB+ MS: (M+H)+ =716. Amino Acid Anal: MePhe (0.87), Lys (0.97), Pro (1.06), Cha (0.98).

EXAMPLE 118

(N-Methyl)Phenylalanyl-Lysyl-Prolyl-{(2R)-2-Amino-3-cyclohexylpropanoyl}-{N-2-Aminoethyl-N-2-phenethyl}amide The compound was prepared in analogy to Example 156.

FAB+ MS: (M+H)+ =704. Amino Acid Anal: MePhe (0.83), Lys (0.98), Pro (1.02), Cha (0.97).

EXAMPLE b 119

(N-Methyl)Phenylalanyl-Lysyl-Prolyl-{(2R)-2-Amino-3-cyclohexylpropanoyl}-{(S)-(−)-2-Amino-3-phenyl-1-propanol}

The compound was prepared in analogy to Example 107, except commercially available (S)-(−)-2-Amino-3-phenyl-1-propanol (Phenylalaninol) was used to afford the title compound in 63% yield.

FAB+ MS: (M+H)+ = 691. Amino Acid Anal: MePhe (0.82), Cha (0.96), Lys (1.00), Pro (1.00).

EXAMPLE 120

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Aminopropyl)amide}

Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropanoyl}-OH (Example 5) (0.2 g, 0.22 mmole) was reacted with 1,3-diaminopropane (0.46 mL, 5.5 mmole) via the mixed anhydride method as described in the procedure of Example 116 in 30% yield. Treatment with trifluoroacetic acid in methylene chloride, followed by RP-HPLC gave the title compound in 83% yield.

FAB+ MS: (M+H)+ = 767. Amino Acid Anal: MePhe (0.92), Cha (1.91), Lys (1.01), Pro (0.99).

EXAMPLE 121

(N-Methyl)Phenylalanyl-Lysyl-Prolyl-{(2R)-2-Amino-3-cyclohexylpropanoyl}-N-(2-Cyclohexylethyl)amide FAB+ MS: (M+H)+ = 667. Amino Acid Anal: MePhe (1.08), Lys (0.97), Pro (1.03), Cha (0.97).

EXAMPLE 122

(N-Methyl)Phenylalanyl-Lysyl-Prolyl-{(2R)-2-Amino-3-cyclohexylpropanoyl}-N-{(1S)-1-Phenyl-3-guanidinopropyl}amide FAB+ MS: (M+H)+ = 746. Amino Acid Anal: MePhe (1.29), Lys (1.00), Pro (1.00), Cha (1.13).

EXAMPLE 123

Cis-1-[(N-Methyl)Phenylalanyl-Lysyl-Prolyl-{(2R)-2-Amino-3-cyclohexylpropanoyl}-{(2S)-2-Amino-3-cyclohexylpropanoyl}]-4-Guanidinylcyclohexane To a stirred solution of Cbz-trans-4-aminocyclohexanol (4 g, 16.1 mmol), prepared as described in Example 133, in dichloromethane (60 mL) and cooled to −78° C. was added trifluoromethanesulfonic anhydride (3.24 mL, 19.3 mmol), followed after 5 min with 2,6-lutidine (2.43 mL, 20.9 mmol) added dropwise. Upon completion of addition, the reaction was stirred 30 min, before the dropwise addition of a solution of tetramethylguanindinium azide (Papa, J. J. Org. Chem. 1966, 31, 1426.) (7.04 g, 48.2 mmol) in dichloromethane (20 mL). The mixture was stirred at −78° C. for 15 minutes, then allowed to warm to 0° C. and stirred for 2 hours. It was passed through a silica plug (25 g, 70-230 mesh) and eluted with dichloromethane followed by ethyl acetate. Fractions containing the desired product were concentrated in vacuo to afford an oil. The oily residue was partitioned between ethyl acetate (50 mL) and 1N hydrochlorid acid (50 mL) and the acidic aqueous layer was extracted with an additional portion of ethyl acetate. The organic extracts were combined, washed with brine (50 mL), dried over anhydrous sodium sulfate, filtered, and the solvent removed in vacuo to give the crude product as an oil (4.50 g). The material was purified by medium pressure liquid chromatography (MPLC) on silica gel (70-230 mesh, 1.5×45 cm column) using a 6:1 hexane/ethyl acetate, 4:1 hexane/ethyl acetate, ethyl acetate step gradient. Fractions containing the pure product were pooled and concentrated in vacuo to give N-Cbz-cis-4-aminocyclohexyl azide (1.68 g, 38% yield) as a yellow solid: m.p. 42°–46° C.; $^1$H NMR (300 MHz) δ 7.36 (m, 5H), 5.09 (s, 2H), 4.70 (br, 1H), 3.71 (br, 1H), 3.60 (br, 1H), 1.48–1.84 (comp, 8H). This compound was carried on using the procedures described in Example 133 to give the amine: (1.3 g, 86% yield) as a clear oil: $^1$H NMR (300 MHz) δ 7.35 (m, 5H), 5.10 (s, 2H), 4.84 (br, 1H), 3.73 (br, 1H), 2.87 (m, 1H), 1.25–1.76 (comp, 10H). The amine was coupled with the peptide in analogy to Example 133 to give the coupled product (72 mg, 40%). MS: (M+H)+ = 1114. Guanidination and deprotection were carried out in analogy to Example 133 to give the title compound (15 mg, 23% yield) as the trifluoroacetate salt in the form of a white powder.

FAB+ MS: (M+H)+ = 849. Amino Acid Anal: MePhe (0.97), Lys (1.00), Pro (1.04), Cha (1.90).

EXAMPLE 124

(N-Methyl)Phenylalanyl-Lysyl-Prolyl-{(2R)-2-Amino-3-cyclohexylpropanoyl}-N-{(1RS)-1-Benzyl-3-phenylpropyl}amide FAB+ MS: (M+H)+ = 765. Amino Acid Anal: MePhe (0.81), Lys (1.01), Pro (0.99), Cha (0.86).

EXAMPLE 125

(N-Methyl)Phenylalanyl-Lysyl-Prolyl-{(2R)-2-Amino-3-cyclohexylpropanoyl}-Phenylalanyl-N-{2-(Indol-3-yl)ethyl}amide FAB+ MS: (M+H)+ = 847. Amino Acid Anal: Lys (1.00), Pro (0.99), Cha (0.98), Phe (1.01), MePhe (0.85).

EXAMPLE 126

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(3-Carboxy)benzyl}amide FAB+ MS: (M+H)+ = 844 Amino Acid Anal: Lys (0.97), Pro (1.03), Cha (1.75), MePhe (0.86).

EXAMPLE 127

(N-Methyl)Phenylalanyl-Lysyl-Prolyl-{(2R)-2-Amino-3-cyclohexylpropanoyl}-{(2S)-2-Amino-3-cyclohexylpropanoyl}-N-{2-(4-Hydroxyphenyl)ethyl}amide FAB+ MS: (M+H)+ = 830. Amino Acid Anal.: Lys (0.99), Pro (1.01), Cha (1.95), MePhe (1.11).

EXAMPLE 128

(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Picolyl)amide FAB+ MS: (M+H)+ = 801. Amino Acid Anal.: Lys (1.04), Pro (0.96), Cha (1.97), MePhe (1.09).

EXAMPLE 129

(N-Methyl)Phenylalanyl-Lysyl-Prolyl-{(2R)-2-Amino-3-cyclohexylpropanoyl}-Phenylalanyl-N-(Cyclohexylmethyl)amide FAB+ MS: (M+H)+ =800. Amino Acid Anal: MePhe (0.95), Lys (0.95), Pro (1.02), Cha (0.97), Phe (1.05).

EXAMPLE 130

(N-Methyl)Phenylalanyl-Lysyl-Prolyl-{(2R)-2-Amino-3-cyclohexylpropanoyl}-Phenylalanyl-N-Benzylamide FAB+ MS: (M+H)+ =794. Amino Acid Anal: MePhe (0.97), Cha (0.97), Lys (1.04), Pro (1.07), Phe (0.92).

EXAMPLE 131

(N-Methyl)Phenylalanyl-Lysyl-Prolyl-{(2R)-2-Amino-3-cyclohexylpropanoyl}-Phenylalanyl-N-Methyl-N-benzylamide FAB+ MS: (M+H)+ =808. Amino Acid Anal: MePhe (1.09), Lys (0.97), Pro (0.97), Cha (1.00), Phe (1.06).

EXAMPLE 132

(N-Methyl)Phenylalanyl-Lysyl-Prolyl-{(2R)-2-Amino-3-cyclohexylpropanoyl}-{(2S)-2-Amino-3-cyclohexylpropanoyl}-N-Benzyl-N-{(3RS)-3-phenyl-4-guanidinobutyl}amide Benzyl cyanide (0.97 mL, 8.4 mmole) was reacted with lithium bis(trimethylsilyl)amide (LHMDSA) (8.4 mL, 8.4 mmole) in 5 mL of THF at −78° C. for 1 hour. After an additional aliquot of LHMDSA (4.2 mL, 4.2 mmole) was added, N-(2-chloroethyl)dibenzylamine hydrochloride (1.0 g, 3.4 mmole) was then added. The reaction was allowed to stand at room temperature and was then warmed to 50° C. for 3.5 hours. The mixture was poured into ice/water, and the product was extracted with ethyl acetate. The ethyl acetate layer was washed with brine, dried over sodium sulfate and concentrated under reduced pressure to afford alpha-(N,N-dibenzylaminoethyl) benzyl cyanide (1.05 g), isolated in 94% yield (MS: (M+H)+ =341).

After hydrogenolysis (Example 146), the amine obtained (237 mg, 0.7 mmole) was reacted with N-ethoxycarbonylphthalimide (302 mg, 1.4 mmole) according to the literature method; Nefkens, G. H.; Tesser, G. I.; Nivard, R. J.: Rec. Trav. Chim. Pays-Bas 1960, 79, 688 to afford (N,N-dibenzylaminoethyl)-1-phenylethylphthalimide (210 mg, 64%). (MS; (M+H)+ =475). The mono N-benzyl group of the above product was removed by hydrogenolysis and the product obtained coupled with the compound of Example 5 to afford the fully protected pentapeptide analogue in quantitative yield.

This pentapeptide (260 mg, 0.2 mmole) was treated with hydrazine hydrate (10 mL) in 5 mL of ethanol at room temperature for 5 hours with stirring. After the solvent was removed, the final guanidination, deprotection and purification were carried out to obtain the title compound (30 mg).

FAB+ MS: (M+H)+ =989. Amino Acid Anal.: MePhe (0.95), Lys (0.99), Pro (1.01), Cha (1.95).

EXAMPLE 133

Trans-1-[(N-Methyl)Phenylalanyl-Lysyl-Prolyl-{(2R)-2-Amino-3-cyclohexylpropanoyl}-{(2S)-2-Amino-3-cyclohexylpropanoyl}]-4-Guanidinylcyclohexane Commercially available trans-4-aminocyclohexanol hydrochloride (50 g, 0.33 mol) was treated with benzyl chloroformate (Cbz-Cl) (51.8 mL, 0.36 mol) under standard Schotten-Baumann conditions to provide N-Cbz-trans-4-aminocyclohexanol (62.33 g, 88% yield) as a white solid: m.p. 160°-162° C.; $^1$H NMR (300 MHz) δ 7.36 (m, 5H), 5.10 (s, 2H), 4.58 (br, 1H), 3.61 (m, 1H), 3.51 (m, 1H), 2.01 (br t, 4H, J=13.5 Hz), 1.40 (m, 2H), 1.20 (m, 2H); MS: (M+H)+ =250, (M+H+NH$_3$)+ =267.

To a solution of the above compound (5 g, 20 mmol) and triethylamine (8.4 mL, 60 mmol) in dichloromethane (60 mL) cooled to −10 ° C. was added a solution of pyridine-sulfur trioxide complex (9.58 g, 60 mmol) in DMSO (60 mL) in a single portion. The mixture was stirred at −10° C. for 1 hour then at room temperature for 2 hours. Additional pyridinesulfur trioxide complex (3.2 g, 20 mmol) was added and the reaction allowed to stir an additional 15 min. The mixture was poured into ice-cold brine (180 mL) and the product extracted into ice-cold ether (160 mL). The resulting emulsion was filtered through a bed of Celite and the two phases were separated. The organic layer was washed with ice-cold 10% aqueous citric acid (180 mL) followed by ice-cold brine (180 mL). The organic layer was dried over anhydrous sodium sulfate, filtered, and the solvent removed in vacuo to yield a crude waxy solid (2.86 g) which was purified by MPLC on silica gel (70-230 mesh, 1.5×45 cm column) using a 4:1 hexane/ethyl acetate, 2:1 hexane/ethyl acetate, and ethyl acetate step gradient. Fractions containing pure product were pooled and concentrated in vacuo to give N-Cbz-4-aminocyclohexanone (2.36 g, 48% yield) as a white solid: m.p. 82°-84° C.; $^1$H NMR (300 MHz) δ 7.37 (m, 5H), 5.11 (s, 2H), 4.75 (br, 1H), 4.00 (m, 1H), 2.41 (m, 4H), 2.25 (m, 2H), 1.71 (m, 2H).

This ketone (2.36 g, 9.55 mmol) in THF (5 mL) was added dropwise to a stirred solution of L-selectride in THF (1M, 19.1 mL, 9.55 mmol) under N$_2$ at −78° C. The reaction mixture was stirred at −78° C. for 3 hours, methanol (0.5 mL) was added, and the reaction mixture was allowed to warm to room temperature. 1N hydrochloric acid (5 mL) was added and the mixture stirred overnight. The reaction mixture was extracted with ethyl acetate (2×20 mL) and the combined organic layers were washed with brine (2×20 mL), dried over anhydrous sodium sulfate, filtered, and the solvent removed in vacuo to yield 2.73 g crude oil. The crude product was purified by MPLC on silica gel (70-230 mesh, 1.5×45 cm column) using a 1:1 hexane/ethyl acetate, 2:1 hexane/ethyl acetate, and ethyl acetate step gradient. Fractions containing pure product were pooled and concentrated in vacuo to give a clear oil (cis-N-Cbz-4-aminocyclohexanol) (1.35 g, 57% yield): $^1$H NMR (300 MHz) δ 7.35 (m, 5H), 5.10 (s, 2H), 4.74 (br, 1H), 3.91 (br, 1H), 3.62 (br, 1H), 1.18 (m, 8H); MS: (M+H)+ =250, (M+H+NH$_3$)+ =267.

To a stirred solution of N-Cbz-cis-4-aminocyclohexanol (1.03 g, 4.1 mmol) in dichloromethane (20 mL) cooled to 0° C. was added triethylamine (0.86 mL, 6.2 mmol) followed by methanesulfonyl chloride (0.32 mL, 4.1 mmol). The reaction was allowed to warm to room temperature and was stirred for 2 hours, diluted with dichloromethane (20 mL) and the solution was washed with 1N phosphoric acid (2×20 mL), saturated sodium bicarbonate solution (2×20 mL), followed by brine (2×20 mL). The organic layer was dried over anhydrous sodium sulfate, filtered, and concentrated in vacuo. The resulting mesylate was dissolved in DMF (20 mL), sodium azide (0.54 g, 8.3 mmol) was added, and the solution was stirred at 55° C. for 20 hours. The reaction was cooled to room temperature and partitioned between ethyl acetate (40 mL) and water (20 mL). The organic layer was washed with brine (2×20 mL), dried over anhydrous sodium sulfate, filtered, and reduced in vacuo to give 1.08 g crude azide. Purification on a silica plug (25 g, 70-230 mesh) with elution by a 6:1 hexane/ethyl acetate, 4:1 hexane/ethyl acetate, 2:1 hexane/ethyl acetate step gradient gave pure azide (trans-N-Cbz-4-aminocyclohexylazide) (0.68 g, 60% yield) as a white solid: m.p. 69°-73° C.; $^1$H NMR (300 MHz) δ 7.35 (m, 5H), 5.09 (s, 2H), 4.59 (br, 1H), 3.51 (br, 1H), 3.28 (dddd, 1H, J=10.8, 10.8, 3.9, 3.9), 2.05 (m, 4H), 1.46 (m, 2H), 1.21 (m, 2H); MS: $(M+H+NH_3)^+ = 292$.

A solution of the above azide (0.68 g, 2.5 mmol), triethylamine (1.73 mL, 12.5 mmol), and 1,3-propanedithiol (1.24 mL, 12.5 mmol) in methanol (12.5 mL) was stirred at 55° C. for 48 hours. The methanol was removed in vacuo and the oily residue partitioned between ether (15 mL) and 1N HCl (15 mL). The aqueous layer was washed with an additional portion of ether then adjusted to pH 9 with 7N sodium hydroxide. The basic aqueous solution was then extracted with ether (3×15 mL). The extracts were combined, dried over anhydrous sodium sulfate, filtered, and concentrated in vacuo to yield (trans-N-Cbz-4-aminocyclohexylamine (0.48 g, 77% yield) as a light yellow waxy solid: m.p. 155°-160° C. (decomp); $^1$H NMR (300 MHz) δ 7.36 (m, 5H), 5.08 (s, 2H), 4.55 (br, 1H), 3.47 (br, 1H), 2.64 (m, 1H), 2.02 (m, 2H), 1.86 (m, 2H), 1.51 (br, 2H), 1.21 (m, 4H).

The peptide Boc-(N-Methyl)Phenylalanyl-Lysyl(N-epsilon-Boc)-Prolyl-{(2R)-2-Amino-3-cyclohexylpropanoyl}-{(2S)-2-Amino-3-cyclohexylpropanoyl}-OH was prepared by standard solid phase techniques exemplified in Example 1, removed from the resin with anhydrous HF, and reprotected at the N-terminus and the epsilon-amine of Lysine with di-tert-butyl dicarbonate.

To a stirred solution of the above peptide (0.15 g, 0.16 mmol), trans-N-Cbz-4-aminocyclohexylamine (0.12 g, 0.48 mmol), and 1-hydroxybenzotriazole hydrate (HOBT) (0.02 g, 0.16 mmol) in dichloromethane (1.5 mL) cooled to 0° C. was added 1-(3-dimethylaminopropyl)-3-ethylcarbodiimide hydrochloride (EDC) (0.03 g, 0.18 mmol). The solution was stirred at room temperature for one overnight. Dichloromethane (4 mL) was added and the solution was washed with 1N hydrochloric acid (2×2 mL), 0.5% aqueous copper(II) sulfate (2×2 mL), and brine (2×2 mL). The organic layer was dried over anhydrous sodium sulfate, filtered, and the solvent was removed in vacuo to give crude product (0.14 g) which was purified by MPLC on silica gel (70-230 mesh, 1.5×45 cm column) using 1:4 hexane/ethyl acetate as the mobile phase. Fractions containing product were pooled and concentrated in vacuo to give the coupled product (72 mg, 40% yield): MS: $(M+H)^+ = 1141$.

An appropriate vessel was flushed with nitrogen and then equipped with a nitrogen inlet. The above Cbz-protected peptide (72 mg, 0.06 mmol), 10% Pd/C (8 mg, 10 weight %), and ammonium formate (40 mg, 0.6 mmol) were added followed by methanol (1 mL). The mixture was stirred overnight and the catalyst was removed by filtration and washed with methanol. The filtrates were combined and the solvent removed in vacuo to give an oily residue. A stirred solution of this oil, triethylamine (0.03 mL, 0.21 mmol), and 3,5-dimethylpyrazole-1-carboxamidine nitrate (0.038 g, 0.18 mmol) in dimethylformamide (1 mL) under nitrogen was heated at 40° C. for 2 days then was stirred at room temperature for 5 days. The solvent was removed in vacuo and the residue stirred with 4.8M hydrochloric acid in dioxane (2 mL) for 3 hours. The solvent was removed in vacuo and the residue triturated with chloroform (3×10 mL). The resulting crude peptide was purified by the method described in Example 2. The fractions containing product were pooled and lyophilized to give the guanidinated compound (10 mg, 15% yield) as the trifluoroacetate salt in the form of a white powder: MS: $(M+H+NH_3)^+ = 849$. Amino Acid Analysis, NMePhe (0.97), Lys (1.00), Pro (1.04), Cha (1.90).

EXAMPLE 134

(N-Methyl)Phenylalanyl-Lysyl-prolyl-{(2R/S)-2-Amino-3-cyclohexylpropanoyl}-{(2R/S)-2-Amino-3-cyclohexyl-2-(5-guanidinopentyl)propanoyl}-N-(2-Phenethyl)amide The compound (2-amino-2-cyclohexylmethyl-6-cyano)hexanoyl-2-phenethylamide (290 mg, 0.8 mmole) was reacted with di-tert-butyl dicarbonate (0.18 g, 0.8 mmole) and triethylamine (TEA) (0.11 mL, 0.8 mmole) at 45° C. for one over night. Ethyl acetate was added to the reaction mixture which was then washed with 0.2M phosphoric acid, brine, dried over sodium sulfate and concentrated under reduced pressure. After silica gel column chromatography, eluting with 2-5% methanol in methylene chloride, 170 mg of (2-Boc-amino-2-cyclohexylmethyl-6-cyano)hexanoyl-N-(2-phenethyl)amide was obtained in 47% yield. This (160 mg, 0.4 mmole) was reacted with cobalt chloride (91.3 mg, 0.8 mmole) and sodium borohydride (133 mg, 4.0 mmole) in 5 mL of methanol for 2 hours to obtain 2-Boc-amino-2-cyclohexylmethyl-7-aminoheptanoyl-2-phenethylamide (MS:$(M+H)^+ = 460$) in quantitative yield.

All of the above amine was protected with a Cbz group, followed by deprotection of the Boc group and coupling with the compound of Example 3 via the EDC and HOBT method. The coupling reaction was carried out at room temperature for 6 days. Boc-(N-Methyl)-Phenylalanyl-Lysyl(N-epsilon-Boc)-Prolyl-{(2R/S)-2-Amino-3-cyclohexylpropanoyl}-{(2R/S)-2-Amino-3-cyclohexyl-2-(5-N-Cbz-aminopentyl)propanoyl}-N-(2-Phenethyl)amide (MS: $(M+H)^+ = 1234$) was isolated. After the Cbz group was cleaved by hydrogenolysis, the compound was treated in analogy to Example 42. During the peptide coupling, the (2R)-2-Amino-3-cyclohexylpropanoyl residue racemized, however, the four diastereomers produced were separable by RP-HPLC.

FAB$^+$ MS: $(M+H)^+ = 941$. Amino Acid Anal: MePhe (0.74), Lys (1.00), Pro (1.00), Cha (0.92).

EXAMPLE 135

(N-Methyl)Phenylalanyl-Lysyl-Prolyl-{(2R/S)-2-Amino-3-cyclohexylpropanoyl}-(2R/S)-2-Amino-3-cyclohexyl-2-(5-guanidinopentyl)propanoyl}-N-(2-Phenethyl)amide The compound was one of the diastereomers of Example 134.

FAB+ MS: (M+H)+ =941. Amino Acid Anal: MePhe (0.78), Lys (0.99), Pro (1.01), Cha (0.92).

EXAMPLE 136

(N-Methyl)Phenylalanyl-Lysyl-Prolyl-{(2S/R)-2-Amino-3-cyclohexylpropanoyl}-(2R/S)-2-Amino-3-cyclohexyl-2-(5-guanidinopentyl)propanoyl}-N-(2-Phenethyl)amide The compound was one of the diastereomers of Example 134.

FAB+ MS: (M+H)+ =941. Amino Acid Anal: MePhe (0.82), Lys (0.95), Pro (1.05), Cha (0.91).

EXAMPLE 137

(N-Methyl)Phenylalanyl-Lysyl-Prolyl-{(2S/R)-2-Amino-3-cyclohexylpropanoyl}-(2R/S)-2-Amino-3-cyclohexyl-2-(5-guanidinopentyl)propanoyl}-N-(2-Phenethyl)amide The compound was one of the diastereomers of Example 134.

FAB+ MS: (M+H)+ =941. Amino Acid Anal: MePhe (0.82), Lys (0.94), Pro (1.06), Cha (0.91).

EXAMPLE 138

(N-Methyl)Phenylalanyl-Lysyl-Prolyl-{(2R)-2-Amino-3-cyclohexylpropanoyl}-{(2S)-2-Amino-3-cyclohexylpropanoyl}-N-{2-(Indol-3-yl)ethyl}amide FAB+ MS: (M+H)+ =853. Amino Acid Anal: MePhe (0.97), Lys (0.99), Pro (1.01), Cha (1.87).

EXAMPLE 139

(N-Methyl)Phenylalanyl-Lysyl-Prolyl-{(2R)-2-Amino-3-cyclohexylpropanoyl}-{(2S)-2-Amino-3-cyclohexylpropanoyl}-N-(Benzyloxy)amide Boc-(N-Methyl)Phenylalanyl-Lysyl(Boc)-Prolyl-{(2R)-2-Amino-3-cyclohexylpropanoyl}-{(2S)-2-Amino-3-cyclohexylpropanoyl}-OH (Example 5) (141.8 mg, 0.15 mmole) was reacted with O-benzylhydroxylamine hydrochloride (48 mg, 0.3 mmole) in the presence of isobutylchloroformate (IBCF) (25 μL, 0.18 mmole) and triethylamine (TEA) (67 μL, 0.48 mmole) in 5 mL of methylene chloride and treated in the method described in Example 116. 2/3 of the crude peptide was purified to yield 50.0 mg of the title compound.

FAB+ MS: (M+H)+ =816. Amino Acid Anal: Lys (0.97), Pro (1.03), Cha (1.90), MePhe (0.96).

EXAMPLE 140

(N-Methyl)Phenylalanyl-Lysyl-Prolyl-{(2R)-2-Amino-3-cyclohexylpropanoyl}-Phenylalanyl-N-(2-Phenethyl)amide FAB+ MS: (M+H)+ =808. Amino Acid Anal: MePhe (0.90), Lys (1.00), Pro (1.00), Cha (0.95), Phe (1.25).

EXAMPLE 141

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Picolyl)amide FAB+ MS: (M+H)+ =801. Amino Acid Anal: Lys (1.09), Pro (0 91), Cha (1.77), MePhe (1 02).

EXAMPLE 142

(N-Methyl)Phenylalanyl-Lysyl-Prolyl-{(2R)-2-Amino-3-cyclohexylpropanoyl}-Phenylalanyl-N-{(1R)-1-Phenethyl}amide FAB+ MS: (M+H)+ =808. Amino Acid Anal: MePhe (0.90), Lys (0.94), Pro (1.04), Cha (0.97), Phe (1.04).

EXAMPLE 143

(N-Methyl)Phenylalanyl-Lysyl-Prolyl-{(2R)-2-Amino-3-cyclohexylpropanoyl}-N-(5-Aminopentyl)-N-(2-phenethyl)amide The compound was prepared in analogy to Example 156.

FAB+ MS: (M+H)+ =746. Amino Acid Anal: MePhe (0.84), Lys (0.98), Pro (1.03), Cha (0.90).

EXAMPLE 144

(N-Methyl)Phenylalanyl-Lysyl-Prolyl-{(2R)-2-Amino-3-cyclohexylpropanoyl}-Phenylalanyl-N-(4-Guanidinobutyl)amide Boc-Phenylalanine (1.16 g, 4.38 mmole) was coupled with agmatine sulfate (1.00 g, 4.38 mmole) by using 1-(3-dimethylaminopropyl)-3-ethylcarbodiimide hydrochloride (EDC) (0.84 g, 4.38 mmole), HOBT (0.6 g, 4.38 mmole) and NMM (0.5 mL, 4.38 mmole) in 10 mL of 8:2 DMF/water. After stirring for one over night, the mixture was diluted with chloroform and the organic layer was washed with saturated sodium bicarbonate and brine, dried over sodium sulfate, and concentrated under reduced pressure.

The dipeptide analogue obtained (in 55% yield, MS: (M+H)+ =378) (50 mg, 0.13 mmole) was treated with 4N hydrochloric acid in dioxane, and then reacted with Boc-(N-Methyl)Phenylalanyl-Lysyl-Prolyl-{(2R)-2-Amino-3-cyclohexylpropanoyl}-OH (compound 3) (100 mg, 0.13 mmole) by the method described in Example 116. Deprotection was carried out using 50% trifluoroacetic acid in methylene chloride, then purification was carried out to obtain the title compound in 12% yield.

FAB+ MS: (M+H)+ =817. Amino Acid Anal: MePhe (0.75), Lys (1.08), Pro (1.06), Cha (0.96), Phe (0.89).

EXAMPLE 145

(N-Methyl)Phenylalanyl-Lysyl-Prolyl-{(2R)-2-Amino-3-cyclohexylpropanoyl}-{(2S)-2-Amino-3-cyclohexylpropanoyl}-N{(R)-1-Phenethyl)amide FAB+ MS: (M+H)+ =814. Amino Acid Anal: MePhe (1.04), Lys (0.96), Pro (1.04), Cha (1.98).

EXAMPLE 146

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(2RS)-2-Phenyl-4-guanidino)butyl}amide The cyano group of alpha-(N,N-dibenzylaminoethyl) benzyl cyanide (1.0 g, 2.9 mmole) as described in Example 132 was reduced by hydrogenolysis; and the amine obtained (56 mg, 0.2 mmole) was reacted with the compound (150 mg, 0.2 mmole) of Example 5 via the EDC and HOBT method as described in Example 3. The peptide obtained (220 mg, 0.2 mmole) was hydrogenated with 10% palladium on carbon (220 mg) in 50 mL of acetic acid under 4 atmospheres of hydrogen to remove the bis-benzyl group. The free amino group obtained was guanidinated, and the title compound (42 mg, isolated as a mixture of diastereomers) was obtained by the method described in Example 116.

FAB+ MS: (M+H)+ =899. Amino Acid Anal: MePhe (0.98), Lys (0.99), Pro (1.01), Cha (1.92).

EXAMPLE 147

Trans-1-[(N-Methyl)Phenylalanyl-Lysyl-Prolyl-{(2R)-2-Amino-3-cyclohexylpropanoyl}-{(2S)-2-Amino-3-cyclohexylpropanoyl}]4-Aminocyclohexane This compound in a bis-Boc protected form was prepared as an intermediate in the synthesis of Example 133. Deprotection afforded the title compound.

FAB+ MS: (M+H)+ =807. Amino Acid Anal: MePhe (0.97), Lys (1.00), Pro (1.06), Cha (1.91).

EXAMPLE 148

{(R/S)-(2-Carboxyl)-3-phenylpropionyl}-Lysyl-Prolyl-{(2R)-2-Amino-3-cyclohexylpropanoyl}-{(2S)-2-Amino-3-cyclohexylpropanoyl}-DArginyl-OH (dl)-Benzylmalonate monoethyl ester (1.11 g, 5 mmole) was reacted with tert-butyl alcohol (0.707 mL, 7.5 mmole) in the presence of dicyclohexylcarbodiimide (DCC) (1.135 g, 5.5 mmole) and dimethylaminopyridine (DMAP) (0.611 g, 5 mmole) in 10 mL of methylene chloride. The reaction was carried out at 0° C. for 4 hours and at room temperature for one over night. After the usual work up, (dl)-benzylmalonate monoethyl mono-tert-butyl ester (1.191 g, 85.6%) was obtained. This (1.150 g, 4.1 mmole) was dissolved in 7 mL of ethyl alcohol and 3 mL of 2N lithium hydroxide (6 mmole) was added and the reaction mixture stirred for 45 minutes. (dl)-Benzylmalonate mono-tert-butyl ester (0.986 g) was isolated in 96.1% yield. The mono-tert-butyl ester obtained was used to react with the peptide-resin [H-Lysyl(N-epsilon-Cbz)-Prolyl-{(2R)-2-Amino-3-cyclohexylpropanoyl}-{(2S)-2-Amino-3-cyclohexylpropanoyl}-DArginyl(guanidino-Tos)-OResin] and treated in the same way described in Example 2. The isomers were separated by RP-HPLC. 14.6 mg of the title isomer was obtained.

FAB+ MS: (M+H)+ =882. Amino Acid Anal: Lys (0.94), Pro (0.88), Cha (2.07), Arg (1.17).

EXAMPLE 149

{(R/S)-(2-Carboxyl)-3-phenylpropionyl}-Lysyl-Prolyl-{(2R)-2-Amino-3-cyclohexylpropanoyl}-{(2S)-2-Amino-3-cyclohexylpropanoyl}-DArginyl-OH This compound (8.6 mg) was another of the isomers obtained in Example 148.

FAB+ MS: (M+H)+ =882. Amino Acid Anal: Lys (0.96), Pro (0.99), Cha (1.98), Arg (1.05).

EXAMPLE 150

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Phenyl-2-phenethyl)amide FAB+ MS: (M+H)+ =890. Amino Acid Anal: MePhe (0.94), Lys (0.91), Pro (1.09), Cha (1.81).

EXAMPLE 151

(N-Methyl)Phenylalanyl-Lysyl-Prolyl-{(2R)-2-Amino-3-cyclohexylpropanoyl}-Phenylalanyl-N-{2-(Piperidin-1-yl)ethyl}amide FAB+ MS: (M+H)+ =815. Amino Acid Anal: Lys (0.95), Pro (1.01), Cha (0.98), Phe (1.04), MePhe (1.04).

EXAMPLE 152

(N-Methyl)Phenylalanyl-Lysyl-Prolyl-{(2R)-2-Amino-3-cyclohexylpropanoyl}-Phenylalanyl-N-{2-(4-Hydroxyphenyl)ethyl}amide FAB+ MS: (M+H)+ =824. Amino Acid Anal: Lys (0.95), Pro (1.00), Cha (0.99), Phe (1.04), MePhe (0.75).

EXAMPLE 153

N-Cbz-Lysyl-Prolyl-{(2R)-2-Amino-3-cyclohexylpropanoyl}-Phenylalanyl-DArginyl-OH Boc-Prolyl-{(2R)-2-Amino-3-cyclohexylpropanoyl}-Phenylalanyl-DArginyl(guanidino-Tos)-OResin (2.48 g) was prepared from the Boc-DArginyl(guanidino-Tos)-OResin (2.0 g, 0.44 mmole/g) according to the method described in Example 1. The peptide-resin (0.5 g) was treated with HF-anisole (Example 2) and the peptide was extracted with 50 mL of methanol. Methanol was removed by evaporation and the residue obtained was triturated with diethylether to yield a solid (158.5 mg) as the dihydrogen fluoride salt of Prolyl-{{(2R)-2-Amino-3-cyclohexylpropanoyl}-Phenylalanyl-DArginyl-OH. This was reacted with N-alpha-Cbz-N-epsilon-Boc-Lysine via the mixed anhydride method as described in Example 116. Half of the crude product (87.6 mg) was treated with 5 mL of 4N hydrochloric acid in dioxane for 1 hour and purified by the method described in Example 2 to yield 23.2 mg of the title compound.

FAB+ MS: (M+H)+ =834. Amino Acid Anal: Lys (1.02), Pro (0.95), Cha (1.05), Phe (1.05), Arg (0.99).

EXAMPLE 154

(N-Methyl)Phenylalanyl-Lysyl-Prolyl-{(2R)-2-Amino-3-cyclohexylpropanoyl}-Phenylalanyl-N-(3-Cyanoethyl)amide The compound (Boc-(N-Methyl)Phenylalanyl-Lysyl(N-epsilon-Boc)-Prolyl-{(2R)-2-Amino-3-cyclohexylpropanoyl}-Phenylalanyl-OH) of Example 4 (200 mg, 0.22 mmole) was reacted with 3-aminopropanenitrile (15.5 mg, 0.22 mmole) in THF via the mixed anhydride method as described in Example 116. A portion of the compound obtained (35 mg) was deprotected and purified to afford the title compound (16 mg, 43%).

FAB+ MS: (M+H)+ =757. Amino Acid Anal: MePhe (0.65), Lys (0.85), Pro (0.66), Cha (0.72), Phe (0.64).

EXAMPLE 155

(N-Methyl)Phenylalanyl-Lysyl-Prolyl-{(2R)-2-Amino-3-cyclohexylpropanoyl}-N-(2-Guanidinoethyl)-N-(2-Phenethyl)amide}

The compound was prepared in analogy to Example 42.

FAB+ MS: (M+H)+ =746. Amino Acid Anal: MePhe (0.85), Lys (0.99), Pro (1.01), Cha (0.84).

EXAMPLE 156

(N-Methyl)Phenylalanyl-Lysyl-Prolyl-{(2R)-2-Amino-3-cyclohexylpropanoyl}-N-(4-Aminobutyl)-N-(2-Phenethyl)amide N-Phenylacetyl-N'-Cbz-1,4-butanediamine was reduced by borane-tetrahydrofuran (THF) as described in Example 66. The obtained amine (96 mg, 2.6 mmole) was coupled with Boc-(N-Methyl)Phenylalanyl-Lysyl(N-epsilon-Boc)-Prolyl-{(2R)-2-Amino-3-cyclohexylpropanoyl}-OH (Example 3) (200 mg, 2.6 mmole) via the EDC and HOBT method (Example 3) to obtain Boc-(N-Methyl)Phenylalanyl-Lysyl(N-epsilon-Boc)-Prolyl-{(2R)-2 -Amino-3-cyclohexylpropanoyl}-N-(4-Cbz-Aminobutyl)-N-(2-Phenethyl)amide in quantitative yield. Hydrogenation gave the corresponding amine in 83% yield. Treatment of the compound (60 mg) with 50% trifluoroacetic acid in methylene chloride and then purification afforded the title compound (26 mg, 37%).

FAB+ MS: (M+H)+ =732. Amino Acid Anal: MePhe (0.89), Cha (0.84), Lys (1.00), Pro (1.00).

EXAMPLE 157

(N-Methyl)Phenylalanyl-Lysyl-Prolyl-{(2R)-2-Amino-3-cyclohexylpropanoyl}-N-{(1RS)-1-Benzyl-4-guanidinobutyl}amide The compound was prepared in analogy to Example 62, except the compound of Example 3 was used instead of the compound of Example 5.

FAB+ MS: (M+H)+ =760. Amino Acid Anal: MePhe (1.09), Lys (0.99), Pro (1.01), Cha (1.00).

EXAMPLE 158

(N-Methyl)Phenylalanyl-Lysyl-Prolyl-{(2R)-2-Amino-3-cyclohexylpropanoyl}-{(2R/S)-2-Amino-3-cyclohexylpropanoyl}-O-Benzyl Boc-(N-Methyl)Phenylalanyl-Lysyl(N-epsilon-Boc)-Prolyl-{(2R)-2-Amino-3-cyclohexylpropanoyl}-{(2R/S)-2-Amino-3-cyclohexylpropanoyl}-OH (Example 5) (91.1 mg, 0.1 mmole) was reacted with benzyl alcohol (12.4 μL, 0.12 mmole) in the presence of EDC (23 mg, 0.12 mmole) and N,N-dimethylaminopyridine (DMAP) (1.2 mg, 0.01 mmole) in 3 mL of methylene chloride. The peptide obtained was treated with 3 mL of 4N hydrochloric acid in dioxane and then purified on RP-HPLC. During the coupling procedure, the (2S)-2-Amino-3 -cyclohexylpropanoyl residue was racemized. The diastereomers were separable by RP-HPLC.

FAB+ MS: (M+H)+ =801. Amino Acid Anal: MePhe (1.46), Lys (0.97), Pro (1.03), Cha (1.94).

EXAMPLE 159

(N-Methyl)Phenylalanyl-Lysyl-Prolyl-{(2R)-2-Amino-3-cyclohexylpropanoyl}-{(2R/S)-2-Amino-3-cyclohexylpropanoyl}O-Benzyl The compound was one of the isomers described in Example 158.

FAB+ MS: (M+H)+ =801. Amino Acid Anal: MePhe (1.42), Lys (0.98), Pro (1.02), Cha (1.87).

EXAMPLE 160

(N-Methyl)Phenylalanyl-Lysyl-Prolyl-{(2R)-2-Amino-3-cyclohexylpropanoyl}-{(2R)-2-Amino-3-cyclohexylpropanoyl}-N-Benzylamide The compound was synthesized in the same manner as described in Example 5, except Boc-(2R)-2-Amino-3-cyclohexylpropanoic acid was used instead of Boc-(2S)-2-Amino-3-cyclohexylpropanoic acid.

FAB+ MS: (M+H)+ =800. Amino Acid Anal: MePhe (1.08), Lys (0.94), Pro (1.06), Cha (1.83).

EXAMPLE 161

2-Cyanocinnamoyl-Lysyl-Prolyl-{(2R)-2-Amino-3-cyclohexylpropanoyl}-Phenylalanyl-DArginyl-OH The title compound was prepared under standard solid phase conditions described in Examples 1 and 2, using commercially available alpha-cyanocinnamic acid.

FAB+ MS: (M+H)+ =855.

EXAMPLE 162

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Fluorene)amide FAB+ MS: (M+H)+ =874. Amino Acid Anal: MePhe (0.93), Lys (0.91), Pro (1.09), Cha (1.79).

EXAMPLE 163

(N-Methyl)Phenylalanyl-Lysyl-Prolyl-{(2R)-2-Amino-3-cyclohexylpropanoyl}-{(2S)-2-Amino-3-cyclohexylpropanoyl}-N-(N'-Phenyl)hydrazide The compound was prepared in analogy to Example 139.

FAB+ MS: (M+H)+ =801. Amino Acid Anal: Lys (0.97), Pro (1.02), Cha (2.00), MePhe (0.95).

EXAMPLE 164

(N-Methyl)Phenylalanyl-Lysyl-Prolyl-{(2R)-2-Amino-3-cyclohexylpropanoyl}-Phenylalanyl-N-{2-(4-Aminophenyl)ethyl}amide FAB+ MS: (M+H)+ =823. Amino Acid Anal: Lys (0.96), Pro (1.01), Cha (0.96), Phe (1.03), MePhe (0.76).

EXAMPLE 165

(N-Methyl)Phenylalanyl-Lysyl-Prolyl-{(2R)-2-Amino-3-cyclohexylpropanoyl}-Phenylalanyl-N-(2-Picolyl)amide FAB+ MS: (M+H)+ =795. Amino Acid Anal: Lys (0.95), Pro (0.99), Cha (0.92), Phe (1.04), MePhe (1.09).

EXAMPLE 166

(N-Methyl)Phenylalanyl-Lysyl-Prolyl-{(2R)-2-Amino-3-cyclohexylpropanoyl}-Phenylalanyl-Anilide The title compound was prepared from the Example 4 (100 mg, 0.11 mmole) and aniline (10 μL, 0.11 mmole) in THF via the mixed anhydride method described in Example 139. Pure title compound (57 mg, 57%) was isolated after RP-HPLC.

FAB+ MS: (M+H)+ =780. Amino Acid Anal: MePhe (0.89), Lys (1.00), Pro (0.98), Cha (1.00), Phe (1.02).

EXAMPLE 167

(N-Methyl)Phenylalanyl-Lysyl-Prolyl-{(2R)-2-Amino-3-cyclohexylpropanoyl}-N-(3-Guanidinopropyl)-N-(2-Phenethyl}amide The compound was prepared in analogy to Example 42.

FAB+ MS: (M+H)+ =760. Amino Acid Anal: MePhe (0.84), Lys (0.99), Pro (1.01), Cha (0.87).

EXAMPLE 168

Hydrocinnamoyl-Lysyl-Prolyl-{(2R)-2-Amino-3-cyclohexylpropanoyl}-Phenylalanyl-Ψ[CH$_2$N(Hydrocinnamoyl)]-DArginyl-OH The trifluoroacetic acid salt of H-Lysyl(N-epsilon-Cbz)-Prolyl-{(2R)-2-Amino-3-cyclohexylpropanoyl}-Phenylalanyl-Ψ[CH$_2$NH]-DArginyl(N-guanidino-Tos)-Merrifield Resin (Example 192) (0.54 g) was reacted with hydrocinnamoyl chloride (0.27 mL) in 15 mL of diisopropylethylamine (DIPEA) in methylene chloride. After HF treatment and lyophilization, 94.8 mg of crude product was obtained. This was purified by RP-HPLC to yield 15.3 mg of pure title compound.

FAB+ MS: (M+H)+ =950. Amino Acid Anal: Lys (1.00), Pro (1.02), Cha (0.92).

EXAMPLE 169

(N-Methyl)Phenylalanyl-Lysyl-Prolyl-{(2R)-2-Amino-3-cyclohexylpropanoyl}-N-(2-Naphthyl)amide FAB+ MS: (M+H)+ =642. Amino Acid Anal: MePhe (1.20), Lys (0.98), Pro (1.02), Cha (0.96).

EXAMPLE 170

(N-Methyl)Phenylalanyl-Lysyl-Prolyl-{(2R)-2-Amino-3-cyclohexylpropanoyl}-{(RS)-Phenylalanyl}-Benzyl ester The compound was prepared in analogy to Example 158. The two diastereomers were not separable.

FAB+ MS: (M+H)+ =795. Amino Acid Anal: MePhe (1.07), Lys (0.97), Pro (1.03), Cha (0.97), Phe (1.01).

EXAMPLE 171

(N-Methyl)Phenylalanyl-Lysyl-Prolyl-{(2S)-2-Amino-3-cyclohexylpropanoyl}-{(2R)-2-Amino-3-cyclohexylpropanoyl}-N-Benzylamide The compound was prepared by the method described in Example 5, except that the order of the chiralities of the two {2-Amino-3-cyclohexylpropanoyl} residues was reversed.

FAB+ MS: (M+H)+ =800. Amino Acid Anal: MePhe (0.99), Lys (0.94), Pro (1.06), Cha (1.77).

EXAMPLE 172

(N-Methyl)Phenylalanyl-Lysyl-Prolyl-{(2S)-2-Amino-3-cyclohexylpropanoyl}-{(2S)-2-Amino-3-cyclohexylpropanoyl}-N-Benzylamide The compound was synthesized by the method described in Example 5, except {Boc-(2S)-2-Amino-3-cyclohexylpropanoic acid} was used instead of {Boc-(2R)-2-Amino-3-cyclohexylpropanoic acid}.

FAB+ MS: (M+H)+ =800. Amino Acid Anal: MePhe (0.90), Lys (0.99), Pro (1.01), Cha (1.89).

EXAMPLE 173

{(R/S)-2-Cyano-3-phenylpropionyl}-Lysyl-Prolyl-{(2R)-2-Amino-3-cyclohexylpropanoyl}-{(2S)-2-Amino-3-cyclohexylpropanoyl}-DArginyl-OH (2RS)-2-Cyano-3-phenylpropionic acid was prepared by the hydrogenation (4 atm., r.t.) of alpha-cyanocinnamic acid (10.0 g, 57.7 mmol) in ethyl acetate (150 mL) over 5% palladium on carbon (0.5 g). The catalyst was removed by filtration, and rinsed with additional ethyl acetate. Upon concentration under reduced pressure, the product was obtained as an off-white solid (9.46 g, 54.0 mmol): mp 193°–194° C.; $^1$H NMR (CDCl$_3$, 300 MHz) δ7.45–7.20 (m, 5H), 5.17 (br s, 1 H), 3.79 (dd, J=6, 9 Hz, 1 H), 3.28 (ddd, J=6, 9, 31 Hz, 2 H); MS m/e 193 (M+NH$_4$)+.

The title peptide was prepared under standard solid phase peptide synthesis conditions described in Examples 1 and 2. The diasteromeric products were separated by peak shaving on reverse-phase HPLC.

FAB+ MS: (M+H)+ =863.

EXAMPLE 174

{(R/S)-2-Cyano-3-phenylpropionyl}-Lysyl-Prolyl-{(2R)-2-Amino-3-cyclohexylpropanoyl}-{(2S)-2-Amino-3-cyclohexylpropanoyl}-DArginyl-OH This product was one of the diastereomers of the compound described in Example 173. This diastereomer was obtained by HPLC separation as described above.

FAB+ MS: (M+H)+ =863.

EXAMPLE 175

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2,2-Diphenylethyl)amide FAB+ MS: (M+H)+ =890. Amino Acid Anal: MePhe (0.92), Lys (0.91), Pro (1.09), Cha (1.80).

EXAMPLE 176

(N-Methyl)Phenylalanyl-Lysyl-Prolyl-{(2R)-2-Amino-3-cyclohexylpropanoyl}-{(2S)-2-Amino-3-cyclohexylpropanoyl}-N-(N'-Benzyl)hydrazide The compound was prepared in analogy to Example 139.

FAB+ MS: (M+H)+ =815. Amino Acid Anal: Lys (0.96), Pro (1.04), Cha (1.96), MePhe (1.00).

EXAMPLE 177

(N-Methyl)Phenylalanyl-Lysyl-Prolyl-{(2R)-2-Amino-3-cyclohexylpropanoyl}-Phenylalanyl-N-(4-Carboxybenzyl)amide FAB+ MS: (M+H)+ =838. Amino Acid Anal: Lys (0.95), Pro (1.00), Cha and Aminomethylbenzoic Acid (1. 90), Phe (1.04), MePhe (0.76).

EXAMPLE 178

(N-Methyl)Phenylalanyl-Lysyl-Prolyl-{(2R)-2-Amino-3-cyclohexylpropanoyl}-Phenylalanyl-N-(3-Picolyl)amide FAB+ MS: (M+H)+ =795. Amino Acid Anal: Lys (1.24), Pro (0.97), Cha (1.40), Phe (1.03), MePhe (1.06).

EXAMPLE 179

4-[(N-Methyl)Phenylalanyl-Lysyl-Prolyl-{(2R)-2-Amino-3-cyclohexylpropanoyl}]-1-Phenylpiperazine FAB+ MS: (M+H)+ =702. Amino Acid Anal: MePhe (0.91), Lys (0.99), Pro (1.02), Cha (1.00).

EXAMPLE 180

(N-Methyl)Phenylalanyl-Lysyl-Prolyl-{(2R)-2-Amino-3-cyclohexylpropanoyl}-N-(5-Guanidinopentyl)-N-(2-Phenethyl)amide The compound was prepared in analogy to Example 42.

FAB+ MS: (M+H)+ =788. Amino Acid Anal: MePhe (0.83), Lys (1.00), Pro (1.00), Cha (0.81).

EXAMPLE 181

(S)-(+)-2-Phenylbutyryl-Lysyl-Prolyl-{(2R)-2-Amino-3-cyclohexylpropanoyl}-DArginyl-OH

FAB+ MS: (M+H)+ =698.

EXAMPLE 182

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(S)-1-Phenethyl}amide FAB+ MS: (M+H)+ =814. Amino Acid Anal: MePhe (1.08), Lys (0.99), Pro (1.01), Cha (2.03).

EXAMPLE 183

(N-Methyl)Phenylalanyl-Lysyl-Prolyl-{(2R)-2-Amino-3-cyclohexylpropanoyl}-{(2S)-2-Amino-3-cyclohexylpropanoyl}-2-Phenethyl ester FAB+ MS: (M+H)+ =815. Amino Acid Anal. MePhe (1.06), Lys (0.95), Pro (1.05), Cha (1.93).

EXAMPLE 184

(N-Methyl)Phenylalanyl-Lysyl-Prolyl-{(2R)-2-Amino-3-cyclohexylpropanoyl}-Phenylalanyl-N-{1-Cyclohexyl-1-cyclopropylmethyl}amide Commercially available 1,1-phenylcyclopropylmethylamine (0.11 g, 0.6 mmole) was hydrogenated with platinum-black (0.11 g) in 12 mL of acetic acid under 4 atmospheres of hydrogen to afford 1-cyclohexyl-1-cyclopropylmethylamine as an acetic acid salt in quantitative yield. Boc-(N-Methyl)Phenylalanyl-Lysyl(N-epsilon-Boc)-Prolyl-{(2R)-2-Amino-3-cyclohexylpropanoyl}-Phenylalanyl-OH (Example 4) (100 mg, 0.1 mmole) was reacted with the above amine (35 mg, 0.2 mmole) by the EDC and HOBT method described previously. Deprotection and purification gave 24 mg of the title compound.

FAB+ MS: (M+H)+ =840. Amino Acid Anal: MePhe (1.03), Lys (0.97), Pro (1.01), Cha (1.02), Phe (1.02).

EXAMPLE 185

(N-Methyl)Phenylalanyl-Lysyl-Prolyl-{(2R)-2-Amino-3-cyclohexylpropanoyl}-Phenylalanyl-N-(4-Amidinobutyl)amide The compound was prepared in analogy to Example 105.

FAB+ MS: (M+H)+ =802. Amino Acid Anal: MePhe (0.85), Lys (0.95), Pro (1.09), Cha (0.90), Phe (0.96).

EXAMPLE 186

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Benzyl-2-phenethyl)amide The compound was prepared in analogy to Example 60.

FAB+ MS: (M+H)+ =904. Amino Acid Anal: MePhe (0.96), Lys (0.91), Pro (1.09), Cha (1.80).

EXAMPLE 187

(N-Methyl)Phenylalanyl-Lysyl-Prolyl-{(2R)-2-Amino-3-cyclohexylpropanoyl}-Phenylalanyl-N-(N'-Phenyl)-hydrazide The compound was prepared in analogy to Example 139.

FAB+ MS: (M+H)+ =795. Amino Acid Anal: Lys (0.95), Pro (1.00), Cha (0.96), Phe (1.05), MePhe (1.04).

EXAMPLE 188

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Carboxybenzyl)amide FAB+ MS: (M+H)+ =844. Amino Acid Anal: Lys (0.98), Pro (1.02), Cha and Aminomethylbenzoic Acid (2.87), MePhe (0.80).

EXAMPLE 189

(N-Methyl)Phenylalanyl-Lysyl-Prolyl-{(2R)-2-Amino-3-cyclohexylpropanoyl}-Phenylalanyl-N-(4-Picolyl)amide FAB+ MS: (M+H)+ =795. Amino Acid Anal: Lys (1.02), Pro (1.00), Cha (0.94), Phe (0.97), MePhe (1.00).

EXAMPLE 190

1-Benzyl-4-[(N-Methyl)Phenylalanyl-Lysyl-Prolyl-{(2R)-2-Amino-3-cyclohexylpropanoyl}]-piperidine FAB+ MS: (M+H)+ =715. Amino Acid Anal: MePhe (0.90), Lys (1.00), Pro (1.03), Cha (0.98).

EXAMPLE 191

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Guanidinoethyl)amide The compound was prepared in analogy to Example 156.

FAB+ MS: (M+H)+ =795. Amino Acid Anal: MePhe (0.80), Lys (0.96), Pro (1.04), Cha (1 75).

EXAMPLE 192

{S(+)-2-Phenylbutyryl}-Lysyl-Prolyl-{(2R)-2-Amino-3-cyclohexylpropanoyl}-Phenylalanyly-Ψ(CH$_2$NH)-DArginyl-OH Boc-DArg(N-guanidino-Tos)-Merrifield resin (0.44 mmole/g 1.5 g) was placed in a solid phase peptide synthesis vessel and amino acids were attached to the resin sequentially in the following order: Boc-(2R)-2-Amino-3-cyclohexylpropanoic acid, Boc-Proline, and (N-alpha-Boc,N-epsilon-Cbz)Lysine.

Commercially available N-Boc-Phenylalanol (1.34 g, 5.34 mmole) was converted to N-Boc-Phenylalanal, according to the literature; Anhoury, M. L.; Crooy, P.; DeNeys, R.; Eliaers, J. J. Chem. Soc. Perkin 1 1974, 191; Hamada, Y.; Shioiri, T. Chem. Pharm. Bull. 1982, 30, 1921. After the sequence was stopped at agenda A-step 2, N-Boc-Phenylalanal (2.67 mmole) in 10 mL of DMF containing 0.1% glacial acetic acid was added, followed by sodium cyanoborohydride (0.503 g, 8.01 mmole). The reaction was allowed to proceed at room temperature for 1 hour. After the peptide resin obtained was washed with DMF (3×10 mL) and methylene chloride (3×10mL), the next synthetic protocol (Agenda A step 2) was initiated to yield the protected peptide resin: Trifluoroacetic acid salt of H-Lysyl(N-epsilon-Cbz)-Prolyl-{(2R)-2-Amino-3-cyclohexyl-propanoyl}-Phenylalanyl-Ψ(CH$_2$NH)-Arginyl(N-guanidino-Tos)-Merrifield Resin. Following the synthesis, the protected peptide resin was removed from the reaction vessel by washing the resin with DMF (3×20 mL) into a 30–60 mL sintered glass funnel, followed by washing the resin with methylene chloride (3×20 mL). The resin was dried at least five hours then weighed (2.21 g of peptide resin was obtained)

The above peptide-resin (0.54 g) was reacted with S-(+)-2-Phenylbutyric acid using the carbodiimide method as described in Example 1 and finally the peptide-resin was treated in the method described in Example 2 to afford 21.6 mg of the title compound from 72.4 mg of crude product.

FAB+ MS: (M+H)+ =832. Amino Acid Anal: Lys (0.93), Pro (1.07), Cha (0.93).

EXAMPLE 193

(N-Methyl)Phenylalanyl-Lysyl-Prolyl-{(2R)-2-Amino-3-cyclohexylpropanoyl}-{(2S)-2-Amino-3-cyclohexylpropanoyl}-Anilide FAB+ MS: (M+H)+ =786. Amino Acid Anal: MePhe (1.09), Lys (0.97), Pro (1.03), Cha (1.98).

EXAMPLE 194

(N-Methyl)Phenylalanyl-Lysyl-Prolyl-{(2R)-2-Amino-3-cyclohexylpropanoyl}-Phenylalanyl-2-Phenethyl ester FAB+ MS: (M+H)+ =809. Amino Acid Anal: MePhe (1.08), Lys (0.97), Pro (1.02), Cha (0.98), Phe (1.01).

EXAMPLE 195

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Cyclohexyl-1-cyclopropylmethyl)amide The compound was prepared in analogy to Example 184. Running the reaction on the same scale afforded 21 mg of the title compound.

FAB+ MS: (M+H)+ =846. Amino Acid Anal: MePhe (1.05), Lys (1.00), Pro (1.00), Cha (1.95).

EXAMPLE 196

(N-Methyl)Phenylalanyl-Lysyl-Prolyl-{(2R)-2-Amino-3-cyclohexylpropanoyl}-N-(Diphenylmethyl)amide FAB+ MS: (M+H)+ =723. Amino Acid Anal: MePhe (0.97), Lys (0.97), Pro (1.03), Cha (0.87).

EXAMPLE 197

(N-Methyl)Phenylalanyl-Lysyl-Prolyl-{(2R)-2-Amino-3-cyclohexylpropanoyl}-Phenylalanyl-N-(N'-Benzyl)-hydrazide The compound was prepared in analogy to Example 139.

FAB+ MS: (M+H)+ =809. Amino Acid Anal: Lys (0.95), Pro (0.99), Cha (0.96), Phe (1 06), MePhe (0.94).

EXAMPLE 198

(N-Methyl)Phenylalanyl-Lysyl-Prolyl-{(2R)-2-Amino-3-cyclohexylpropanoyl}-Phenylalanyl-N-(4-N,N-Dimethylaminobenzyl)amide FAB+ MS: (M+H)+ =837. Amino Acid Anal: Lys (0.96), Pro (1.01), Cha (0.96), Phe (1.03), MePhe (0.71).

EXAMPLE 199

(N-Methyl)Phenylalanyl-Lysyl-Prolyl-DArginyl-Phenylalanyl-N-(2-Picolyl)amide

FAB+ MS: (M+H)+ =798. Amino Acid Anal: Lys (1.00), Pro (0.92), Phe (0.99), MePhe (0.95), Arg (1.01).

EXAMPLE 200

(N-Methyl)Phenylalanyl-Lysyl-Prolyl-{(2R)-2-Amino-3-cyclohexylpropanoyl}-N-{2-(1-Piperidinyl)ethyl}amide FAB+ MS: (M+H)+ =668. Amino Acid Anal: MePhe (0.90), Lys (0.99), Pro (1.01), Cha (0.99).

EXAMPLE 201

(N-Methyl)Phenylalanyl-Lysyl-Prolyl-{(2R)-2-Amino-3-cyclohexylpropanoyl}-Phenylalanyl-N-(3-Guanidinopropyl)amide The compound was prepared in analogy to Example 42.

FAB+ MS: (M+H)+ =803. Amino Acid Anal: MePhe (0.82), Lys (0.99), Pro (1.01), Cha (0.90), Phe (0.84).

EXAMPLE 202

{5-Phenylvaleryl}-Lysyl-Prolyl-{(2R)-2-Amino-3-cyclohexylpropanoyl}-Phenylalanyl-Ψ(CH$_2$NH)-DArginyl-OH The compound was prepared in analogy to Example 192.

FAB+ MS: (M+H)+ =846. Amino Acid Anal; Lys (0.94), Pro (1.18), Cha (1.00).

EXAMPLE 203

(N-Methyl)Phenylalanyl-Lysyl-Prolyl-{(2R)-2-Amino-3-cyclohexylpropanoyl}-Phenylalanyl-N-{2-(4-Aminophenyl)ethyl}amide FAB+ MS: (M+H)+ =829. Amino Acid Anal: Lys (0.99), Pro (1.01), Cha (1.93), MePhe (1.06).

EXAMPLE 204

(N-Methyl)Phenylalanyl-Lysyl-Prolyl-{(2R)-2-Amino-3-cyclohexylpropanoyl}-Phenylalanyl-{(R)-(+)-2-Amino-3-phenyl-1-propanol}

FAB+ MS: (M+H)+ =838. Amino Acid Anal: MePhe (0.88), Lys (0.97), Pro (1.02), Cha (0.97), Phe (1.01).

EXAMPLE 205

(N-Methyl)Phenylalanyl-Lysyl-Prolyl-{(2R)-2-Amino-3-cyclohexylpropanoyl}-Phenylalanyl-N-{(2-Cyclohexyl-2-methyl)propyl}amide {1-(1-Phenylcyclopropyl)}methylamine (205 mg, 1.1 mmole) was hydrogenated using platinum-black (410 mg) in 20 mL of acetic acid under 4 atmospheres of hydrogen for 3 days. The same conditions were repeated 3 times to complete the reaction. 2-Cyclohexyl-2-methylpropylamine was isolated as an acetic acid salt in quantitative yield. This material (28.5 mg, 0.12 mmole) was coupled with Example 4 (100 mg, 0.1 mmole) by the EDC and HOBT method followed by deprotection and purification to afford pure title compound (51 mg, 47%).

FAB+ MS: (M+H)+ =842. Amino Acid Anal: MePhe (1.02), Lys (0.98), Pro (1.02), Cha (0.99), Phe (1.00).

EXAMPLE 206

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Naphthyl)amide FAB+ MS: (M+H)+ =836. Amino Acid Anal: MePhe (0.94), Lys (0.93), Pro (1.07), Cha (1.84).

EXAMPLE 207

1-Benzyl-4-[(N-Methyl)Phenylalanyl-Lysyl-Prolyl-{(2R)-2-Amino-3-cyclohexylpropanoyl}-(2S)-2-Amino-3-cyclohexylpropanoyl}]piperazine FAB+ MS: (M+H)+ =869. Amino Acid Anal: Lys (0.98), Pro (1.02), Cha (1.95), MePhe (0.87).

EXAMPLE 208

(N-Methyl)Phenylalanyl-Lysyl-Prolyl-{(2R)-2-Amino-3-cyclohexylpropanoyl}-Phenylalanyl-N-{(1-Benzimidazole)methyl}amide FAB+ MS: (M+H)+ =834. Amino Acid Anal: Lys (0.96), Pro (1.00), Cha (0.98), Phe (1.04), MePhe (0.73).

EXAMPLE 209

(N-Methyl)Phenylalanyl-Lysyl-Prolyl-DArginyl-Phenylalanyl-N-(3-Picolyl)amide

FAB+ MS: (M+H)+ =798. Amino Acid Anal: Lys (Present), Pro (0.88), Phe (0.99), MePhe (0.94), Arg (1.01).

EXAMPLE 210

(N-Methyl)Phenylalanyl-Lysyl-Prolyl-{(2R)-2-Amino-3-cyclohexylpropanoyl}-Phenylalanyl Methyl ester Boc-(N-Methyl)Phenylalanyl-Lysyl(N-epsilon-Boc)-Prolyl-{(2R)-2-Amino-3-cyclohexylpropanoyl}-Phenylalanyl-Methyl ester obtained as a precursor of Example 4, was deprotected using trifluoroacetic acid in methylene chloride and purified to obtain the title compound in 55% yield.

FAB+ MS: (M+H)+ =719. Amino Acid Anal: MePhe (0.90), Lys (0.99), Pro (1.03), Cha (0.98), Phe (0.99).

EXAMPLE 211

(N-Methyl)Phenylalanyl-Lysyl-Prolyl-{(2R)-2-Amino-3-cyclohexylpropanoyl}-Phenylalanyl-N-{(1S)-1-Phenethyl}amide FAB+ MS: (M+H)+ =808. Amino Acid Anal: MePhe (0.84), Lys (0.99), Pro (1.01), Cha (0.90), Phe (0.90).

EXAMPLE 212

(N-Methyl)Phenylalanyl-Lysyl-Prolyl-{(2R)-2-Amino-3-cyclohexylpropanoyl}-N-(4-Guanidinobutyl)-N-(2-Phenethyl)amide The amine (140 mg, 1.5 mmole), isolated as an intermediate of Example 156, was guanidinated and treated by the procedure described in Example 42 to afford pure title compound (40 mg, 25%).

FAB+ MS: (M+H)+ =774. Amino Acid Anal: MePhe (0.86), Lys (1.01), Pro (0.99), Cha (0.88).

EXAMPLE 213

Hydrocinnamoyl-Phenylalanyl-Prolyl-{(2R)-2-Amino-3-cyclohexylpropanoyl}-{(2S)-2-Amino-3-cyclohexylpropanoyl}-DArginyl-OH This compound is prepared using the techniques described in Examples 1 and 2.

EXAMPLE 214

Hydrocinnamoyl-Lysyl-Prolyl-{(2R)-2-Amino-3-cyclohexylpropanoyl}-N-{(1S)-1-Cyclohexylmethyl-2-guanidino)ethyl}amide FAB+ MS: (M+H)+ =709. Amino Acid Anal: Lys (0.98), Pro (1.02), Cha (0.90).

EXAMPLE 215

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(2-Cyclohexyl-2-methyl)propyl}amide The compound was prepared in analogy to Example 205.

FAB+ MS: (M+H)+ =848. Amino Acid Anal: MePhe (1.05), Lys (0.96), Pro (1.04), Cha (1.87).

EXAMPLE 216

(N-Methyl)Phenylalanyl-Lysyl-Prolyl-{(2R)-2-Amino-3-cyclohexylpropanoyl}-N-(2-Naphthyl)amide FAB+ MS: (M+H)+ =737. Amino Acid Anal: MePhe (0.95), Lys (0.98), Pro (1.02), Cha (0.94).

EXAMPLE 217

4-Benzyl-1-[(N-Methyl)Phenylalanyl-Lysyl-Prolyl-{(2R)-2-Amino-3-cyclohexylpropanoyl}-{(2S)-2-Amino-3-cyclohexylpropanoyl)}]piperidine FAB+ MS: (M+H)+ =868. Amino Acid Anal: Lys (1.00), Pro (1.00), Cha (2.03), MePhe (1.34).

EXAMPLE 218

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Amidinoethyl)amide The compound was prepared in analogy to Example 105.

FAB+ MS: (M+H)+ =780. Amino Acid Anal: MePhe (0.75), Lys (0.96), Pro (1.04), Cha (1.82).

EXAMPLE 219

(N-Methyl)Phenylalanyl-Lysyl-Prolyl-{(2R)-2-Amino-3-cyclohexylpropanoyl}-Phenylalanyl-N-Cyclohexylamide FAB+ MS: (M+H)+ =786. Amino Acid Anal: MePhe (0.85), Lys (0.98), Pro (1.02), Cha (0.90), Phe (0.89).

EXAMPLE 220

(N-Methyl)Phenylalanyl-Lysyl-Prolyl-{(2R)-2-Amino-3-cyclohexylpropanoyl}-N-(6-Aminohexyl)-N-(2-Phenethyl)amide The compound was prepared in analogy to Example 156.

FAB+ MS: (M+H)+ =760. Amino Acid Anal: MePhe (0.70), Lys (1.00), Pro (1 00), Cha (0.84).

EXAMPLE 221

Hydrocinnamoyl-Arginyl-Prolyl-{(2R)-2-Amino-3-cyclohexylpropanoyl}-{(2S)-2-Amino-3-cyclohexylpropanoyl}-DArginyl-OH This compound is prepared using the techniques described in Examples 1 and 2.

EXAMPLE 222

(N-Methyl)Phenylalanyl-Lysyl-Prolyl-{(2R)-2-Amino-3-cyclohexylpropanoyl}-{(2S)-2-Amino-3-cyclohexylpropanoyl}-N-{2-(1-Piperidine)ethyl}amide FAB+ MS: (M+H)+ =821. Amino Acid Anal: Lys (0.98), Pro (1.02), Cha (1.98), MePhe (0.99).

EXAMPLE 223

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Cyanoethyl)amide The compound was prepared in analogy to Example 154.

FAB+ MS: (M+H)+ =763. Amino Acid Anal: MePhe (0.77), Lys (0.97), Pro (1.03), Cha (1.93).

EXAMPLE 224

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Indan)amide FAB+ MS: (M+H)+ =826. Amino Acid Anal: MePhe (0.82), Lys (0.99), Pro (1.01), Cha (1.83).

EXAMPLE 225

(N-Methyl)Phenylalanyl-Lysyl-Prolyl-{(2R)-2-Amino-3-cyclohexylpropanoyl}-N-3-Aminopropyl-N-2-Phenethylamide The compound was prepared in analogy to Example 156.

FAB+ MS: (M+H)+ =718. Amino Acid Anal: MePhe (0.83), Lys (0.98), Pro (1.02), Cha (0.91).

EXAMPLE 226

Hydrocinnamoyl-Lysyl-(N-Methyl)Alanyl-{(2R)-2-Amino-3-cyclohexylpropanoyl}-(2S)-2-Amino-3-cyclohexylpropanoyl}-DArginyl-OH This compound is prepared using the techniques described in Examples 1 and 2.

EXAMPLE 227

Hydrocinnamoyl-Lysyl-prolyl-{(2R)-2-Amino-3-cyclohexylpropanoyl}-(2S)-2-Amino-3-cyclohexylpropanoyl}-(N-Phenethyl)DArginyl-OH After the sequence is stopped at Agenda A-step 2, commercially available phenylacetaldehyde (3.5 equivalent mole) in dimethylformamide containing 0.1% glacial acetic acid is added followed by sodium cyanoborohydride (10 equivalent mole). The reaction is allowed to proceed at room temperature for 1 hour. After the peptide resin obtained is washed with dimethylformamide (3×) and methylene chloride (3×), the next synthetic protocol (Example 1, Agenda A step 2) is initiated. The peptide-resin is then treated as described in Example 2.

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A compound of the formula

A-Lys-Pro-(D-Cha)-G-J-L wherein

D-Cha is D-cyclohexylalanyl;

A is $R_1$-$R_2$-$R_3$;

G, is absent or is $R_{13}$-$R_{14}$-$R_{15}$;

J is $R_{16}$-$R_{17}$-$R_{18}$; and

L is $R_{19}$;

where (a) $R_1$ is selected from the group consisting of lower alkyl, alkoxy, aryl, aryloxy, arylalkenyl, arylalkoxy, carboxyalkyl, cyano, cyanoalkyl, amino, aminoalkyl, alkylamino, arylalkyl, aroyl, haloalkyl, hydroxyalkyl, and hydrogen;

(b) $R_2$ is selected from the group consisting of $CR_{99}R_{100}$ and oxygen, with the proviso that when $R_2$ is oxygen, $R_1$ is aryl, lower alkyl or arylalkyl;

(c) $R_3$ is selected from C=O, $CH_2$, and —$CH_2$-C(O)— with the proviso that when $R_3$ is $CH_2$, the $R_2$ cannot be oxygen;

(d) $R_{13}$ is $CH_2$ or $NR_{50}$ where $R_{50}$ is hydrogen, lower alkyl or arylalkyl;

(e) $R_{14}$ is $CR_{230}R_{231}$;

(f) $R_{15}$ and $R_{18}$ are independently selected from C=O, $CH_2$, and —$CH_2C(O)$—;

(g) $R_{16}$ is selected from the group consisting of oxygen, $NR_{50}$, and $CH_2$ where $R_{50}$ is as defined above, with the proviso that when $R_{15}$ is $C=O$ and $R_{16}$ is oxygen, then $R_{17}$, $R_{18}$, and $R_{19}$ taken together represent hydrogen, lower alkyl, aryl, or arylalkyl;

(h) $R_{17}$ is $CR_{301}R_{302}$;

(i) $R_{19}$ is selected from OH and CN, with the proviso that when $R_{18}$ is $C=O$ then $R_{19}$ is OH;

(j) $R_{99}$ is selected from the group consisting of hydrogen, arylalkyl, aryl, arylalkenyl, lower alkyl, carboxyl, alkoxy, hydroxyalkyl, and hydroxy;

(k) $R_{100}$ is selected from the group consisting of hydrogen, arylalkyl, and lower alkyl;

(l) $R_{230}$ is selected from the group consisting of lower alkyl, arylalkyl, guanidinoalkyl, and (cycloalkyl)alkyl, with the proviso that when J-L represent an L-arginyl residue, the arylalkyl value of $R_{230}$ is limited to benzyl;

(m) $R_{231}$ and $R_{302}$ are independently selected from the group consisting of hydrogen, arylalkyl, alkenyl, and lower alkyl, with the proviso that when J-L represent an L-arginyl residue, the arylalkyl value of $R_{231}$ is limited to benzyl; and (n) $R_{301}$ is selected from the group consisting of hydrogen, lower alkyl, aminoalkyl, arylalkyl, (cycloalkyl)alkyl, and guanidinoalkyl;

all of the foregoing with the provisos that when A is an α-amino acid residue, then $R_{18}$-$R_{19}$ cannot be —COOH and when $R_{18}$-$R_{19}$ is COOH, then A cannot be an α-amino acid residue.

2. A compound as defined by claim 1 wherein $R_{13}$ and $R_{16}$ are independently selected from NH, N(Lower alkyl) and N(arylalkyl).

3. A compound of the formula

A-Lys-Pro-(D-Cha)-G-J-L wherein

D-Cha is D-cyclohexylalanyl;

A is $R_1$-$R_2$-$R_3$;

G is absent or is $R_{13}$-$R_{14}$-$R_{15}$;

J is $R_{16}$-$R_{17}$-$R_{18}$; and

L is $R_{19}$;

where (a) $R_1$ is selected from the group consisting of
lower alkyl,
alkoxy,
aryl,
aryloxy,
arylalkenyl,
arylalkoxy,
carboxyalkyl,
cyano,
cyanoalkyl,
amino,
aminoalkyl,
alkylamino,
arylalkyl,
aroyl,
haloalkyl,
hydroxyalkyl, and
hydrogen;

(b) $R_2$ is selected from the group consisting of $>R_{99}C_{100}$ and oxygen; with the proviso that when $R_2$ is oxygen, $R_1$ is aryl, lower alkyl, or arylalkyl;

(c) $R_3$ is selected from $>C=O$ and $>CH_2$ with the proviso that when $R_3$ is $>CH_2$, then $R_2$ may not be oxygen;

(d) $R_{13}$ is $>CH_2$ or $>NR_{50}$ where $R_{50}$ is hydrogen, lower alkyl or arylalkyl;

(e) $R_{14}$ is $>CR_{230}R_{231}$;

(f) $R_{15}$ is $>C=O$ or $>CH_2$;

(g) $R_{16}$ is selected from the group consisting of oxygen, $>CH_2$ and $>NR_{50}$ where $R_{50}$ is as defined above, with the proviso that when $R_{15}$ is $>C=O$ and $R_{16}$ is oxygen, then $R_{17}$, $R_{18}$ and $R_{19}$ taken together represent hydrogen, lower alkyl, aryl, or arylalkyl;

(h) $R_{17}$ is $>CR_{301}R_{302}$;

(i) $R_{18}$ is $>C=O$ or $>CH_2$;

(j) $R_{19}$ is OH or CN, with the proviso that when $R_{18}$ is $>C=O$, then $R_{19}$ is OH;

(k) $R_{99}$ is selected from the group consisting of
hydrogen,
arylalkyl,
aryl,
arylalkenyl,
lower alkyl,
carboxyl,
alkoxy,
hydroxyalkyl, and
hydroxy;

(l) $R_{100}$ is selected from the group consisting of
hydrogen,
arylalkyl, and
lower alkyl;

(m) $R_{230}$ is selected from the group consisting of
lower alkyl,
arylalkyl,
guanidinoalkyl, and
(cycloalkyl)alkyl, with the proviso that when J-L represents an L-arginyl residue, the arylalkyl value of $R_{230}$ is limited to benzyl;

(n) $R_{231}$ and $R_{302}$ are independently selected from the
group consisting of
hydrogen,
arylalkyl,
alkenyl, and
lower alkyl,
with the proviso that when J-L represents an L-arginyl, the arylalkyl value of $R_{231}$ is limited to benzyl;

(o) $R_{301}$ is selected from the group consisting of
hydrogen,
lower alkyl,
aminoalkyl,
arylalkyl,
(cycloalkyl)alkyl, and
guanidinoalkyl;

all of the foregoing with the proviso that when A is an α-amino acid residue, then $R_{18}$-$R_{19}$, taken together, may not be —COOH, and when $R_{18}$-$R_{19}$, taken together, are —COOH, then A may not be an α-amino acid residue.

4. A compound as defined by claim 1 wherein $R_{99}$ is selected from arylalkyl or arylalkenyl.

5. A compound of the formula

A-Lys-Pro-(D-Cha)-G-J-L wherein

D-Cha is D-cyclohexylalanyl;

A is $R_1$-$R_2$-$R_3$;
G is absent or is $R_{13}$-$R_{14}$-$R_{15}$;
J is $R_{16}$-$R_{17}$-$R_{18}$; and
L is $R_{19}$;
  where
  (a) $R_1$ is selected from the group consisting of
    lower alkyl,
    alkoxy,
    aryl,
    aryloxy,
    arylalkenyl,
    arylalkoxy,
    carboxyalkyl,
    cyano,
    cyanoalkyl,
    amino,
    aminoalkyl,
    alkylamino,
    arylalkyl,
    aroyl,
    haloalkyl,
    hydroxyalkyl, and
    hydrogen;
  (b) $R_2$ is selected from the group consisting of $R_{99}C_{100}$ and oxygen, with the proviso that when $R_2$ is oxygen, $R_1$ is aryl, lower alkyl, or arylalkyl;
  (c) $R_3$ is selected from C=O and $CH_2$ with the proviso that when $R_3$ is $CH_2$, then $R_2$ may not be oxygen;
  (d) $R_{13}$ is $CH_2$ or $NR_{50}$ where $R_{50}$ is hydrogen, lower alkyl or arylalkyl;
  (e) $R_{14}$ is $CR_{230}R_{231}$;
  (f) $R_{15}$ is C=O or $CH_2$;
  (g) $R_{16}$ is selected from the group consisting of oxygen, $CH_2$ and $NR_{50}$ where $R_{50}$ is as defined above, with the proviso that when $R_{15}$ is C=O and $R_{16}$ is oxygen, then $R_{17}$, $R_{18}$ and $R_{19}$ taken together represent hydrogen, lower alkyl, aryl, or arylalkyl;
  (h) $R_{17}$ is $CR_{301}R_{302}$;
  (i) $R_{18}$ is C=O or $CH_2$;
  (j) $R_{19}$ is OH or CN, with the proviso that when $R_{18}$ is C=O, then $R_{19}$ is OH;
  (k) $R_{99}$ is selected from the group consisting of
    hydrogen,
    arylalkyl,
    aryl,
    arylalkenyl,
    lower alkyl,
    carboxyl,
    alkoxy,
    hydroxyalkyl, and
    hydroxy;
  $R_{100}$ is selected from the group consisting of
    hydrogen,
    arylalkyl, and
    lower alkyl;
  (m) $R_{230}$ is
    guanidinoalkyl, or
    arylalkyl,
    with the proviso that arylalkyl at $R_{230}$ is benzyl when
    J-L represents an L-Arginyl residue,;
  (n) $R_{231}$ and $R_{302}$ are independently selected from the
    group consisting of
    hydrogen,
    arylalkyl,
    alkenyl, and
    lower alkyl,
    with the proviso that when J-L represents an L-arginyl, the arylalkyl value of $R_{231}$ is limited to benzyl;
  (o) $R_{301}$ is selected from the group consisting of
    hydrogen,
    lower alkyl,
    aminoalkyl,
    arylalkyl,
    (cycloalkyl)alkyl, and
    guanidinoalkyl;
  all of the foregoing with the proviso that when A is an α-amino acid residue, then $R_{18}$–$R_{19}$, taken together, may not be —COOH, and when $R_{18}$–$R_{19}$, taken together, are —COOH, then A may not be an α-amino acid residue.

6. A compound of the formula

A-Lys-Pro-(D-Cha)-G-J-L wherein
  D-Cha is D-cyclohexylalanyl;
  A is $R_1$-$R_2$-$R_3$;
  G is absent or is $R_{13}$-$R_{14}$-$R_{15}$;
  J is $R_{16}$-$R_{17}$-$R_{18}$; and
  L is $R_{19}$;
  where
  (a) $R_1$ is selected from the group consisting of
    lower alkyl,
    alkoxy,
    aryl,
    aryloxy,
    arylalkenyl,
    arylalkoxy,
    carboxyalkyl,
    cyano,
    cyanoalkyl,
    amino,
    aminoalkyl,
    alkylamino,
    arylalkyl,
    aroyl,
    haloalkyl,
    hydroxyalkyl, and
    hydrogen;
  (b) $R_2$ is selected from the group consisting of $R_{99}C_{100}$ and oxygen, with the proviso that when $R_2$ is oxygen, $R_1$ is aryl, lower alkyl, or arylalkyl;
  (c) $R_3$ is selected from C=O and $CH_2$ with the proviso that when $R_3$ is $CH_2$, then $R_2$ may not be oxygen;
  (d) $R_{13}$ is $CH_2$ or $NR_{50}$ where $R_{50}$ is hydrogen, lower alkyl or arylalkyl;
  (e) $R_{14}$ is $CR_{230}R_{231}$;
  (f) $R_{15}$ is C=O or $CH_2$;
  (g) $R_{16}$ is selected from the group consisting of oxygen, $CH_2$ and $NR_{50}$ where $R_{50}$ is as defined above, with the proviso that when $R_{15}$ is C=O and $R_{16}$ is oxygen, then $R_{17}$, $R_{18}$ and $R_{19}$ taken together represent hydrogen, lower alkyl, aryl, or arylalkyl;
  (h) $R_{17}$ is $CR_{301}R_{302}$;
  (i) $R_{18}$ is C=O or $CH_2$;
  (j) $R_{19}$ is OH or CN, with the proviso that when $R_{18}$ is C=O, then $R_{19}$ is OH;
  (k) $R_{99}$ is selected from the group consisting of hydrogen,
arylalkyl,
aryl,
arylalkenyl,
lower alkyl,
carboxyl,
alkoxy,
hydroxyalkyl, and
hydroxy;

(l) $R_{100}$ is selected from the group consisting of
hydrogen,
arylalkyl, and
lower alkyl;

(m) $R_{230}$ is selected from the group consisting of
lower alkyl,
arylalkyl,
guanidinoalkyl, and
(cycloalkyl)alkyl,
with the proviso that when J–L represents an L-arginyl residue, the arylalkyl value of $R_{230}$ is limited to benzyl;

(n) $R_{231}$ and $R_{302}$ are independently selected from the group consisting of
hydrogen,
arylalkyl,
alkenyl, and
lower alkyl,
with the proviso that when J–L represents an L-arginyl, the arylalkyl value of $R_{231}$ is limited to benzyl;

(o) $R_{301}$ is
(cycloalkyl)alkyl,
guanidinoalkyl, or
arylalkyl;

all of the foregoing with the proviso that when A is an α-amino acid residue, then $R_{18}$–$R_{19}$, taken together, may not be —COOH, and when $R_{18}$–$R_{19}$, taken together, are —COOH, then A may not be an α-amino acid residue.

7. A compound as defined by claim 1 wherein the preferred chirality, if present, of R17 is of D-configuration at the alpha position of amino acid residue J.

8. A compound as defined by claim 1 wherein A taken together is (N-Methyl)Phenylalanyl.

9. A compound selected from the group consisting of:
(N-Methyl)Phenylalanyl-Lysyl-Prolyl-{(2R)-2-Amino-3-cyclohexylpropanoyl}-N-{(1RS)-1-(Cyclohexylmethyl)-3-(guanidino)propyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Phenylpropyl)amide;
(N-Methyl)Phenylalanyl-Lysyl-Prolyl-{(2R)-2-Amino-3-cyclohexylpropanoyl}-Phenylalanyl-N-(3-Nitrobenzyl)amide;
(N-Methyl)Phenylalanyl-Lysyl-Prolyl-{(2R)-2-Amino-3-cyclohexylpropanoyl}-N-{(1S)-1-Cyclohexylmethyl-2-[N-(4-Guanidinobutyryl)amido]ethyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Naphthyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(5-Guanidinopentyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Naphthyl)methylamide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Guanidinopropyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1RS)-(1-Benzyl)-4-phenylbutyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1-Phenyl)cyclopropylmethyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1R/S)-1-Benzyl-4-guanidinobutyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{(4-N,N-Dimethylamino)benzyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Guanidinobutyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-Benzylamide;
(N-Methyl)Phenylalanyl-Lysyl-Prolyl-{(2R)-2-Amino-3-cyclohexylpropanoyl}-N-{(1S)-1-Cyclohexylmethyl-2-guanidinoethyl}amide;
(N-Methyl)Phenylalanyl-Lysyl-Prolyl-{(2R)-2-Amino-3-cyclohexylpropanoyl}-Phenylalanyl-N-{(1-Phenyl)cyclopropylmethyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-Diphenylmethylamide;
(N-Methyl)Phenylalanyl-Lysyl-Prolyl-{(2R)-2-Amino-3-cyclohexylpropanoyl}-Phenylalanyl-N-(2-Amidinoethyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Phenethyl)amide;
(N-Methyl)Phenylalanyl-Lysyl-Prolyl-{(2R)-2-Amino-3-cyclohexylpropanoyl}-{(2S)-2-Amino-3 -cyclohexylpropanoyl}-N-(2,2-Dimethyl-2-Phenethyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{(1RS)-1-Benzyl-3-phenylpropyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Nitrobenzyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Picolyl)amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{2-(4-Hydroxyphenyl)ethyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(3-Picolyl)amide;
(N-Methyl)Phenylalanyl-Lysyl-Prolyl-{(2R)-2-Amino-3-cyclohexylpropanoyl}-Phenylalanyl-N-Benzylamide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-{2-(Indol-3-yl)ethyl}amide;
(N-Methyl)Phenylalanyl-Lysyl-Prolyl-{(2R)-2-Amino-3-cyclohexylpropanoyl}-{(2S)-2-Amino-3-cyclohexylpropanoyl}-N-(Benzyloxy)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(4-Picolyl)amide;

(N-Methyl)Phenylalanyl-Lysyl-Prolyl-{(2R)-2-Amino-3-cyclohexylpropanoyl}-N-{(1RS)-1-Benzyl-4-guanidinobutyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Fluorene)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(N'-Phenyl)hydrazide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(S)-1-Phenethyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(2-Guanidinoethyl)amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-(1-Cyclohexyl-1-cyclopropylmethyl)amide;

(N-Methyl)Phenylalanyl-Lysyl-Prolyl-{(2R)-2-Amino-3-cyclohexylpropanoyl}-Phenylalanyl-N-{2-(4-Aminophenyl)ethyl}amide;

1-Benzyl-4-[(N-Methyl)Phenylalanyl-Lysyl-Prolyl-{(2R)-2-Amino-3-cyclohexylpropanoyl}-{(2S)-2-Amino-3-cyclohexylpropanoyl}]piperazine;

(N-Methyl)Phenylalanyl-Lysyl-Prolyl-{(2R)-2-Amino-3-cyclohexylpropanoyl}-Phenylalanyl-N-{(1S)-1-Phenethyl}amide;

(N-Methyl)Phenylalanyl-Lysyl-Prolyl-{(2R)-2-Amino-3-cyclohexylpropanoyl}-{(2S)-2-Amino-3-cyclohexylpropanoyl}-N-{(2-Cyclohexyl-2-methyl)propyl}amide;

and (N-Methyl)Phenylalanyl-Lysyl-Prolyl-{(2R)-2-Amino-3-cyclohexylpropanyl}-{(2S)-2-Amino-3-cyclohexylpropanoyl}-N-(2-Amidinoethyl)amide.

10. A compound as defined by claim 1 wherein J is D-arginyl.

11. A compound selected from the group consisting of:

(S)-(+)-2-Phenylbutyryl-Lysyl-Prolyl-{(2R)-2-Amino-3-cyclohexylpropanoyl}-{(2S)-2-Amino-3-cyclohexylpropanoyl}-DArginyl-OH;

{(R)-(-)-2-Phenylbutyryl}-Lysyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-Phenylalanyl-DArginyl-OH;

{R(-)-3-Phenylbutyryl}-Lysyl-Prolyl-{(2R)-2-Amino-3-cyclohexylpropanoyl}-{(2S)-2-Amino-3-cyclohexylpropanoyl}-DArginyl-OH;

{(2-Benzyl-2-cyano-3-phenyl)propionyl}-Lysyl-Prolyl-{(2R)-2-Amino-3-cyclohexylpropanoyl}-{(2S)-2-Amino-3-cyclohexylpropanoyl}-DArginyl-OH;

{(R/S)-3-Amino-3-phenylpropionyl}-Lysyl-Prolyl-{(2R)-2-Amino-3-cyclohexylpropanoyl}-Phenylalanyl-DArginyl-OH;

{S(+)-3-Phenylbutyryl}-Lysyl-Prolyl-{(2R)-2-Amino-3-cyclohexylpropanoyl}-{(2S)-2-Amino-3-cyclohexylpropanoyl}-DArginyl-OH;

[2-{(S)-(+)-Methoxy}-2-phenylacetyl]-Lysyl-Prolyl-{(2R)-2-Amino-3-cyclohexylpropanoyl}-Phenylalanyl-DArginyl-OH;

N-Phenylacetyl-Lysyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-{(2S)-2-Amino-3-cyclohexylpropanoyl}-DArginyl-OH;

{(3S)-Phenyllactyl}-Lysyl-Prolyl-{(2R)-2-Amino-3-cyclohexylpropanoyl}-Phenylalanyl-DArginyl-OH;

Phenoxyacetyl-Lysyl-Prolyl-{(2R)-2-Amino-3-cyclohexylpropanoyl}-Phenylalanyl-DArginyl-OH;

{(1-Phenyl-1-cyclopentane)carbonyl}-Lysyl-Prolyl-{(2R)-2-Amino-3-cyclohexylpropanoyl}-Phenylalanyl-DArginyl-OH;

{(2RS)-2-Cyano-3-phenylpropionyl}-Lysyl-Prolyl-{(2R)-2-Amino-3-cyclohexylpropanoyl}-Phenylalanyl-DArginyl-OH;

{(R/S)-(2-Carboxyl)-3-phenylpropionyl}-Lysyl-Prolyl-{(2R)-2-Amino-3-cyclohexylpropanoyl}-{(2S)-2-Amino-3-cyclohexylpropanoyl}-DArginyl-OH;

{(R/S)-2-Cyano-3-phenylpropionyl}-Lysyl-Prolyl-{(2R)-2-Amino-3-cyclohexylpropanoyl}-{(2S)-2-Amino-3-cyclohexylpropanoyl}-DArginyl-OH; and {(R/S)-2-Cyano-3-phenylpropionyl}-Lysyl-Prolyl-{(2R)-2-Amino-3-cyclohexylpropanoyl}-{(2S)-2-Amino-3-cyclohexylpropanoyl}-DArginyl-OH.

12. A compound as defined by claim 1 wherein A is Hydrocinnamoyl.

13. A compound selected from the group consisting of:

Hydrocinnamoyl-Lysyl-{(3R/S)-1,2,3,4-Tetrahydroisoquinolin-3-carbonyl}-{(2R)-2-Amino-3-cyclohexylpropanoyl}-{(2S)-2-Amino-3-cyclohexylpropanoyl}-DArginyl-OH;

Hydrocinnamoyl-Norleucyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-{(2S)-2-Amino-3-cyclohexylpropanoyl}-DPhenylalanyl-OH;

Hydrocinnamoyl-Phenylalanyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-Prolyl-{(2R)-2-Amino-3-cyclohexylpropanoyl}-N-{(1S)-1-Cyclohexylmethyl-2-guanidino)ethyl}amide;

Hydrocinnamoyl-Arginyl-Prolyl-{(2R)-2-Amino-3-cyclohexylpropanoyl}-{(2S)-2-Amino-3-cyclohexylpropanoyl}-DArginyl-OH;

Hydrocinnamoyl-Lysyl-(N-Methyl)Alanyl-{(2R)-2-Amino-3-cyclohexylpropanoyl}-{(2S)-2-Amino-3-cyclohexylpropanoyl}-DArginyl-OH and Hydrocinnamoyl-Lysyl-Prolyl-{(2R)-2-Amino-3-cyclohexylpropanoyl}-(2S)-2-Amino-3-cyclohexylpropanoyl}-(N-Phenethyl)DArginyl-OH.

* * * * *

UNITED STATES PATENT AND TRADEMARK OFFICE
CERTIFICATE OF CORRECTION

PATENT NO. : 5,190,922     Page 1 of 3
DATED      : March 2, 1993
INVENTOR(S): Jay R. Luly; Megumi Kawai; Paul E. Wiedeman It is certified that error appears in the above-identified patent and that said Letters Patent is hereby corrected as shown below:

COLUMN 2, LINE 56:   Replace "B iS" with --B is--

COLUMN 3, LINE 22:   REPLACE "Consisting" with --consisting--.

COLUMN 7, LINE 34:   Replace "1butenyl" with --1-butenyl--

COLUMN 9, LINE 20:   Replace "50-" with -- 5- --

COLUMN 11, LINE 30:  Replace "3cyclohexylpropanoyl]" with
                     --3-cyclohexylpropanoyl]--

COLUMN 11, LINE 39:  Replace "3cyclohexylpropanoyl]" with
                     --3-cyclohexylpropanoyl]--

COLUMN 12, LINE 5:   Replace "-N-]" with -- -N-[ --

COLUMN 12, LINE 6:   Replace "thy12-" with --thy-2- --

COLUMN 12, LINE 8:   Replace "-N-](1-" with -- -N-[(1- --

COLUMN 12, LINE 25:  Replace "ylpropanoyl]-N-]"with
                     --ylpropanoyl]-N-[ --.

COLUMN 12, LINE 34:  Replace "ylpropanoyl]-N-(" with
                     --ylpropanoyl]-N-[ --.

COLUMN 13, LINE 24:  Replace "3cyclohexylpropanoyl]" with
                     -- 3-cyclohexylpropanoyl] --.

COLUMN 13, LINE 25:  Replace "$(R)-(-)" with --R(-)--.

UNITED STATES PATENT AND TRADEMARK OFFICE
CERTIFICATE OF CORRECTION

PATENT NO. : 5,190,922

DATED : March 2, 1993

INVENTOR(S) : Jay R. Luly, Megumi Kawai, Paul E. Wiedman.

It is certified that error appears in the above-identified patent and that said Letters Patent is hereby corrected as shown below:

COLUMN 13, LINE 29: Replace "Hydrocinnamoul" with --Hydrocinnamoyl--.

COLUMN 13, LINE 34: Replace "propionyl)" with --propionyl]--.

COLUMN 13, LINE 37: Replace "](R/S)-3-Amino-3-phenylpropionyl)" with --(R/S)-3-Amino-3-phenylpropionyl]--.

COLUMN 13, LINE 40: Replace "[S(+)-3-phenylbutyryl) with --[S(+)-3-Phenylbutyryl]--.

COLUMN 14, LINE 10: Replace "-Lysyl-]" with -- -Lysyl-[ --.

COLUMN 14, LINE 24: Replace "3cy-" with --3-cy- --.

COLUMN 14, LINE 25: Replace "-N-]" with -- -N-[ --.

COLUMN 14, LINE 26: Replace "ethyl)" with --ethyl]--

COLUMN 17, LINE 38: Replace "$C_5a$" with --$C_{5a}$--

COLUMN 17, LINE 41: Replace "$C_5a$" with --$C_{5a}$--

COLUMN 18, LINE 60: Replace "($N_G$)" with --($N^G$)--

COLUMN 22, LINE 19: Replace "3-carbonyl)-]" with --3-carbonyl)-[--

COLUMN 22, LINE 59: Replace "N-Odime" with --N,O-dime--

COLUMN 25, LINE 10: Replace "2" with --21--

COLUMN 25, LINE 14: Replace "2Phenylbutyl" with --2-Phenylbutyl--

UNITED STATES PATENT AND TRADEMARK OFFICE
CERTIFICATE OF CORRECTION

PATENT NO. : 5,190,922
DATED : March 2, 1993
INVENTOR(S) : Jay R. Luly, Megumi Kawai, Paul E. Wiedman.

It is certified that error appears in the above-identified patent and that said Letters Patent is hereby corrected as shown below:

COLUMN 25, LINE 16: Replace "(1-(" with --[1-(--

COLUMN 25, LINE 26: Replace "(105) with --(1.05)--

COLUMN 25, LINE 32: Replace "3cyclohexylpropanoyl" with --3-cyclohexylpropanoyl--

COLUMN 43, LINE 2: Replace "Example b 119" with --Example 119--

COLUMN 64, LINE 64: Replace "is CH2" with --is $CH_2$--

COLUMN 65, LINE 66: Replace "$R_{99}C_{100}$" with --$CR_{99}R_{100}$--

COLUMN 67, LINE 25: Replace "$R_{99}C_{100}$" with --$CR_{99}R_{100}$--

COLUMN 68, LINE 48: Replace "$R_{99}C_{100}$" with --$CR_{99}R_{100}$--

Signed and Sealed this

Twenty-seventh Day of June, 1995

Attest:

BRUCE LEHMAN

Attesting Officer

Commissioner of Patents and Trademarks